(12) United States Patent
Suresh

(10) Patent No.: US 12,379,267 B2
(45) Date of Patent: Aug. 5, 2025

(54) SPREAD BRIDGE XY FORCE SENSOR

(71) Applicant: Intuitive Surgical Operations, Inc., Sunnyvale, CA (US)

(72) Inventor: Ashwinram Suresh, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 327 days.

(21) Appl. No.: 17/776,429

(22) PCT Filed: Nov. 15, 2020

(86) PCT No.: PCT/US2020/060636
§ 371 (c)(1),
(2) Date: May 12, 2022

(87) PCT Pub. No.: WO2021/097386
PCT Pub. Date: May 20, 2021

(65) Prior Publication Data
US 2022/0404218 A1    Dec. 22, 2022

Related U.S. Application Data

(60) Provisional application No. 62/936,349, filed on Nov. 15, 2019, provisional application No. 62/936,350, (Continued)

(51) Int. Cl.
*G01L 1/22* (2006.01)
*A61B 34/30* (2016.01)
(Continued)

(52) U.S. Cl.
CPC ............ *G01L 1/2262* (2013.01); *A61B 34/30* (2016.02); *G01L 1/2287* (2013.01); (Continued)

(58) Field of Classification Search
CPC ... G01L 1/2262; G01L 1/2287; G01L 1/2281; G01L 5/1627; G01L 25/00; A61B 34/30
See application file for complete search history.

(56) References Cited

U.S. PATENT DOCUMENTS

| 2,927,292 A | 3/1960 | Hunt et al. | |
| 3,576,128 A * | 4/1971 | Lockery | G01L 1/2262 |
| | | | 73/862.633 |

(Continued)

FOREIGN PATENT DOCUMENTS

| CN | 108603799 A | 9/2018 |
| CN | 110160681 A | 8/2019 |

(Continued)

OTHER PUBLICATIONS

International Search Report and Written Opinion for Application No. PCT/US2020/060636, mailed Apr. 28, 2021, 16 pages.

(Continued)

*Primary Examiner* — Helen C Kwok

(57) ABSTRACT

A force sensor is provided for use with an instrument. Accordingly, the force sensor includes a beam and a set of half-bridges that are arranged on the surface of the beam. Two of the half-bridges include tension resistors, while the other two half-bridges compression resistors. The half-bridges are arranged on the beam surface such that redundant measurements of orthogonal components of a force imparted to the beam can be made using four different combinations of three of the half-bridges.

18 Claims, 36 Drawing Sheets

Related U.S. Application Data filed on Nov. 15, 2019, provisional application No. 62/936,351, filed on Nov. 15, 2019.

(51) Int. Cl.
  *G01L 5/1627* (2020.01)
  *G01L 25/00* (2006.01)
(52) U.S. Cl.
  CPC ............ *G01L 5/1627* (2020.01); *G01L 25/00* (2013.01); *G01L 1/2281* (2013.01)

(56) References Cited

U.S. PATENT DOCUMENTS

| | | | |
|---|---|---|---|
| 3,878,713 A | 4/1975 | Mole | |
| 3,929,009 A | 12/1975 | Lutz et al. | |
| 3,985,025 A | 10/1976 | Ormond | |
| 3,993,166 A | 11/1976 | Senour | |
| 4,034,778 A | 7/1977 | Sage et al. | |
| 4,094,192 A | 6/1978 | Watson et al. | |
| 4,223,752 A | 9/1980 | Belcher | |
| 4,325,048 A * | 4/1982 | Zaghi | G01L 1/2225 |
| | | | 73/862.634 |
| 4,329,878 A * | 5/1982 | Utner | G01L 1/2262 |
| | | | 73/776 |
| 4,331,035 A | 5/1982 | Eisele et al. | |
| 4,343,198 A | 8/1982 | Jendrzejczyk | |
| 4,369,663 A | 1/1983 | Venturello et al. | |
| 4,419,734 A | 12/1983 | Wolfson et al. | |
| 4,448,083 A | 5/1984 | Hayashi | |
| 4,456,293 A | 6/1984 | Panissidi | |
| 4,522,072 A | 6/1985 | Sulouff et al. | |
| 4,555,955 A | 12/1985 | Morgan et al. | |
| 4,640,138 A | 2/1987 | Meyer et al. | |
| 4,657,097 A | 4/1987 | Griffen | |
| 4,683,755 A * | 8/1987 | Samek | G01L 1/2293 |
| | | | 73/777 |
| 4,762,006 A | 8/1988 | Asakawa et al. | |
| 4,763,531 A | 8/1988 | Dietrich et al. | |
| 4,777,826 A | 10/1988 | Rud, Jr. et al. | |
| 4,787,256 A | 11/1988 | Cherbuy et al. | |
| 4,869,113 A | 9/1989 | Sarrazin | |
| 4,906,907 A | 3/1990 | Tsuchihashi et al. | |
| 4,932,253 A | 6/1990 | McCoy | |
| 5,327,791 A | 7/1994 | Walker | |
| 5,347,871 A | 9/1994 | D'Andrea et al. | |
| 5,513,536 A | 5/1996 | Reger et al. | |
| 5,723,826 A | 3/1998 | Kitagawa et al. | |
| 5,767,840 A | 6/1998 | Selker | |
| 5,784,542 A | 7/1998 | Ohm et al. | |
| 5,855,583 A | 1/1999 | Wang et al. | |
| 5,889,214 A | 3/1999 | Kang et al. | |
| 5,894,094 A | 4/1999 | Kuchler et al. | |
| 5,969,268 A | 10/1999 | Sommerfeld et al. | |
| 6,038,933 A | 3/2000 | Meyer | |
| 6,197,017 B1 | 3/2001 | Brock et al. | |
| 6,331,181 B1 | 12/2001 | Tierney et al. | |
| 6,394,998 B1 | 5/2002 | Wallace et al. | |
| 6,459,926 B1 | 10/2002 | Nowlin et al. | |
| 6,494,882 B1 | 12/2002 | Lebouitz et al. | |
| 6,532,830 B1 | 3/2003 | Jansen et al. | |
| 6,594,552 B1 | 7/2003 | Nowlin et al. | |
| 6,675,663 B1 | 1/2004 | Irion et al. | |
| 6,763,716 B2 | 7/2004 | Nagahara et al. | |
| 6,817,974 B2 | 11/2004 | Cooper et al. | |
| 6,835,173 B2 | 12/2004 | Couvillon, Jr. | |
| 6,871,552 B2 | 3/2005 | Liu et al. | |
| 6,902,560 B1 | 6/2005 | Morley et al. | |
| 6,910,392 B2 | 6/2005 | Lockery et al. | |
| 6,936,042 B2 | 8/2005 | Wallace et al. | |
| 6,979,873 B2 | 12/2005 | Fujii | |
| 6,994,708 B2 | 2/2006 | Manzo | |
| 7,083,571 B2 | 8/2006 | Wang et al. | |
| 7,169,141 B2 | 1/2007 | Brock et al. | |
| 7,174,792 B2 | 2/2007 | Ealey | |
| 7,302,139 B1 | 11/2007 | Ames | |
| 7,437,954 B2 | 10/2008 | Sakano | |
| 7,441,470 B2 | 10/2008 | Morimoto | |
| 7,500,406 B2 | 3/2009 | Morimoto | |
| 7,578,219 B2 | 8/2009 | Wu | |
| 7,594,445 B2 | 9/2009 | Hirabayashi et al. | |
| 7,603,917 B2 | 10/2009 | Graham et al. | |
| 7,665,371 B2 | 2/2010 | Mastinu et al. | |
| 7,743,672 B2 | 6/2010 | Kurtz et al. | |
| 7,779,705 B2 | 8/2010 | Mastinu et al. | |
| 7,935,130 B2 | 5/2011 | Williams | |
| 8,281,670 B2 | 10/2012 | Larkin et al. | |
| 8,444,631 B2 | 5/2013 | Yeung et al. | |
| 8,465,474 B2 | 6/2013 | Blumenkranz | |
| 8,479,969 B2 | 7/2013 | Shelton, IV | |
| 8,491,574 B2 | 7/2013 | Blumenkranz | |
| 8,496,647 B2 | 7/2013 | Blumenkranz et al. | |
| 8,506,555 B2 | 8/2013 | Ruiz Morales | |
| 8,551,115 B2 | 10/2013 | Steger et al. | |
| 8,561,473 B2 | 10/2013 | Blumenkranz | |
| 8,602,288 B2 | 12/2013 | Shelton, IV et al. | |
| 8,620,473 B2 | 12/2013 | Diolaiti et al. | |
| 8,621,939 B2 | 1/2014 | Blumenkranz et al. | |
| 8,628,518 B2 | 1/2014 | Blumenkranz et al. | |
| 8,771,270 B2 | 7/2014 | Burbank | |
| 8,800,838 B2 | 8/2014 | Shelton, IV | |
| 9,028,494 B2 | 5/2015 | Shelton, IV et al. | |
| 9,101,734 B2 | 8/2015 | Selkee | |
| 9,204,923 B2 | 12/2015 | Manzo et al. | |
| 9,232,979 B2 | 1/2016 | Parihar et al. | |
| 9,707,684 B2 | 7/2017 | Ruiz et al. | |
| 9,782,214 B2 | 10/2017 | Houser et al. | |
| 9,855,102 B2 | 1/2018 | Blumenkranz | |
| 9,952,107 B2 | 4/2018 | Blumenkranz et al. | |
| 10,085,809 B2 | 10/2018 | Blumenkranz et al. | |
| 10,390,896 B2 | 8/2019 | Blumenkranz | |
| 10,620,066 B2 | 4/2020 | Blumenkranz et al. | |
| 11,460,360 B2 | 10/2022 | Suresh | |
| 2003/0140713 A1 * | 7/2003 | Ohsato | G01L 5/162 |
| | | | 73/862.041 |
| 2003/0150276 A1 | 8/2003 | Christensen et al. | |
| 2005/0050960 A1 | 3/2005 | Haines | |
| 2005/0103123 A1 | 5/2005 | Newman | |
| 2006/0070464 A1 | 4/2006 | Walker | |
| 2007/0096666 A1 | 5/2007 | Ippisch | |
| 2007/0151390 A1 * | 7/2007 | Blumenkranz | G01L 5/22 |
| | | | 74/490.06 |
| 2007/0151391 A1 | 7/2007 | Larkin et al. | |
| 2008/0047366 A1 * | 2/2008 | Kuriyama | G01L 1/2268 |
| | | | 73/862.627 |
| 2008/0065111 A1 | 3/2008 | Blumenkranz et al. | |
| 2008/0295610 A1 * | 12/2008 | Inamori | G01L 5/223 |
| | | | 73/862.044 |
| 2009/0248038 A1 | 10/2009 | Blumenkranz et al. | |
| 2009/0320610 A1 * | 12/2009 | Ohsato | G01L 1/18 |
| | | | 29/621.1 |
| 2009/0324161 A1 | 12/2009 | Prisco | |
| 2010/0024574 A1 | 2/2010 | Werthschutzky et al. | |
| 2010/0324453 A1 | 12/2010 | Lal et al. | |
| 2011/0071543 A1 | 3/2011 | Prisco et al. | |
| 2011/0282356 A1 | 11/2011 | Solomon et al. | |
| 2011/0283804 A1 * | 11/2011 | Jost | G01L 9/0055 |
| | | | 73/774 |
| 2012/0116391 A1 | 5/2012 | Houser et al. | |
| 2013/0282024 A1 | 10/2013 | Blumenkranz | |
| 2013/0291654 A1 | 11/2013 | Blumenkranz et al. | |
| 2014/0137667 A1 | 5/2014 | Blumenkranz et al. | |
| 2014/0257333 A1 | 9/2014 | Blumenkranz | |
| 2015/0021105 A1 | 1/2015 | Head et al. | |
| 2015/0075250 A1 | 3/2015 | Kosa et al. | |
| 2015/0330856 A1 | 11/2015 | Chiou et al. | |
| 2015/0374447 A1 | 12/2015 | Blumenkranz et al. | |
| 2015/0374449 A1 | 12/2015 | Chowaniec et al. | |
| 2016/0146685 A1 | 5/2016 | Chiou et al. | |
| 2016/0147353 A1 * | 5/2016 | Filiz | G01L 1/16 |
| | | | 345/174 |
| 2017/0261306 A1 | 9/2017 | Ausserlechner et al. | |
| 2018/0067003 A1 | 3/2018 | Michiwaki | |
| 2018/0334214 A1 * | 11/2018 | Cuban | G01G 3/1404 |

(56) References Cited

U.S. PATENT DOCUMENTS

| | | |
|---|---|---|
| 2019/0069966 A1 | 3/2019 | Petersen et al. |
| 2019/0336229 A1 | 11/2019 | Blumenkranz |
| 2020/0129261 A1 | 4/2020 | Eschbach |
| 2020/0278265 A1* | 9/2020 | Suresh ............... G01L 1/2287 |
| 2022/0341796 A1* | 10/2022 | Suresh ............... H01C 17/2416 |
| 2022/0390300 A1 | 12/2022 | Suresh |
| 2022/0404218 A1* | 12/2022 | Suresh ............... G01L 1/2287 |

FOREIGN PATENT DOCUMENTS

| | | |
|---|---|---|
| DE | 3405168 A1 | 8/1985 |
| DE | 19523523 A1 | 1/1996 |
| DE | 10013059 A1 | 9/2001 |
| DE | 202007010974 U1 | 10/2007 |
| EP | 0244324 B1 | 7/1989 |
| EP | 1965717-81 | 5/2012 |
| EP | 2289455 B1 | 11/2019 |
| ES | 2000423 A4 | 3/1988 |
| FR | 2598226 B1 | 4/1989 |
| FR | 2693397 A1 | 1/1994 |
| GB | 2293453 B | 10/1996 |
| GB | 2475081 A | 5/2011 |
| JP | S5612526 A | 2/1981 |
| JP | H02223836 A | 9/1990 |
| JP | H07190865 A | 7/1995 |
| JP | H0875572 A | 3/1996 |
| JP | H08201202 A | 8/1996 |
| JP | 2001153735 A | 6/2001 |
| JP | 2005103056 A | 4/2005 |
| JP | 2005274395 A | 10/2005 |
| JP | 5853121 B1 | 2/2016 |
| KR | 970004983 A | 1/1997 |
| KR | 100703861 B1 | 4/2007 |
| KR | 20080089582 A | 10/2008 |
| KR | 101296220 B1 | 8/2013 |
| WO | WO-2007111737 A2 | 10/2007 |
| WO | WO-2007120329 A2 | 10/2007 |
| WO | WO-2015120108 A1 | 8/2015 |
| WO | WO-2019099562 A1 | 5/2019 |
| WO | WO-2021055509 A2 | 3/2021 |
| WO | WO-2021097386 A1 | 5/2021 |

OTHER PUBLICATIONS

Mayer H., et al., "Upgrading Instruments for Robotic Surgery," Proceedings of Australasian Conference on Robotics and Automation, 2004, Canberra, Australia, pp. 1-6.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for Chinese Application No. CN202080093865, mailed Mar. 16, 2024, 18 pages.

* cited by examiner

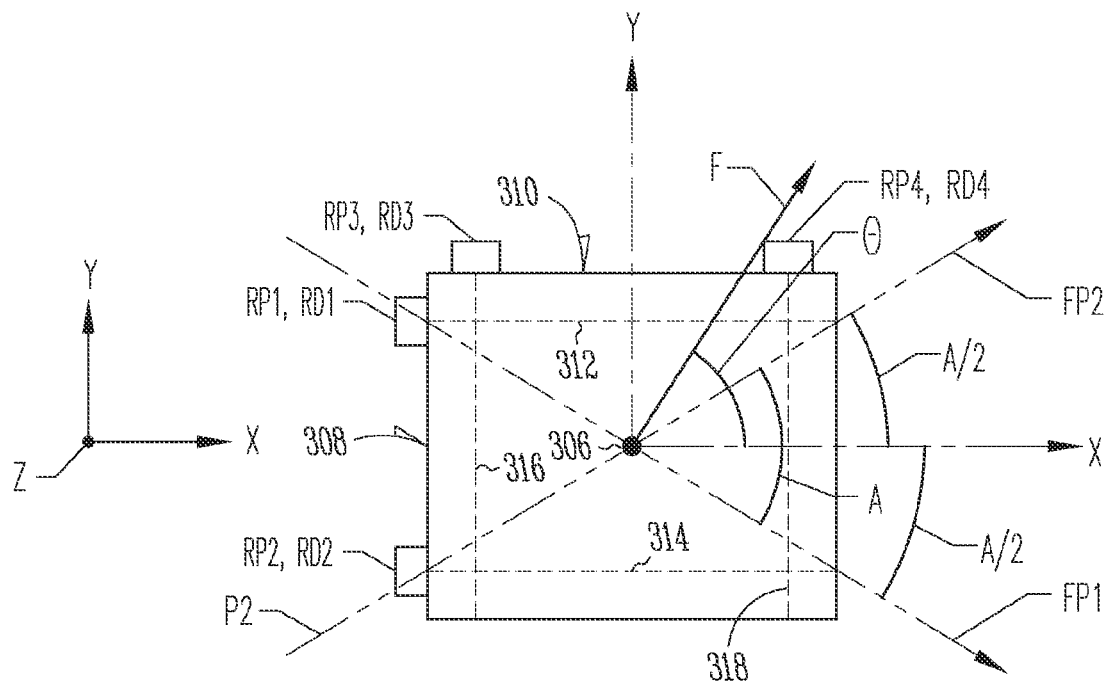
Fig. 9A
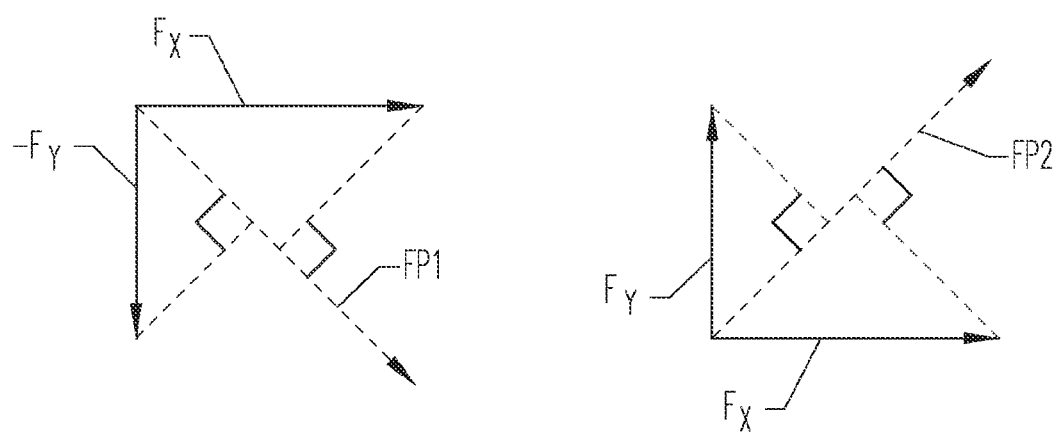
Fig. 9B
Fig. 9C

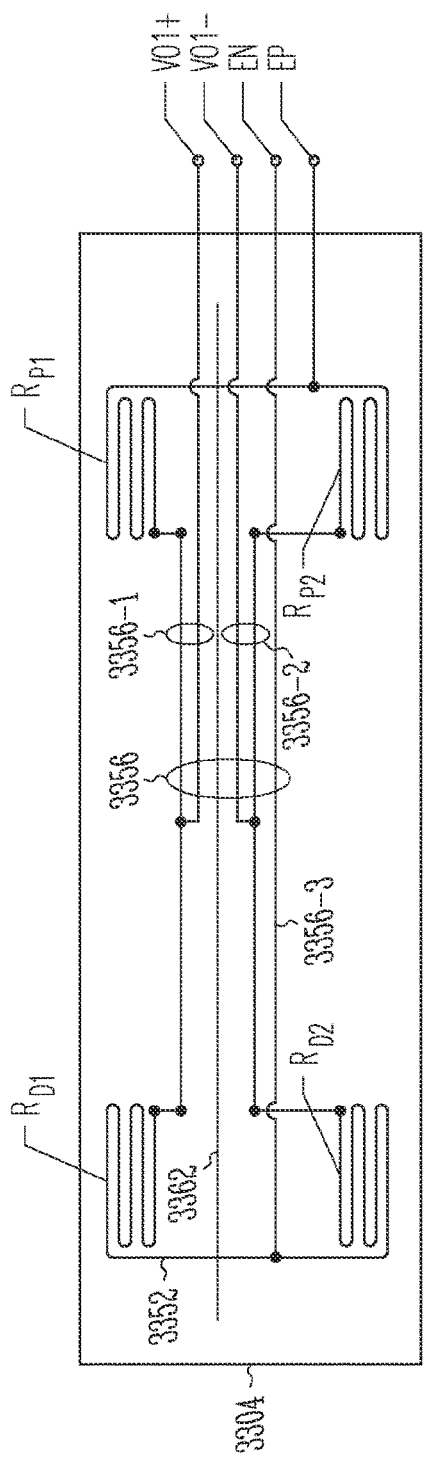
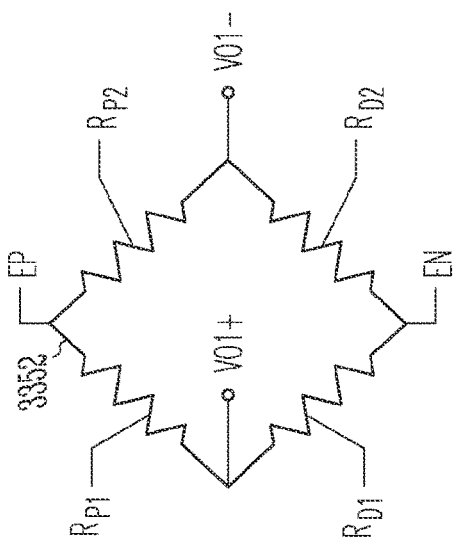
Fig. 38A
Fig. 38B

SPREAD BRIDGE XY FORCE SENSOR

CLAIM OF PRIORITY

This application is a U.S. national stage filing under 35 U.S.C. § 371 of International Application No. PCT/US2020/060636, entitled "SPREAD BRIDGE XY FORCE SENSOR," filed Nov. 15, 2020, which is a continuation of and claims the benefit of priority to U.S. Patent Application Ser. No. 62/936,349, entitled "SPREAD BRIDGE ADJACENT SIDED XY FORCE SENSOR," filed on Nov. 15, 2019, and to U.S. Patent Application Ser. No. 62/936,350, entitled "REDUNDANT MULTIPLE HALF-BRIDGE XY FORCE SENSOR," filed on Nov. 15, 2019, and to U.S. Patent Application Ser. No. 62/936,351, entitled "SPREAD BRIDGE REVERSE SIDED XY FORCE SENSOR," filed on Nov. 15, 2019, each of which is incorporated by reference herein in its entirety.

BACKGROUND

Force sensing and feedback during a minimally invasive surgical procedure may bring better immersion, realism and intuitiveness to a surgeon performing the procedure. For the best performance of haptics rendering and accuracy, force sensors may be placed on a surgical instrument and as close to the anatomical tissue interaction as possible. One approach is to embed a force sensor at a distal end of a surgical instrument shaft with electrical strain gauges formed on the force transducer, through overlay of a conducive sheet having cut-out circuit pattern, printing or additive deposition processes, for example, to measure strain imparted to the surgical instrument.

FIG. 1 is an illustrative drawing representing a prior force sensor that includes a rectangular beam with four full-Wheatstone bridges (full-bridges). A typical bridge circuit includes an electrical circuit topology in which two circuit branches (usually in parallel with each other) are bridged by a third branch between the first two branches to provide an offset voltage between the two branches at some intermediate point along them. The illustrative force sensor includes two full-bridges on each of two adjacent orthogonal sides of the beam to measure forces orthogonal to a longitudinal axes of the beam. The beam can be secured to a distal portion of a surgical instrument shaft to sense forces orthogonal to a longitudinal axis of the shaft. For example, a forces applied orthogonal to a side of the beam (i.e. an X or Y force) can be determined by subtracting force measurements determined by the full-bridges at proximal and distal end portions of that side of the beam.

A force sensor can experience a variety of different strain sources including: an orthogonal force of interest to be measured, moment, off axis force, off axis moment, compression/tension, torsion, ambient temperature and gradient temperature. Each of the example full-bridges can cancel the following stress: temperature, torsion, off axis force, and off axis moment. Each individual full-bridge output can indicate stress due to force, moment, and compression/tension. In the example force sensor, the subtraction of an output value produced by a proximal full-bridge formed on a side from an output value produced by a distal full-bridge on the same side, can cancel a moment, resulting in an output value that represents the orthogonal force of interest to be measured.

A surgical instrument force sensor can be critical to ensuring patient safety. Accordingly, force sensor error detection can be required to protect against harm by detecting force sensor failures. One approach to error detection can be to provide additional full-bridges to produce redundant force measurements that can be compared to detect errors. However, limited space on beam sides can make adding more full-bridges on a side impractical. Moreover, some manufacturing processes typically are limited to formation of bridges at most on two sides. Formation of bridges on four sides increases manufacturing cost significantly.

BRIEF DESCRIPTION OF THE DRAWINGS

In the drawings, which are not necessarily drawn to scale, like numerals may describe similar components in different views. Like numerals having different letter suffixes may represent different instances of similar components.

The drawings illustrate generally, by way of example, but not by way of limitation, various embodiments discussed in the present document.

FIG. 9A is an illustrative cross-sectional end view of the example beam of FIG. 4 indicating the resistors on the first side and indicating a first plane force and a second plane force.

FIG. 9B is an illustrative force diagram that indicates X and Y force components of the first plane force imparted to a first proximal resistor and a first distal resistor in response to an applied force.

FIG. 9C is an illustrative force diagram that indicates X and Y force components of the second plane force imparted to a second proximal resistor and second distal resistor in response to an applied force.

FIG. 38A is an illustrative side view of an example beam showing a spread layout of Wheatstone bridge and showing routing of center conductor traces.

FIG. 38B is an illustrative first schematic circuit diagram representation of the first and second full-Wheatstone bridges of FIG. 38A.

SUMMARY

A force sensor includes a beam with four Wheatstone half-bridges ("half bridges") located on a beam surface. The beam includes a proximal portion and a distal portion, a longitudinal center axis and a neutral axis that extends along a beam surface parallel to the center axis. First and second half-bridges include tension resistors. Third and fourth half-bridges include compression resistors. The first and third half-bridges are arranged along a first side axis. The second and fourth half-bridges are arranged along a second a side axis. The first and second side axes extend along the beam surface parallel to the neutral axis on opposite sides of the neutral axis and equidistant from the neutral axis.

Each of four combinations of the three half-bridges can be used to produce separate measurements of orthogonal components of a force imparted to the beam. Comparison of the separate measurements provides an indication of whether one or more of the half-bridges has a malfunction. A malfunction is reported as a sensor error.

DETAILED DESCRIPTION

Spread Bridge Adjacent Sided XY Force Sensor

Figure 1:
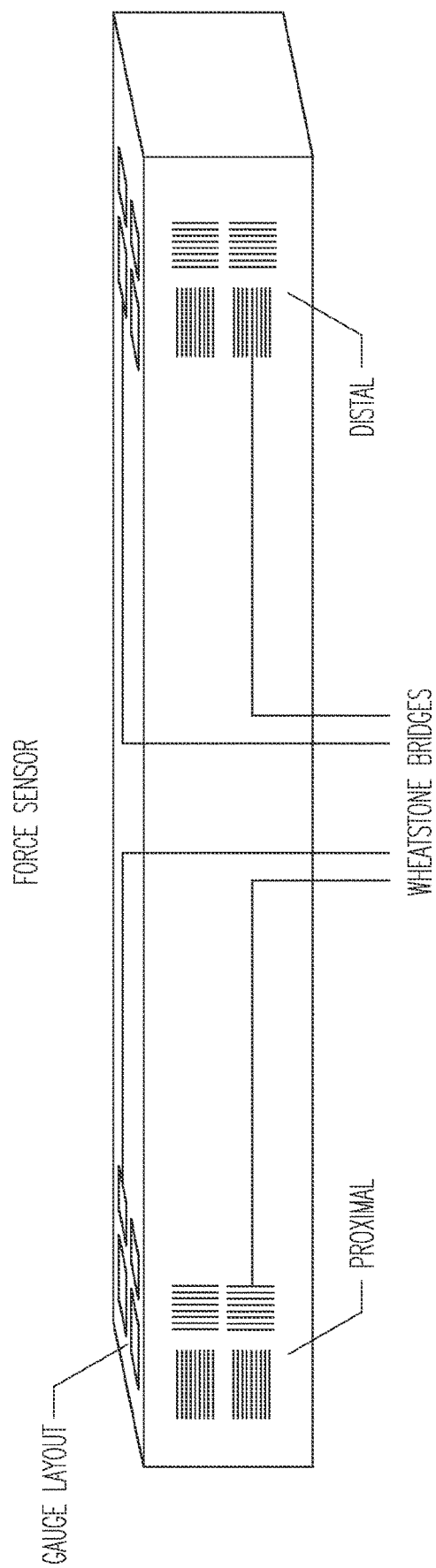
FIG. 1 is an illustrative drawing representing an example prior force sensor that includes a rectangular beam with four full-Wheatstone bridges (full-bridges).
Figure 2:
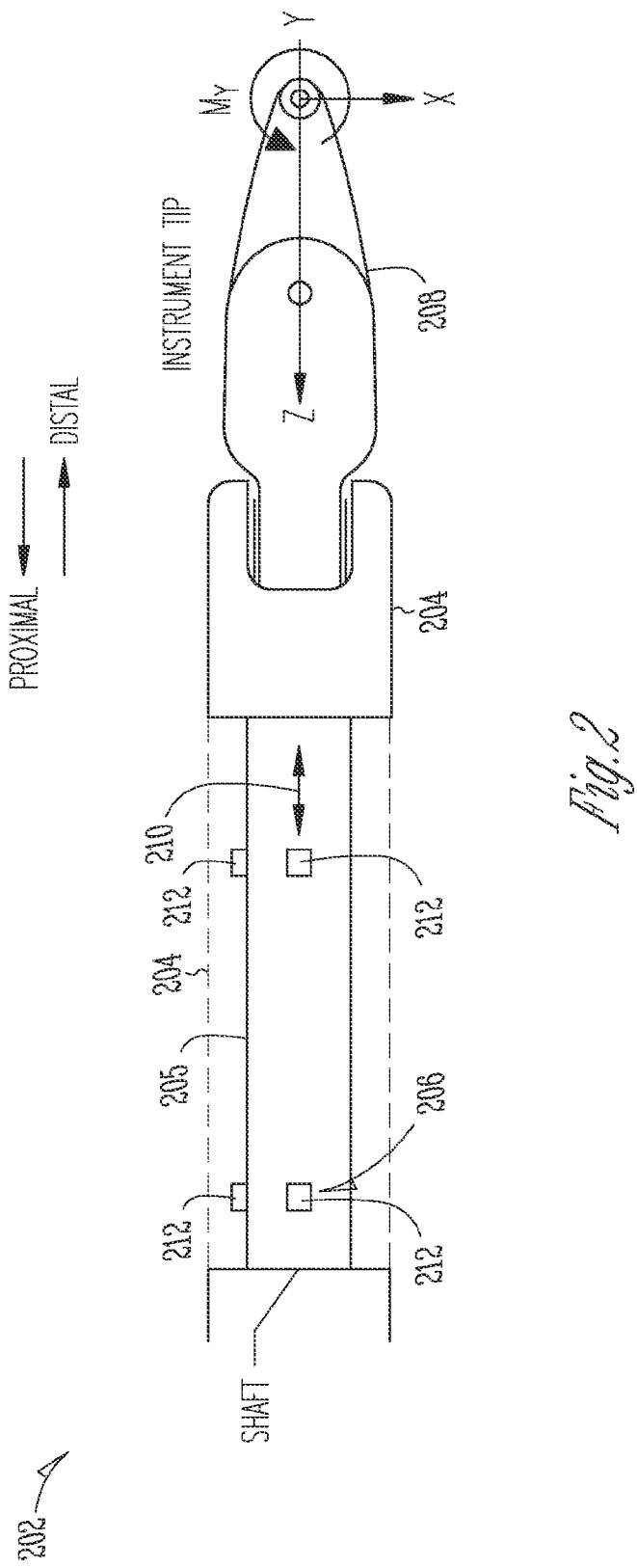
FIG. 2 is an illustrative side elevation view of a distal portion of a surgical instrument with an elongated shaft having a force sensor beam mounted thereon, in accordance with some examples.

FIG. 2 is an illustrative side view of a distal portion of an example surgical instrument 202 with an elongated shaft 204, shown in partially cut way, and a force sensor 205. The force sensor 205 is mounted to a distal end portion of the shaft 204 and includes a beam 206 having multiple strain gauge resistors 212 located thereon. The surgical instrument 202 includes an end effector 208, which can include articulatable jaws, for example. During a surgical procedure, the end effector 208 contacts anatomical tissue, which can result in imparting of X, Y, or Z direction forces to the force sensor 206 and that may result in moment forces such as a moment My about a Y-direction axis, for example. The force sensor 205, which includes a longitudinal axis 210, can be used to measure X and Y forces perpendicular to the longitudinal axis 210.

Figure 3A:
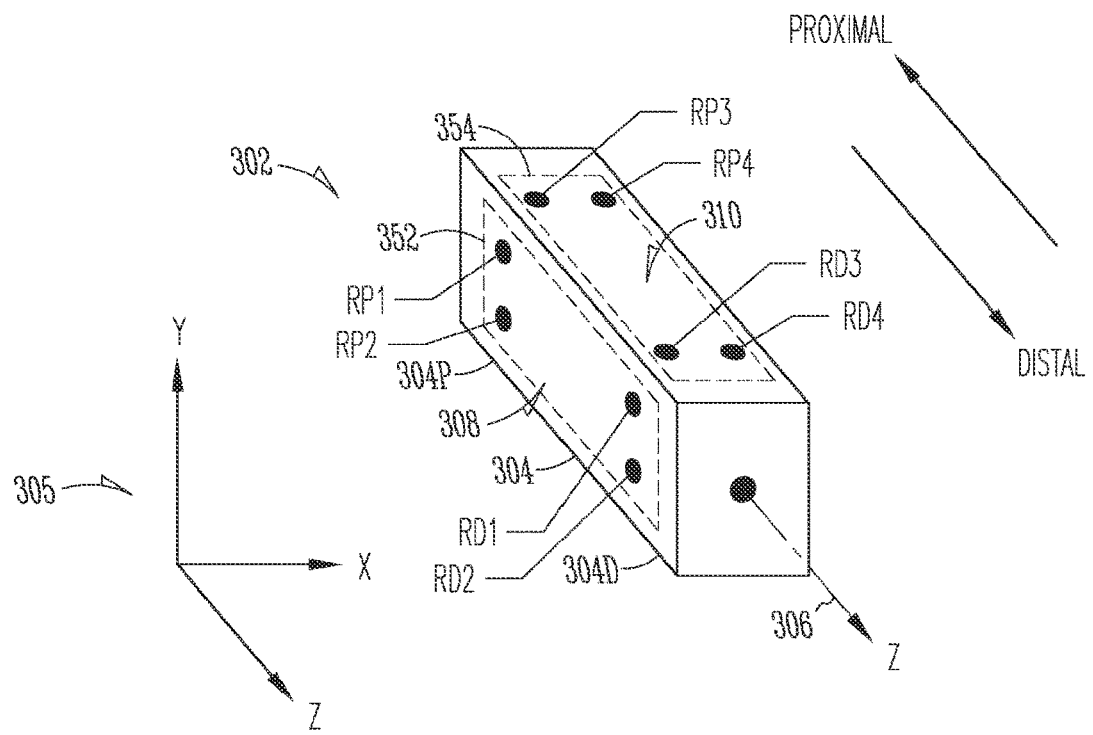
FIG. 3A is an illustrative perspective view of an example force sensor that includes a rectangular beam with two spread Wheatstone bridge circuits located on each of two adjacent sides thereof.

FIG. 3A is an illustrative perspective view of an example force sensor 302 that includes a rectangular beam 304 with spread Wheatstone bridge circuits located on each of two adjacent sides thereof. A first full-Wheatstone bridge 352 (indicated by dashed lines) includes first ($R_{P1}$), second ($R_{D1}$), third ($R_{P2}$), and fourth ($R_{D2}$) resistors. A second full-Wheatstone bridge 354 (indicated by dashed lines) includes fifth ($R_{P3}$), sixth ($R_{D3}$), seventh ($R_{P4}$), and eighth ($R_{D4}$) resistors. In an example first full-Wheatstone bridge 352, the first and second resistors are coupled in a first half bridge, and the third and fourth resistors are coupled in a second half bridge. In an example second full-Wheatstone bridge, the fifth and sixth resistors are coupled in a third half bridge, and the seventh and eighth resistors are coupled in a fourth half bridge. An (X, Y, Z) beam coordinate system 305 is shown to explain force directions relative to the beam 304. An example beam 304 can have a rectangular cross-section with planar side faces. More particularly, an example beam can have a square cross-section. The beam 304 includes a proximal beam portion 304P and a distal beam portion 304D and includes a longitudinal center axis 306 extending between the proximal and distal beam portions. The force sensor 302 includes example resistors $R_{P1}$-$R_{P4}$ and $R_{D1}$-$R_{D4}$ that have matching resistor values.

The resistors can be placed on the beam 304 manually or using automated machinery and can be adhered to the beam using an adhesive such as epoxy. Alternatively, the resistors can be deposited and laser etched directly on to the beam 304. In both cases, an electrical circuit can be completed externally using wirebonds and flexible printed circuit.

A first proximal strain gauge resistor ('resistor') $R_{P1}$ and a second proximal resistor $R_{P2}$ are located at a proximal beam portion 304P of a first side 308 of the beam 304. A first distal resistor $R_{D1}$ and a second distal resistor $R_{D2}$ are located at a distal beam portion of the first side 308 of the beam 304. A first set of resistors $R_{P1}$-$R_{P2}$ and $R_{D1}$-$R_{D2}$ located on the first side 308 of the beam are arranged in a first spread full-Wheatstone bridge, explained below. A third proximal resistor $R_{P3}$ and a fourth proximal resistor $R_{P4}$ are located at a proximal beam portion 304P of a second side 310 of the beam 304. A third distal resistor $R_{D3}$ and a fourth distal resistor $R_{D4}$ are located at a distal beam portion 304D of the second side 310 of the beam 304. The first side 308 of the example beam 304 is adjacent to the second side 310 of the example beam 304. A second set of resistors $R_{P3}$-$R_{P4}$ and $R_{D3}$-$R_{D4}$ are arranged in a second spread full-Wheatstone bridge, explained below.

As explained more fully below, the first and second full-bridge circuits are 'spread' in that portions of each bridge circuit are laterally spaced apart from one another on the beam 304. For example, each full-bridge can include two half-bridges that are laterally spread apart from each other. An advantage of laterally spreading apart the half-bridges is that conductor traces that couple resistors to bias voltages or to one another, for example, can be routed to pass through the middle of a face of a beam 304 or close a neutral axis of the beam 304, on each face of the beam. Alternatively, in a circular cross-section beam (not shown), conductor traces advantageously can be routed along the neutral axes of individual half-bridges. This routing helps reduce strain on the traces and in turn improves the accuracy of the sensor, by rejecting unwanted signal. As explained more fully below, the first and second proximal resistors $R_{P1}$, $R_{P2}$ and the first and second distal resistors $R_{D1}$, $R_{D2}$ located at the first side 308 of the beam 304 act as Y-direction force sensor elements, and the third and fourth proximal resistors $R_{P3}$, $R_{P4}$ and the third and fourth distal resistors $R_{D3}$, $R_{D4}$ located at the second side 310 of the beam act as X-direction force sensor elements.

Each of resistors $R_{P1}$-$R_{P4}$ and $R_{D1}$-$R_{D4}$ is the same type of strain gauge resistor. More particularly in the example force sensor 302 described herein, the resistors $R_{P1}$-$R_{P4}$ and $R_{D1}$-$R_{D4}$ are tension type gauge resistors used to measure tensile strain. In an alternative example force sensor, the set of resistors can be compression type gauge resistors used to measure compression strain. As used herein reference to a set resistors having 'matching type' refers to a set of resistors in which either all resistors are tension resistors or all resistors are compression resistors. Resistors that have matching type are more likely to have similar sensitivity and performance, making a sensor better suited for situation of low signal to noise ratio where the common mode cancellation is crucial and much better. In general, although either tension or compression gauge resistors can be used to determine X direction and Y direction forces, which are orthogonal to each other, tension strain gauge resistors, in general, are more sensitive than compression gauge resistors.

Figure 3B:
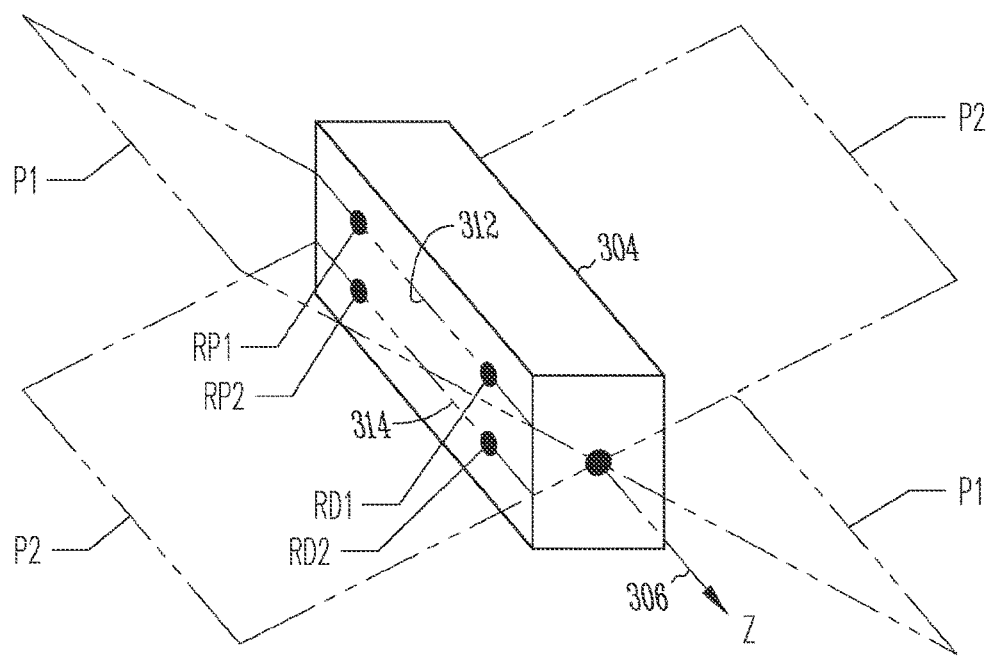
FIG. 3B shows the illustrative perspective view of the force sensor of FIG. 3A that further shows an imaginary first plane and an imaginary second plane.

FIG. 3B shows the illustrative perspective view of the force sensor 302 of FIG. 3A that further shows an imaginary first plane P1 and an imaginary second plane P2. The first proximal resistor $R_{P1}$ and the first distal resistor $R_{D1}$ are arranged upon the first side of the beam 304 within the first imaginary plane P1 in which the center axis extends 306 and that defines a first lateral side axis 312 at a location on the first side 308 of the beam 304 along which the first plane P1 intersects the first side. The first lateral axis 312 and the center axis 306 extend parallel to one another. An example first lateral side axis 312 extends through the first proximal resistor $R_{P1}$ and through the first distal resistor $R_{D1}$. Moreover, an example first lateral side axis 312 bisects the example first proximal resistor $R_{P1}$ and bisects an example first distal resistor $R_{D1}$.

Still referring to FIG. 3B, the second proximal resistor $R_{P2}$ and the second distal resistor $R_{D2}$ are arranged upon the first side of the beam 304 within a second imaginary plane P2 in which the center axis 306 extends and that defines a second lateral side axis 314 at a location on the first side 308 of the beam 304 along which the second plane P2 intersects the first side 308. The second later axis 314 and the center axis 306 extend parallel to one another. An example second lateral side axis 314 extends through the second proximal resistor $R_{P2}$ and through the second distal resistor $R_{D2}$. Moreover, an example second lateral side axis 314 bisects the example second proximal resistor $R_{P2}$ and bisects an example second distal resistor $R_{D2}$.

Figure 3C:
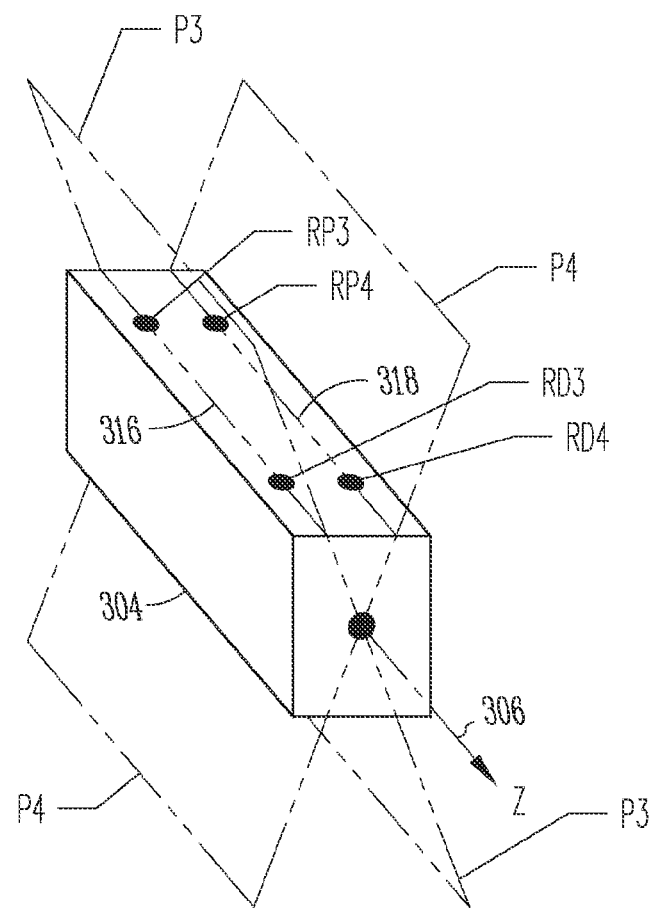
FIG. 3C shows the illustrative perspective view of the force sensor of FIG. 3A that further shows an imaginary third plane and an imaginary fourth plane.

FIG. 3C shows the illustrative perspective view of the force sensor 302 of FIG. 3A that further shows an imaginary third plane P3 and an imaginary fourth plane P4. The third proximal resistor $R_{P3}$ and the third distal resistor $R_{D3}$ are arranged upon the second side 310 of the beam 304, (adjacent to the first side 308, within the third imaginary plane P3 in which the center axis 306 extends and that defines a third lateral side axis 316 at a location on the second side 310 of the beam 304 along which the third plane P3 intersects the second side 310. An example third lateral side axis 316 extends through the third proximal resistor $R_{P3}$ and through the third distal resistor $R_{D3}$. Moreover, an example third side axis bisects the example third proximal resistor $R_{P3}$ and bisects an example third distal resistor $R_{D3}$.

Still referring to FIG. 3C, the fourth proximal resistor $R_{P4}$ and the fourth distal resistor $R_{D4}$ are arranged upon the second side 310 of the beam 304 within a fourth imaginary plane P4 in which the center axis 306 extends and that defines a fourth lateral side axis 318 at a location on the second side 310 of the beam 304 along which the fourth plane P4 intersects the second side 310 of the beam 304 and that includes the center axis 306. An example fourth lateral side axis 318 extends through the fourth proximal resistor $R_{P4}$ and through the fourth distal resistor $R_{D4}$. More particularly, an example fourth lateral side axis bisects an example fourth proximal resistor $R_{P4}$ and bisects an example first distal resistor $R_{D4}$.

Figure 4:
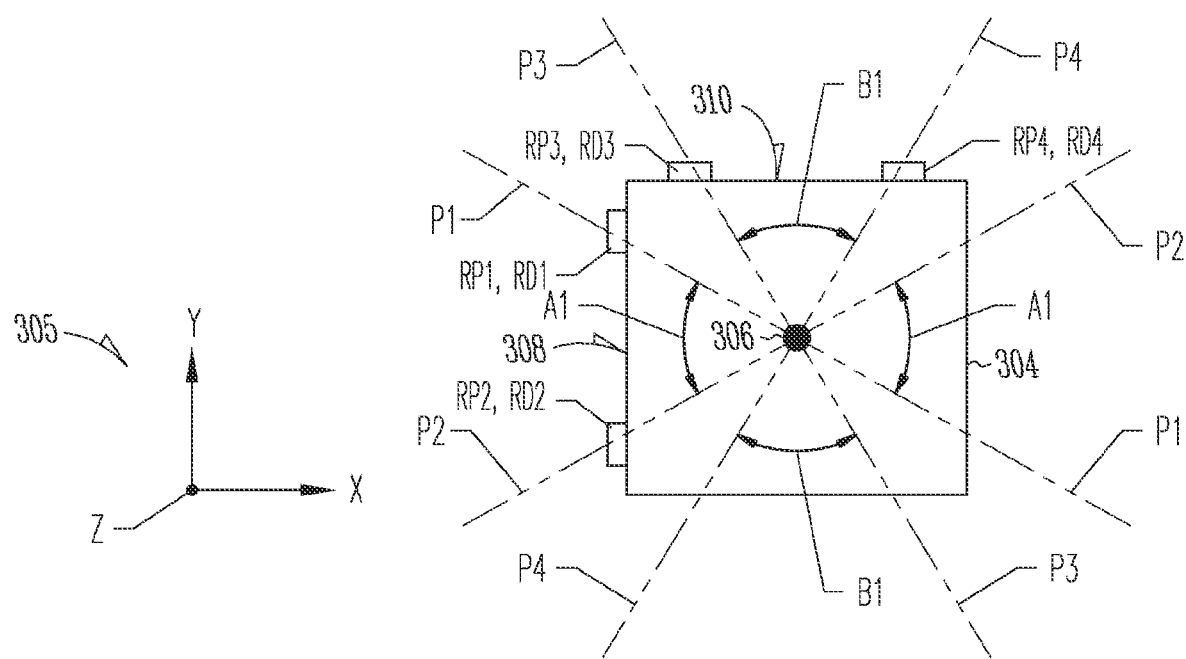
FIG. 4 is an illustrative proximal direction cross-section view of the example beam of FIGS. 3A-3B showing intersection of the imaginary planes at the longitudinal center axis.
Figure 5B:
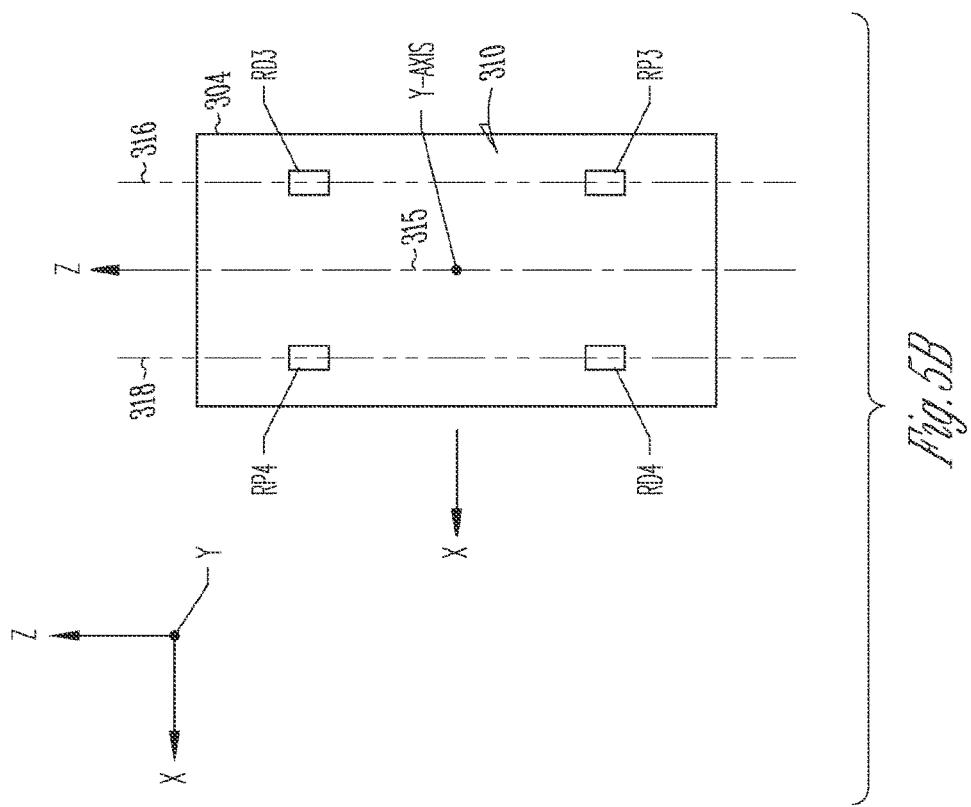
FIG. 5B is a side view showing arrangement of resistors on the second side of the beam.
Figure 5A:
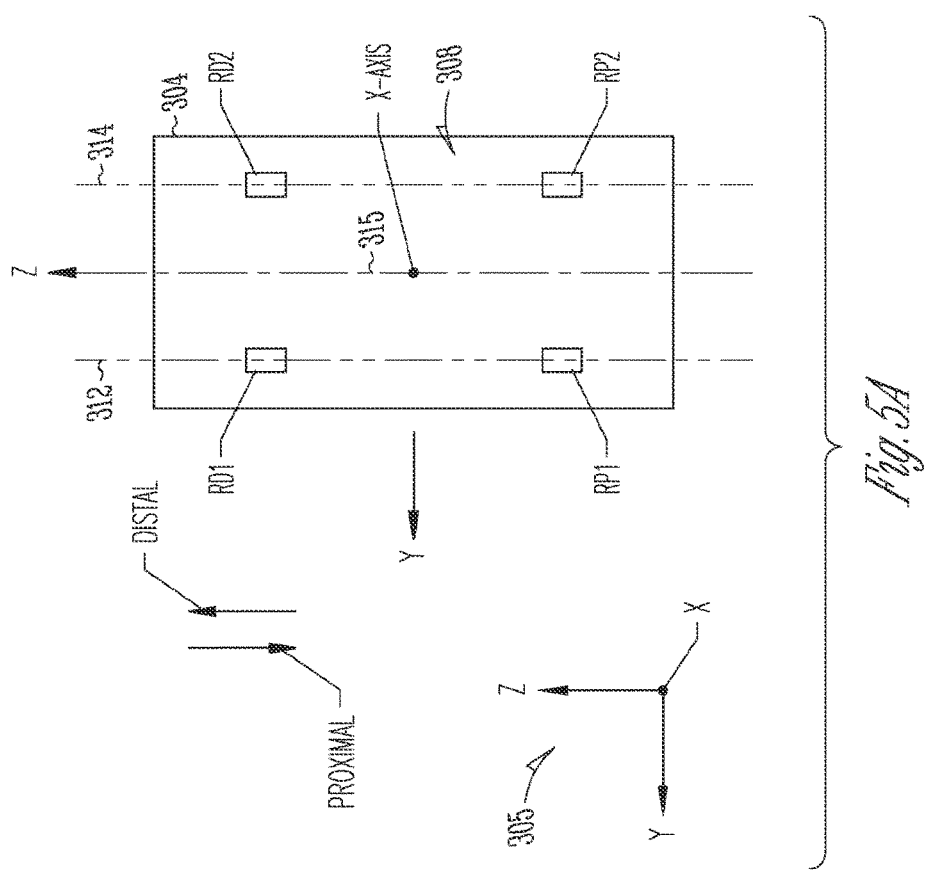
FIG. 5A is a side view showing arrangement of resistors on the first side 308 of the beam.

FIG. 4 is an illustrative proximal direction cross-section view of the example beam 304 of FIGS. 3A-3B showing intersection of the imaginary planes at the longitudinal center axis 306. FIG. 5A is a side view showing arrangement of resistors $R_{P1}$-$R_{P2}$, $R_{D1}$-$R_{D2}$ on the first side 308 of the beam 304. FIG. 5B is a side view showing arrangement of resistors $R_{P3}$-$R_{P4}$, $R_{D3}$-$R_{D4}$ on the second side 310 of the beam 304.

Referring to FIG. 4, the proximal direction end view of the beam 304 shows side views of the imaginary first through fourth planes P1-P4 that intersect along the longitudinal center axis 306. The (X, Y, Z) beam coordinate system 305 is shown to explain force directions relative to the beam 304. It is noted that in FIG. 4, the Z axis is shown emerging from the page. The first and second planes P1, P2 are separated from one another about the center axis by a first separation angle A1. The second and third imaginary planes are separated from one another by a second separation angle B1. In an example force sensor 302, the first separation angle equals the second separation angle.

Referring to FIG. 5A, the first plane P1 is shown extending through the first proximal resistor $R_{P1}$ and the first distal resistor $R_{D1}$, which are arranged along the first lateral side axis 312 on the first side 308 of the beam 304, and the second plane P2 is shown extending through the second proximal resistor $R_{P2}$ and the second distal resistor $R_{D2}$, which are arranged along the second lateral side axis 314 on the first side 308 of the beam 304. The (X, Y, Z) beam coordinate system 305 is shown to explain force directions relative to the beam 304. It is noted that in FIG. 5A, the X axis is shown directed into the page. Size of the first separation angle A1 corresponds to lateral spacing distance at the first side 308, between the first and second lateral side axes 312, 314, and therefore, corresponds to lateral spacing between the a first resistor pair including the first proximal and distal resistors $R_{P1}$, $R_{D1}$ and a second resistor pair including the second proximal and distal resistors $R_{P2}$, $R_{D2}$. In an example force sensor 302 the first lateral side axis 312 and the second lateral side axis 314 are equidistant from a neutral axis 315 of the first side 308 of the beam 304, which extends within the first side face and which is equidistant from the opposite lateral edges of the first side 308, although equidistant spacing is not required.

Referring to FIG. 5B, the third plane P3 is shown extending through the third proximal resistor $R_{P3}$ and the third distal resistor $R_{D3}$, which are arranged along the third lateral side 316 axis on the second side 310 of the beam 304, and the fourth plane P4 is shown extending through the fourth proximal resistor $R_{P4}$ and the fourth distal resistor $R_{D4}$, which are arranged along the fourth lateral side axis 318 of the beam 304 on the second side 310 of the beam 304. The (X, Y, Z) beam coordinate system 305 is shown to explain force directions relative to the beam 304. It is noted that in FIG. 5B, the Y axis is shown emerging from the page. Size of the second separation angle B1 corresponds to lateral spacing distance at the second side 310, between the third and fourth lateral side axes 316, 318, and therefore, corresponds to lateral spacing between a third resistor pair including the third proximal and distal resistors $R_{P3}$, $R_{D3}$, and a fourth resistor pair including the fourth proximal and distal resistors $R_{P4}$, $R_{D4}$ are arranged. In an example force sensor 302 the third lateral side axis 316 and the fourth lateral side axis 318 are equidistant from a neutral axis 319 of the second side 310 of the beam 304, which extends within the second side face and which is equidistant from the opposite lateral edges of the second side 310.

Thus, a first pair of resistors, $R_{P1}$, $R_{D1}$ and a second pair of resistors, $R_{P2}$, $R_{D2}$ are positioned upon the first side 308 of the beam 304 laterally spread apart. In an example beam 304, the first pair of resistors is positioned in alignment with the first lateral side axis 312 and the second pair or resistors is positioned in alignment with the second lateral side axis 314, and the first and second lateral side axes are equally laterally spaced apart from and on opposite sides of the neutral axis 315 of the first side of the beam 304. More particularly, the first pair of resistors is positioned in alignment with the first lateral side axis 312 and the second pair or resistors is positioned in alignment with the second lateral side axis 314. Moreover, a third pair of resistors, $R_{P3}$, $R_{D3}$ and a fourth pair of resistors, $R_{P4}$, $R_{D4}$ are positioned upon the second side 310 of the beam 304 laterally spread apart. In an example beam 304, the third pair of resistors is positioned in alignment with the third lateral side axis 316 and the fourth pair or resistors is positioned in alignment with the fourth lateral side axis 318, and the first and second lateral side axes 316, 318 are equally laterally spaced apart from, and on opposite sides of, the neutral axis 319 of the second side of the beam 304. More particularly, the third pair of resistors is positioned in alignment with the third lateral side axis 316 and the fourth pair or resistors is positioned in alignment with the fourth lateral side axis 318.

In an example force sensor, proximal and distal resistors that are part of the same full-bridge are laterally aligned. Moreover, in an example force sensor, spacing between the first and second lateral side axis matches spacing between the third and fourth lateral side axes. In an example force sensor, the proximal resistors $R_{P1}$-$R_{P4}$ are positioned at matching longitudinal locations of the beam. In an example force sensor, the distal resistors $R_{D1}$-$R_{D4}$ are positioned at matching longitudinal locations of the beam.

Figure 8A:
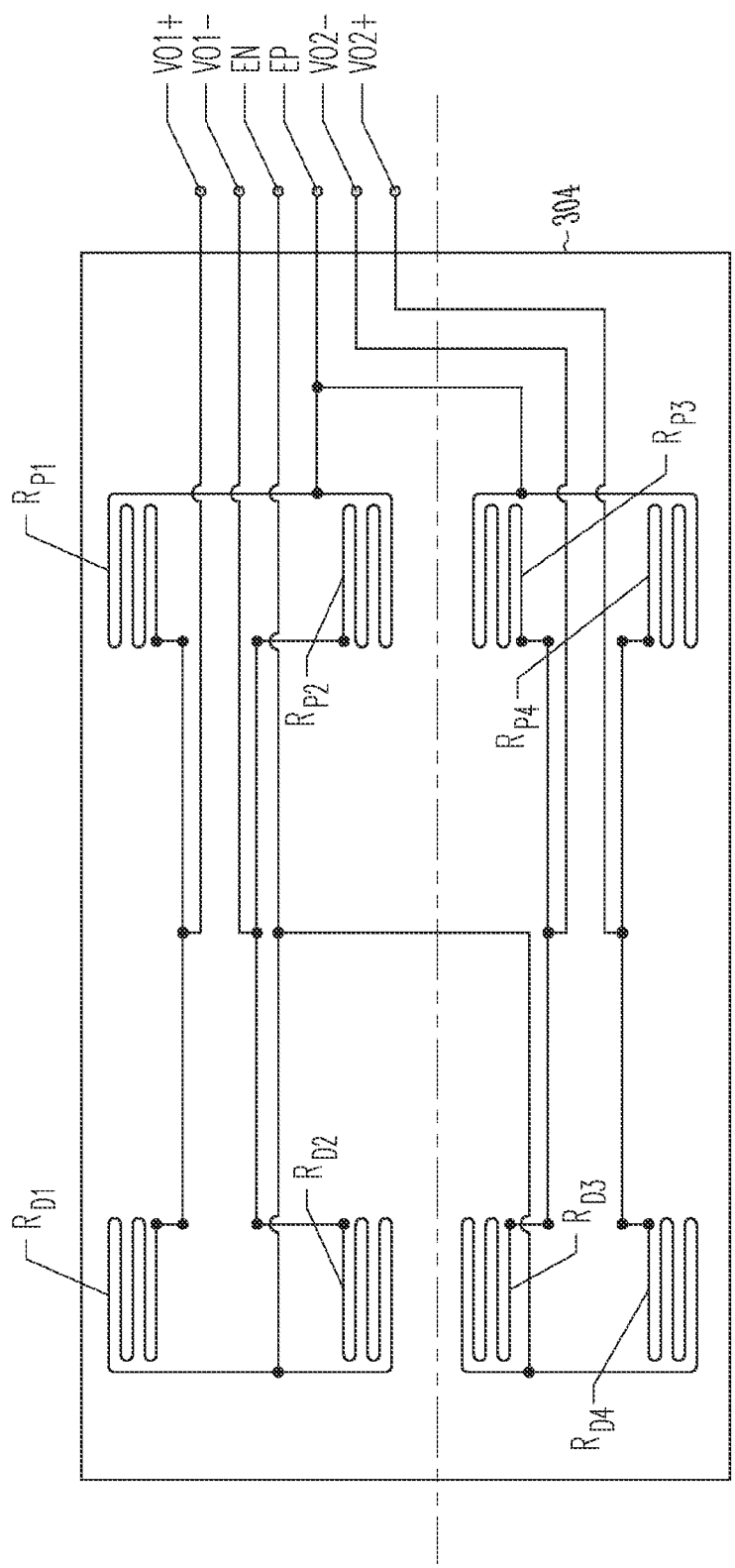
FIG. 8A is an illustrative flattened side view of two adjacent sides of an example beam showing a layout of first and second full-Wheatstone bridges and routing of center conductor traces.

As explained below, resistors of the first bridge 352 are arranged laterally separated to measure force in a first direction perpendicular to the beam center axis 306, based upon off-neutral axis forces imparted along the first and second planes P1, P2. Similarly, resistors of the second bridge 354 are arranged laterally to measure force in a second direction that is perpendicular to the beam center axis 306 and perpendicular to the first direction, based upon measuring off-axis forces imparted along the second and third planes P3, P4. As shown in FIG. 8A, lateral separation of the resistors of the first bridge 352 makes possible routing of first center conductor traces 356 parallel to the beam center axis 306 in a region of the beam 304 between proximal and distal resistors of the first bridge 352. Likewise, lateral separation of the resistors of the second bridge 352 makes possible routing of second center conductor traces 358 parallel to the beam center axis 306 in a region of the beam 304 between proximal and distal resistors of the second bridge 354.

Figure 6B:
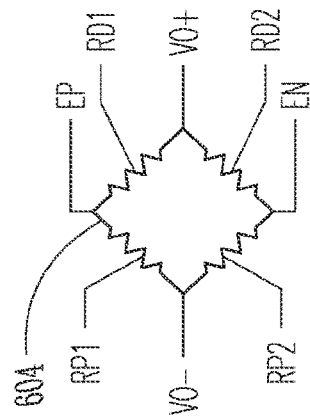
FIG. 6B is an illustrative first schematic circuit diagram representation of the full-Wheatstone bridge layout topology.
Figure 6A:
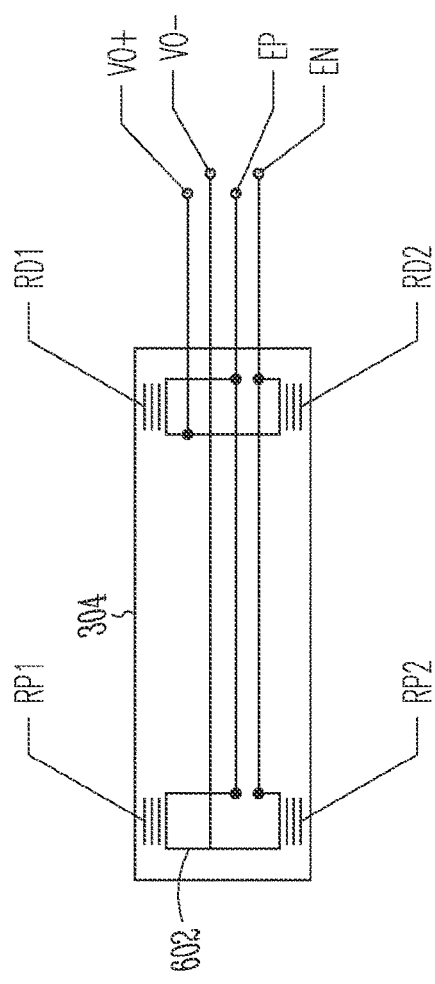
FIG. 6A is an illustrative side elevation view of an example beam showing a first example circuit layout topology of an example full-Wheatstone bridge.

FIG. 6A is an illustrative side elevation view of an example beam 304 showing an first example layout topology of an example full-Wheatstone bridge 602. The first example full-Wheatstone bridge layout includes resistors $R_{PA}$-$R_{PB}$ and $R_{DA}$-$R_{DB}$. In an example force sensor 304, the resistors $R_{P1}$-$R_{P2}$ and $R_{D1}$-$R_{D2}$ located on the first side 308 of the beam 304 can be coupled consistent with the topology of the first full-Wheatstone bridge layout, and likewise, resistors $R_{P3}$-$R_{P4}$ and $R_{D3}$-$R_{D4}$ located on the second side 310 of the beam 304 can be coupled consistent with the topology of the first full-Wheatstone bridge layout. The first Wheatstone bridge layout is coupled in a first configuration to input bias voltage conductors (EP, EN) and output voltage conductors (Vo−, Vo+). FIG. 6B is an illustrative first schematic circuit diagram 604 representation of the full-Wheatstone bridge layout topology. Referring to FIGS. 6A-6B, the first proximal resistor $R_{PA}$ is electrically coupled between a positive first DC electrical potential (EP) and a second (also referred to as 'negative' potential) output Vo−. The second proximal resistor $R_{PB}$ is electrically coupled between a negative second DC electrical potential (EN) and the second output Vo−. The first distal resistor $R_{DA}$ is electrically coupled between the positive first DC electrical potential (EP) and a first output Vo+ (also referred to as a 'positive' output). The second distal resistor $R_{DB}$ is electrically coupled between the negative second DC electrical potential (EN) and the first output Vo+.

Figure 7B:
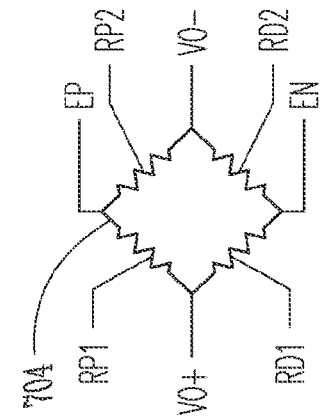
FIG. 7B is an illustrative first schematic circuit diagram representation of the second full-Wheatstone bridge layout topology.
Figure 7A:
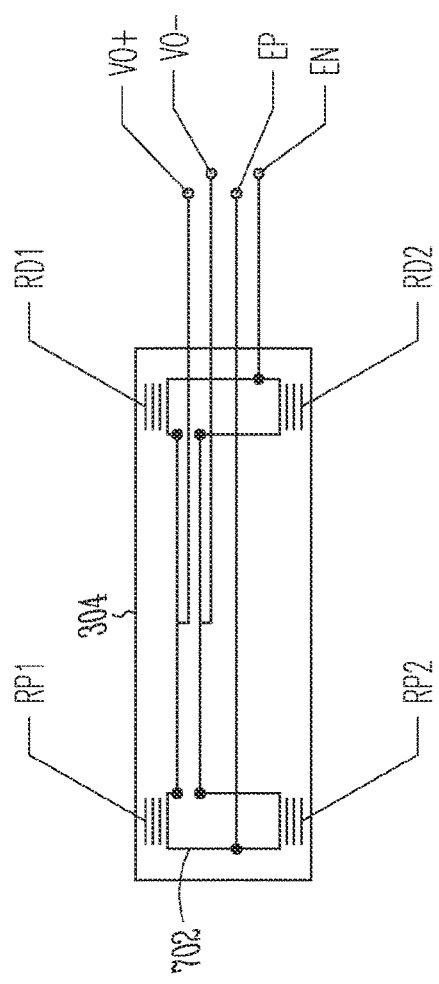
FIG. 7A is an illustrative side elevation view of an example beam showing a second example circuit layout topology of an example full-Wheatstone bridge.

FIG. 7A is an illustrative side elevation view of an example beam 304 showing a second circuit layout topology of an example full-Wheatstone bridge 702. The second example full-Wheatstone bridge layout includes resistors $R_{PA}$-$R_{PB}$ and $R_{DA}$-$R_{DB}$. In an example force sensor 304, the resistors $R_{P1}$-$R_{P2}$ and $R_{D1}$-$R_{D2}$ located on the first side 308 of the beam 304 can be coupled consistent with the topology of the second full-Wheatstone bridge layout, and likewise, resistors $R_{P3}$-$R_{P4}$ and $R_{D3}$-$R_{D4}$ located on the second side 310 of the beam 304 can be coupled consistent with the topology of the second full-Wheatstone bridge layout. The second Wheatstone bridge layout is coupled in a second configuration to input bias voltage conductors (EP, EN) and output voltage conductors (Vo−, Vo+). FIG. 7B is an illustrative first schematic circuit diagram 704 representation of the second full-Wheatstone bridge layout topology. Referring to FIGS. 7A-7B, the first proximal resistor $R_{PA}$ is electrically coupled between the positive first DC electrical potential (EP) and the first output Vo+. The second proximal resistor $R_{PB}$ is electrically coupled between the positive first DC electrical potential (EP) and the second output Vo−. The first distal resistor $R_{DA}$ is electrically coupled between the negative second DC electrical potential (EN) and the first output Vo+. The second distal resistor $R_{DB}$ is electrically coupled between the negative second DC electrical potential (EN) and the second output Vo−.

In general, the layout in FIG. 6A is better for reducing the number of traces that must span the length of the beam and also reduces the effect of traces picking up strain. On the other hand, the layout in FIG. 7A layout is preferred if the force sensor uses half bridge voltage measurements.

FIG. 8A is an illustrative flattened side view of two adjacent sides of an example beam 304 showing a spread layout of first and second full-Wheatstone bridges 352, 354 and routing of center conductor traces 356, 358 that extend within the centers of the bridges, between proximal and distal resistors of the bridges. The first bridge 352 is located at a first side 304-1 of the beam 304. The second bridge 354 is located at a second side 304-2 of the beam 304. The first and second sides 304-1, 304-2 share a side edge 303 of the beam 304.

The first full Wheatstone bridge 352 includes $R_{P1}$, $R_{P2}$ and distal resistors $R_{D1}$, $R_{D2}$ and has a first neutral axis 362 that extends parallel to the beam axis 306 between proximal resistors $R_{P1}$, $R_{P2}$ and the distal resistors $R_{D1}$, $R_{D2}$. In an example first bridge, the first neutral is equally spaced from each of $R_{P1}$ and $R_{P2}$ and is equally spaced from each of $R_{D1}$ and $R_{D2}$. The first bridge 352 is longitudinally split in that the proximal resistors $R_{P1}$, $R_{P2}$ are longitudinally separated from the distal resistors $R_{D1}$, $R_{D2}$. The first bridge is laterally spread in that proximal resistors $R_{P1}$, $R_{P2}$ are laterally spread apart and the distal resistors $R_{D1}$, $R_{D2}$ are laterally spread apart from one another. The second full Wheatstone bridge 354 has a first neutral axis 364 that extends along the outer surface of the beam 304 parallel to the beam axis 306 between proximal resistors $R_{P3}$, $R_{P4}$ and between distal resistors $R_{D3}$, $R_{D4}$. In an example second bridge, the second neutral is equally spaced from each of $R_{P3}$ and $R_{P4}$ and is equally spaced from each of $R_{D3}$ and $R_{D4}$. The second bridge 354 is longitudinally split in that the proximal resistors $R_{P3}$, $R_{P4}$ are longitudinally separated from the distal resistors $R_{D3}$, $R_{D4}$. The second bridge is laterally spread in that proximal resistors $R_{P3}$, $R_{P4}$ are laterally spread apart and the distal resistors $R_{D3}$, $R_{D4}$ are laterally spread apart from one another.

It will be appreciated that since the resistors of the first full-Wheatstone bridge 352 are laterally spread apart, they do not occupy the first neutral axis 362. Likewise, since the resistors of the second full-Wheatstone bridge 354 are laterally spread apart, they do not occupy the second neutral axis 364. Therefore conductor traces can be routed close to and in parallel with the first and second neutral axes 362, 364, which can reduce the amount of strain imparted to the traces. Also, routing of traces along the neutral axis of a bridge circuit can be easier to produce to manufacture or assembly.

An example first full-bridge includes a first group of center conductor traces 356 that extend longitudinally along a center portion of the first bridge 352, parallel to the first neutral axis 362, along a region of the outer surface 304-1 of the beam 304 between the pair of proximal resistors $R_{P1}$, $R_{P2}$ and the pair of distal resistors $R_{D1}$, $R_{D2}$ of the first bridge 352. The first group of center traces 356 include trace segments 356-1 coupled to a first positive output voltage VO1+. The first group of center traces 356 includes trace segments 356-1 coupled to a first negative voltage output VO1−. The first group of center traces 356 include trace segments 356-3 coupled to a negative voltage potential EN.

Similarly, an example second full-bridge includes a second group of center conductor traces 358 that extend longitudinally along a center portion of the second bridge 354, parallel to the second neutral axis 364, along a region of the outer surface 304-2 of the beam 304 between the pair of proximal resistors $R_{P3}$, $R_{P4}$ and the pair of distal resistors $R_{D3}$. $R_{D4}$ of the second bridge 352. The second group of center traces 358 include trace segments 358-1 coupled to a second positive output voltage VO2+. The second group of center traces 358 include trace segments 358-2 coupled to a second negative voltage output VO2−. The second group of center traces 358 include trace segments 358-3 coupled to the negative voltage potential EN.

Figure 8B:
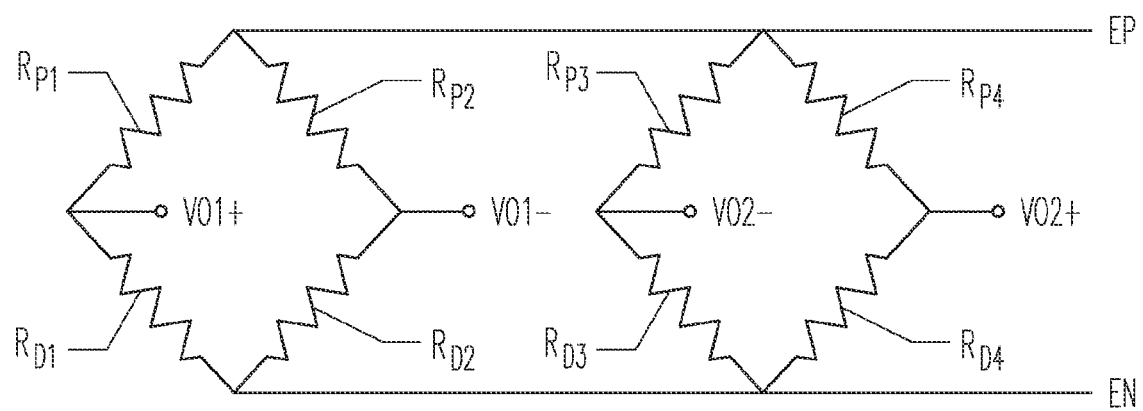
FIG. 8B is an illustrative first schematic circuit diagram representation of the first and second full-Wheatstone bridges of FIG. 8A.

FIG. 8B is an illustrative first schematic circuit diagram representation of the first and second full-Wheatstone bridges of FIG. 8A. The first full-Wheatstone bridge 352 includes $R_{P1}$ and $R_{D1}$ coupled between EP and EN to provide a first half-bridge voltage divider circuit that includes a trace conductor coupled to the first positive output voltage VO1+. The first full-Wheatstone bridge 352 also includes $R_{P2}$ and $R_{D2}$ coupled between EP and EN to provide a second half-bridge voltage divider circuit that includes a trace conductor coupled to the first negative output voltage VO1−. The second full-Wheatstone bridge 354 includes $R_{P3}$ and $R_{D3}$ coupled between EP and EN to provide a third half-bridge voltage divider circuit that includes a trace conductor coupled to the second negative output voltage VO2−. The second full-Wheatstone bridge 354 also includes $R_{P4}$ and $R_{D4}$ coupled between EP and EN to provide a fourth half-bridge voltage divider circuit that includes a trace conductor coupled to the second positive output voltage VO2+.

FIG. 9A is an illustrative cross-sectional end view of the example beam 304 of FIG. 4 indicating the resistors on the first side and indicating a first plane force FP1 and a second plane force FP2. FIG. 9B is an illustrative force diagram that indicates orthogonal X and Y force components of the first plane force FP1 imparted to the first proximal resistor $R_{P1}$ and the first distal resistor $R_{D1}$ in response to an applied force F. FIG. 9C is an illustrative force diagram that indicates X and Y force components of the second plane force FP2 imparted to the second proximal resistor $R_{P2}$ and the second distal resistor $R_{D2}$ in response to the applied force F.

In an example force sensor 302, resistance values of the first pair of resistors, $R_{P1}$, $R_{D1}$, match resistance values of the second pair of resistors, $R_{P2}$, $R_{D2}$. In an example force sensor 302, the first and second pairs of resistors are positioned upon an example beam 304, such that an applied force F imparted to the example beam 304 imparts a first plane strain force FP1 to the first pair of resistors within the first plane P1 and imparts a second plane strain force FP2 to the second pair of resistors within the second plane P2. It will be appreciated that the first plane strain force FP1 is an off-axis force since it is a force imparted along the first lateral side axis 312, which is laterally offset from a neutral axis 315 of the first bridge 352. Likewise, it will be appreciated that the second plane strain force FP2 is an off-axis force since it is a force imparted along the second lateral side axis 314, which is laterally offset from a neutral axis 315 of the first bridge 352. The first and second pairs of resistors are positioned upon an example beam 304, such that a magnitude of the components of the first plane strain force FP1 matches a magnitude of the components of the second plane strain force FP2. Force directions of the first plane strain force FP1 and second plane strain force FP2 are separated from one another by the first separation angle 'A'.

An advantage of using strain gauge resistors of the same type is that magnitude of a force imparted perpendicular to the center axis 306 of a beam 304 can be determined based upon a difference in magnitude of off-axis forces imparted to the different half-bridges of a full-bridge located on the beam. In the example force sensor 302, magnitude of a Y-direction force component $F_Y$ imparted to the beam 304 by an applied force F can be determined based upon difference between the first off-axis force FP1 and the second off-axis force FP2 as follows.

Let A be angle between P1 and P2.

Let X axis bisect the angle A. Therefore, an angle between P1 and X is A/2 and an angle between P2 and X is A/2.

Let θ be an angle between the X axis and an applied force F.

Force along X axis $F_x$=F cos θ
Force along y axis $F_y$=F sin θ
Referring to FIG. 9B, force along P1=$F_x$ cos A/2+$F_y$ cos (90+A/2)=FP1
Referring to FIG. 9C, force along P2=$F_x$ cos A/2+$F_y$ cos (90−A/2)=FP2

FP1=$F_x$ cos A/2+$F_y$ cos (90+A/2)
FP2=$F_x$ cos A/2+$F_y$ cos (90−A/2)
Using cos (θ)=−cos (180−θ)
we get
FP2=$F_x$ cos A/2−$F_y$ cos (90+A/2)
When we subtract FP1 and FP2
we get FP1−FP2=$F_x$ cos A/2+$F_y$ cos (90+A/2)−$F_x$ cos A/2+$F_y$ cos (90+A/2)
Therefore, FP1−FP2=2 $F_y$ cos (90+A/2)
Therefore, FP1−FP2∝$F_y$ Thus, the difference between FP1 and FP2 is proportional to the Y-direction force component $F_Y$ imparted to the beam by the applied force F.

Moreover, it will be appreciated that,
$F_Y \alpha V_{S1O+}-V_{S1O-}$,
where $V_{S1O+}$ is positive output voltage and $V_{S1O-}$ is negative output voltage of the first bridge circuit 352, and $V_{S1O+}-V_{S1O-}$ is a voltage offset produced by the first bridge circuit 352 located on the first side 308 of the beam 304.

Figure 10:
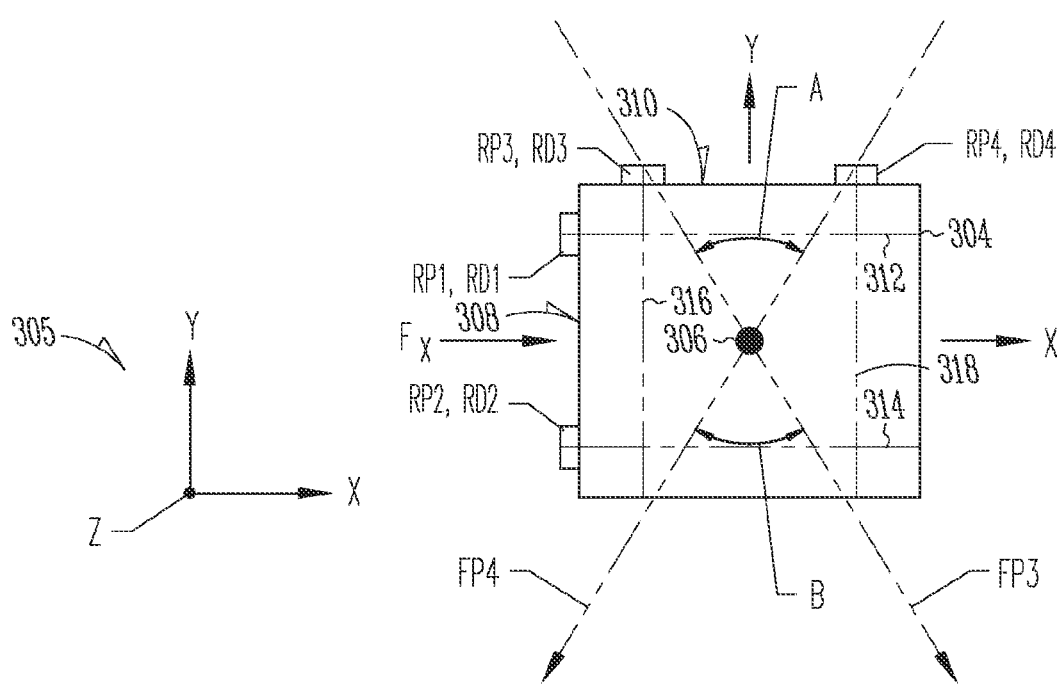
FIG. 10 is an illustrative cross-sectional end view of the example beam of FIG. 4 indicating the resistors on the second side of the beam and indicating third plane force and fourth plane force.

FIG. 10 is an illustrative cross-sectional end view of the example beam of FIG. 4 indicating the resistors on the second side 310 of the beam 304 and indicating third plane X-force and fourth plane X-force. In an example force sensor 302, resistance values of the third pair of resistors, $R_{P3}$, $R_{D3}$, match resistance values of the fourth pair of resistors, $R_{P4}$, $R_{D4}$. In an example force sensor 302, the third and fourth pairs of resistors are positioned upon an example beam 304, such that an applied force imparted to the example beam 304 imparts a third plane strain force FP3 to the third pair of resistors within the third plane P3 and imparts a fourth plane strain force FP4 to the fourth pair of resistors within the fourth plane P4. It will be appreciated that the third plane strain force FP3 is an off-axis force since it is a force imparted along the third lateral side axis 316, which is laterally offset from a neutral axis 315 of the second bridge 354. Likewise, it will be appreciated that the fourth plane strain force FP4 is an off-axis force since it is a force imparted along the fourth lateral side axis 318, which laterally is offset from a neutral axis 315 of the second bridge 354. The third and fourth pairs of resistors are positioned upon an example beam 304, such that a magnitude of the components of third plane strain force FP3 matches a magnitude of the components of fourth plane strain force FP4. Force directions of the third plane strain force FP3 and the fourth plane strain force FP4 are separated from one another by the second separation angle A.

In this example, the difference between FP3 and FP4 is proportional to the X-direction force component $F_x$ imparted to the beam by the applied force F. Persons skilled in the art will understand the process for determining the difference between FP3 and FP4 based upon the above explanation of a determination of a difference between FP1 and FP2.

Moreover, it will be appreciated that,
$F_X$=FP3−FP4
$F_X \alpha V_{S2O+}-V_{S2O-}$,
where $V_{S2O+}$ is the positive output voltage and $V_{S2O-}$ is the negative output voltage of the second bridge 354 and $V_{S2O+}-V_{S2O-}$ is a voltage offset produced by the second bridge circuit 354 on the second side 310 of the beam 304.

Figure 11:
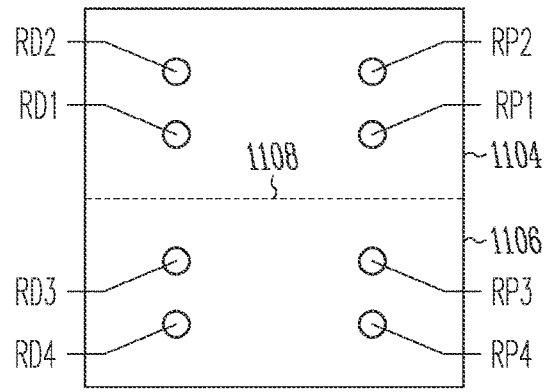
FIG. 11 is an illustrative drawing representing a metal sheet containing cut-outs that define example resistors for assembly into respective bridge circuits on adjacent first and second sides of the beam.

FIG. 11 is an illustrative drawing representing a metal sheet 1102 containing cut-outs that define example resistors $R_{P1}$-$R_{P4}$ and $R_{D1}$-$R_{D4}$ for assembly into respective first and second full-Wheatstone bridges on adjacent first and second sides 308, 310 of the beam 304. A first region 1104 of the metal sheet 1102 includes resistors $R_{P1}$-$R_{P2}$ and $R_{D1}$-$R_{D2}$ for coupling in a first full-bridge configuration located on the first side 308 of the beam 304. A second region 1106 of the metal sheet 1102 includes resistors $R_{P3}$-$R_{P4}$ and $R_{D3}$-$R_{D4}$ for coupling in a second full-bridge configuration located on the second (Y-axis) side of an example beam. The first and second region are separated by a fold line 1108.

Figure 12A:
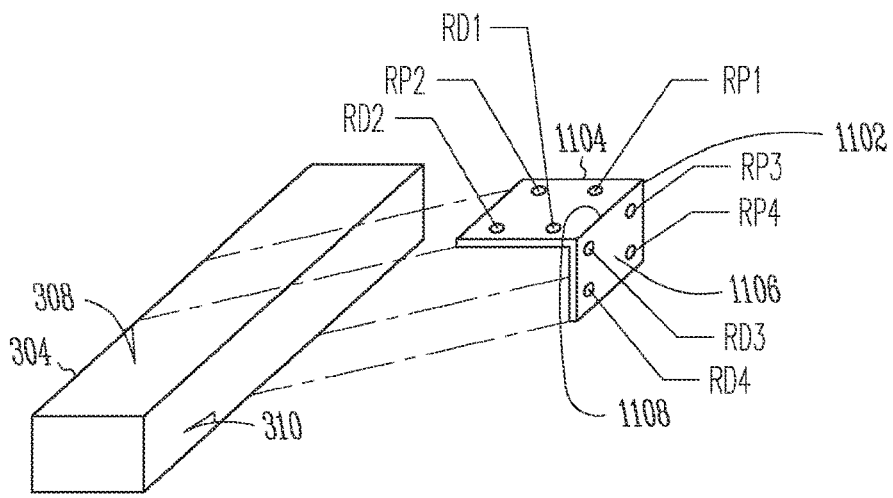
FIG. 12A is an illustrative drawing representing a process of wrapping first and second regions about first and second sides of the metal sheet about a beam.
Figure 12B:
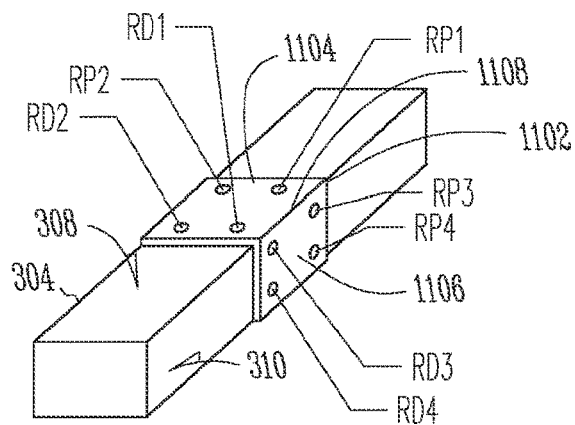
FIG. 12B is an illustrative perspective view of the beam showing the first and second regions of the metal sheet overlaying respective first and second sides of an example beam.

FIG. 12A is an illustrative drawing representing a process of folding the metal sheet 1102 at the fold line 1108 to wrap the first and second regions of the metal sheet about a beam 304 to position first pair of resistors $R_{P1}$-$R_{P2}$ and $R_{D1}$-$R_{D2}$ at the side 308 of the beam 304 and to position the second pair of resistors $R_{P3}$-$R_{P4}$ and $R_{D3}$-$R_{D4}$ at the second side 310 of the beam 304. FIG. 12B is an illustrative perspective view of the beam 304 showing the first and second regions 1104-1106 of the metal sheet 1102 overlaying respective first and second sides 308-310 of an example beam 304. In an example rectangular beam, the first and second sides include adjacent side faces of the beam. The metal sheet 1102 can be glued on or welded on to the beam 304 or a combination of both. During the attachment process caution is taken to line up the metal sheet 1102 with the beam 304.

Redundant Multiple Half-Bridge XY Force Sensor

In a sensor having four half-bridges and all gauges of same type on first and reverse sides, subtracting the half bridge voltages of adjacent two half bridges provides a force measurement in the axis parallel to the plane having all the gauges of the two half bridge. There are four ways to do this which provides two measurements of Fx and Fy.

Figure 13A:
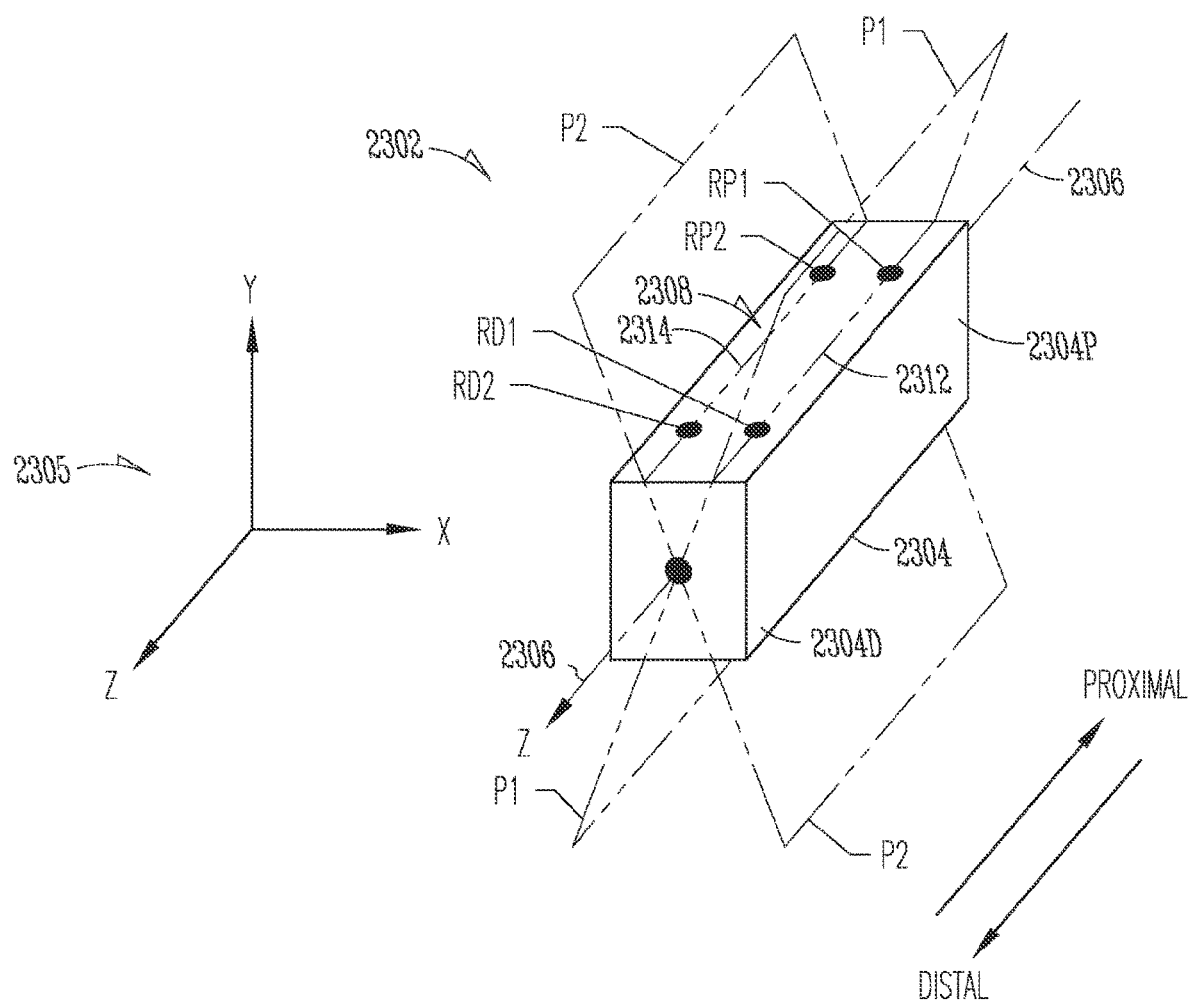
FIG. 13A-13B show an illustrative top perspective view (FIG. 13A) and bottom perspective view (FIG. 13B) of an example force sensor that includes a rectangular beam with two four strain gauge resistors coupled in two half Wheatstone bridge circuits located on each of two reverse sides thereof.
Figure 13B:
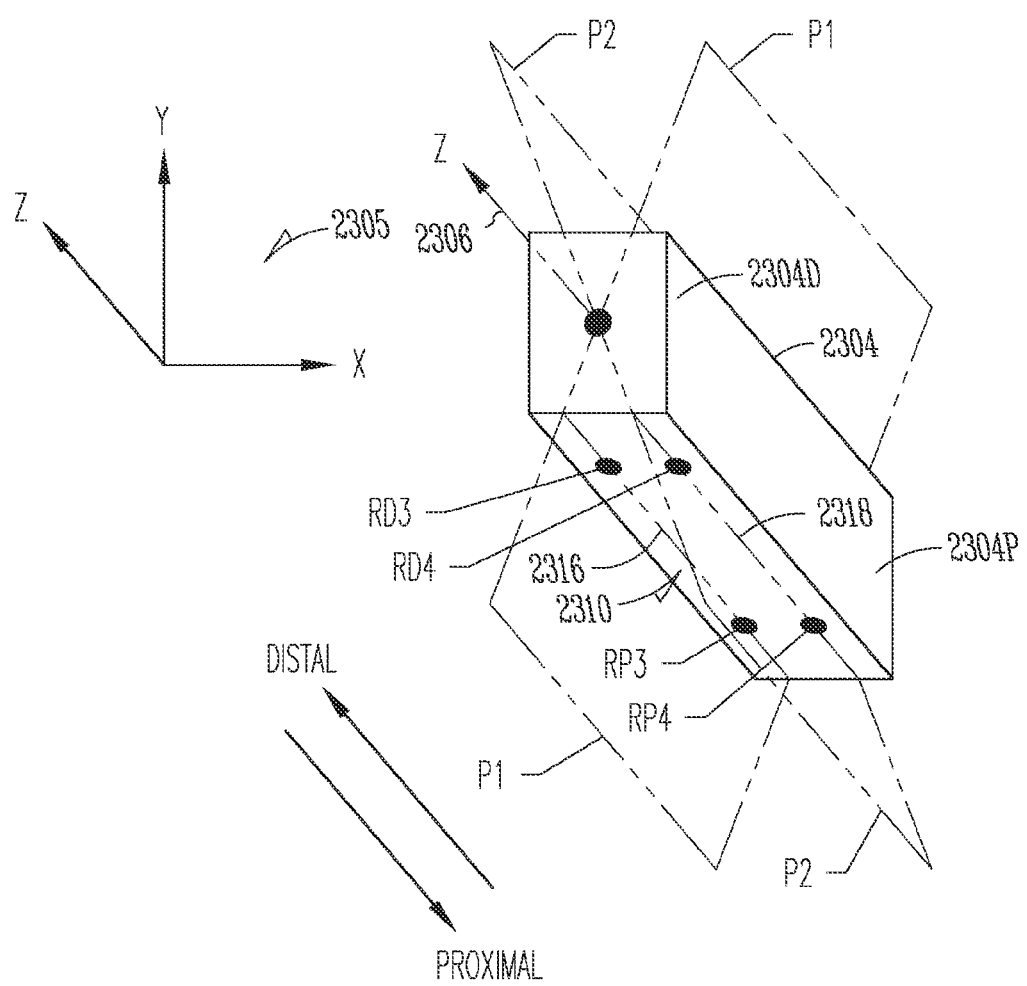

FIG. 13A-13B show an illustrative first side perspective view (FIG. 13A) and second side perspective view (FIG. 13B) of an example force sensor 2302 that includes a rectangular beam 2304 with two four strain gauge resistors $R_{P1}$-$R_{P4}$, $R_{D1}$-$R_{D4}$ coupled in two half Wheatstone bridge circuits ('half-bridges") located on each of two reverse sides thereof. A second side 308 of the beam 2304 shown in FIG. 13B faces in a direction that is reverse of a direction faced by a first side 308 of the beam 2304 shown in FIG. 13A. An (X, Y, Z) beam coordinate system 2305 is provided to explain force directions relative to the beam 2304. An example beam 2304 can have a rectangular cross-section with planar side faces. More particularly, an example beam can have a square cross-section. The beam 2304 includes a proximal beam portion 2304P and a distal beam portion 2304D and includes a longitudinal center axis 306 extending between the proximal and distal beam portions 2304P, 2304D.

Referring to FIG. 13A, a first proximal strain gauge resistor ('resistor') $R_{P1}$ and a second proximal resistor $R_{P2}$ are located at the proximal beam portion 2304P of the first side 308 of the beam 2304. A first distal resistor $R_{D1}$ and a second distal resistor $R_{D2}$ are located at the distal beam portion 2304D of the first side 308 of the beam 2304. As explained below with reference to FIGS. 14A-14B, 15A-15B, a first pair of resistors, $R_{P1}$-$R_{D1}$, are electrically coupled in series and arranged in a first half-bridge, and a second pair of resistors, $R_{P2}$-$R_{D2}$, are electrically coupled in series and arranged in a second half-bridge.

Referring to FIG. 13B, a third proximal resistor $R_{P3}$ and a fourth proximal resistor $R_{P4}$ are located at the proximal beam portion 2304P of the second side 2310 (also referred to as the 'reverse' side) of the beam 2304 that faces in a reverse direction to a direction faced by the first side 308 of the beam 2304. A third distal resistor $R_{D3}$ and a fourth distal resistor $R_{D4}$ are located at a distal beam portion 2304D of the reverse second side 2310 of the beam 2304. As explained below with reference to FIGS. 14A-14B, 15A-15B, a third pair of resistors, $R_{P3}$-$R_{D3}$, are electrically coupled in series and arranged in a third half-bridge, and a fourth pair of resistors, $R_{P4}$-$R_{D4}$, are electrically coupled in series and arranged in a fourth half-bridge arranged in a fourth half-bridge.

Figure 14A:
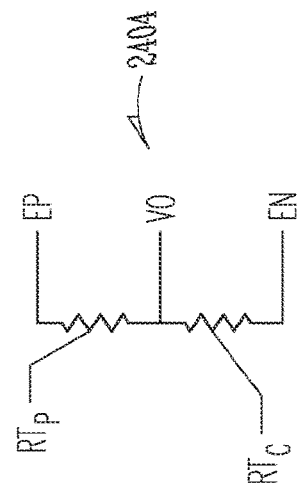
FIG. 14A shows an illustrative first example half-bridge circuit layout having proximal and distal tension gauge strain resistors electrically coupled in series and having a voltage node coupled between them.
Figure 14B:
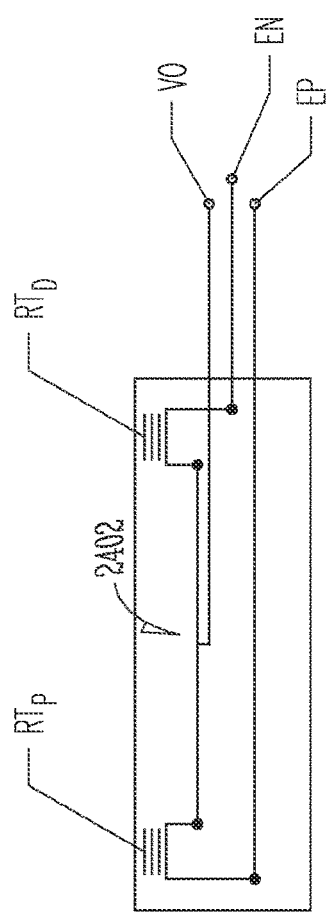
FIG. 14B is an illustrative first schematic circuit diagram representation of the first half-bridge circuit layout.

FIG. 14A is an illustrative side view of an example beam including a first example half-bridge circuit layout 2402 having proximal and distal tension gauge strain resistors $RT_P$, $RT_D$ electrically coupled in series and having a voltage node coupled between them. The first example half-bridge bridge circuit layout 2402 includes input bias voltage conductors (EP, EN) and output an voltage node (Vo) between the proximal and distal tension resistors $RT_P$, $RT_D$. FIG. 14B is an illustrative first schematic circuit diagram 2404 representation of the first half-bridge circuit layout 2402. Referring to FIGS. 14A-14B, a proximal tension resistor $RT_P$ is electrically coupled between a positive first DC electrical potential (EP) and an output voltage node Vo. A distal tension resistor $RT_D$ is electrically coupled between a negative second DC electrical potential (EN) and the output voltage node Vo. In an example force sensor 2302, each of the first, second, third and fourth half-bridges has a layout 2402 and circuit schematic 2404 represented in FIGS. 14A-14B.

Figure 15A:
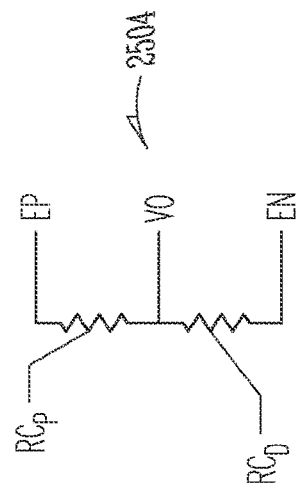
FIG. 15A shows an illustrative second example half-bridge circuit layout having proximal and distal compression gauge strain resistors electrically coupled in series and having a voltage node coupled between them.
Figure 15B:
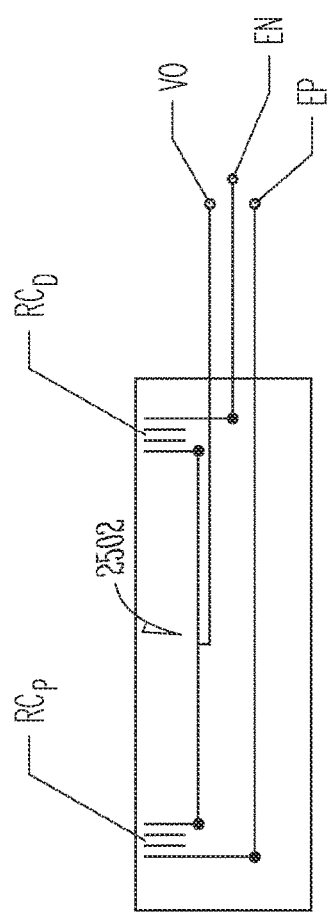
FIG. 15B is an illustrative second schematic circuit diagram representation of the second half-bridge circuit layout.

FIG. 15A is an illustrative side view of an example beam showing a second example half-bridge circuit layout 2502 having proximal and distal compression gauge strain resistors $RC_P$, $RC_D$ electrically coupled in series and having a voltage node coupled between them. The second example half-bridge bridge circuit layout 2502 includes input bias voltage conductors (EP, EN) and output an voltage node (Vo) between the proximal and distal compression resistors RCP, RCD. FIG. 15B is an illustrative second schematic circuit diagram 2504 representation of the second half-bridge circuit layout 2502. Referring to FIGS. 15A-15B, a proximal compression resistor $RC_P$ is electrically coupled between a positive first DC electrical potential (EP) and an output voltage node Vo. A distal compression resistor $RC_D$ is electrically coupled between a negative second DC electrical potential (EN) and the output voltage node Vo. In another example force sensor 2302, each of the first, second, third and fourth half-bridges has a layout 2502 and circuit schematic 2504 represented in FIGS. 15A-15B.

As shown in FIGS. 14A-14B and FIGS. 15A-15B, each half-bridge of an example force sensor 2302 includes a pair of strain gauge resistors having matching type, which can be either tension type (FIGS. 14A-14B) or compression type (FIGS. 15A-15B). As used herein reference to a set resistors having 'matching type' refers to a set of resistors in which either all resistors are tension resistors or all resistors are compression resistors. Although either tension or compression gauge resistors can be used to determine X direction and Y direction forces, in general, tension strain gauge resistors are more sensitive than compression gauge resistors.

Referring again to FIGS. 13A-13B, as explained more fully below, a voltage offset between a first half-bridge voltage at a first voltage node between the first pair of resistors $R_{P1}$, $R_{D1}$ and a second half-bridge voltage at a second voltage node between the second pair of resistors $R_{P2}$, $R_{D2}$ can be used to measure X-direction force imparted to the beam 2304. Additionally, a voltage offset between the third half-bridge voltage at a third voltage node between the third pair of resistors $R_{P3}$, $R_{D3}$ and a fourth half-bridge voltage at a fourth voltage node between the fourth pair of resistors $R_{P4}$, $R_{D4}$ can be used to measure X-direction force imparted to the beam 2304. Thus, together, the first, second, third, and fourth half-bridges provide redundant measures of X-direction force upon the beam.

Further, as explained more fully below, a voltage offset between the first half-bridge voltage at a first voltage node between the first pair of resistors $R_{P1}$, $R_{D1}$ and the fourth half-bridge voltage at the fourth voltage node between the fourth pair of resistors $R_{P4}$, $R_{D4}$ can be used to measure Y-direction force imparted to the beam 2304. Additionally, an offset between the second half-bridge voltage at the second voltage node between the second pair of resistors $R_{P2}$, $R_{D2}$ and the third half-bridge voltage at the third voltage node between the third pair of resistors $R_{P3}$, $R_{D3}$ can be used to measure Y-direction force imparted to the beam 2304.

Thus, together, the first, second, third, and fourth half-bridges can provide redundant measures of X-direction force upon the beam 2304 and can provide redundant measures of Y-direction forces upon the beam 2304. A malfunction of any one of resistors $R_{P1}$-$R_{P4}$ and $R_{D1}$-$R_{D4}$ results in differences in X-direction force measurements determined using the first and second half-bridges on the one hand and X-direction force determined measurements using the third and fourth half-bridges on the other. Similarly, a malfunction of any one of resistors $R_{P1}$-$R_{P4}$ and $R_{D1}$-$R_{D4}$ results in differences in Y-direction force measurements determined using the first and fourth half-bridges on the one hand and Y-direction force measurements determined using the second and third half-bridges on the other.

Still referring to FIG. 13A, the first proximal resistor $R_{P1}$ and the first distal resistor $R_{D1}$ are arranged upon the first side 308 of the beam 2304 within a first imaginary plane P1 in which the center axis 306 extends and that defines a first lateral side axis 2312 at a location on the first side 308 of the beam 2304 along which the first plane P1 intersects the first side 308. The first lateral side axis 2312 and the center axis 306 extend parallel to one another. An example first lateral side axis 2312 extends through the first proximal resistor $R_{P1}$ and through the first distal resistor $R_{D1}$. More particularly in an example force sensor, the example first lateral side axis 2312 bisects the example first proximal resistor $R_{P1}$ and bisects the example first distal resistor $R_{D1}$.

Referring to FIG. 13A, the second proximal resistor $R_{P2}$ and the second distal resistor $R_{D2}$ are arranged upon the first side 308 of the beam within a second imaginary plane P2 in which the center axis 306 extends and that defines a second lateral side axis 2314 at a location on the first side 308 of the beam 2304 along which the second plane P2 intersects the first side. The second lateral axis 2314 and the center axis 306 extend parallel to one another. An example second lateral side axis 2314 extends through the second proximal resistor $R_{P2}$ and through the second distal resistor $R_{D2}$. More particularly in an example force sensor, the example second lateral side axis bisects 2314 the example second proximal resistor $R_{P2}$ and bisects an example second distal resistor $R_{D2}$.

Referring to FIG. 13B, the third proximal resistor $R_{P3}$ and the third distal resistor $R_{D3}$ are arranged upon the reverse second side 2310 of the beam 2304 within the first imaginary plane P1, in which the center axis extends 306, and that defines a third lateral side axis 2316 at a location on the second side 2310 of the beam 2304 along which the first plane P1 intersects the second side 2310. An example third lateral side axis 2316 extends through the third proximal resistor $R_{P3}$ and through the third distal resistor $R_{D3}$. More particularly in an example force sensor, the example third side axis 2316 bisects the example third proximal resistor $R_{P3}$ and bisects an example third distal resistor $R_{D3}$.

Referring to FIG. 13B, the fourth proximal resistor $R_{P4}$ and the fourth distal resistor $R_{D4}$ are arranged upon the reverse second side 2310 of the beam 2304 within the second imaginary plane P2, in which the center axis 306 extends, and that defines a fourth lateral side axis 2318 at a location on the second side 2310 of the beam 2304 along which the second plane P2 intersects the second side 2310 of the beam 2304 and that includes the center axis 306. An example fourth lateral side axis 2318 extends through the fourth proximal resistor $R_{P4}$ and through the fourth distal resistor $R_{D4}$. More particularly in an example force sensor, the example fourth lateral side axis bisects an example fourth proximal resistor $R_{P4}$ and bisects an example first distal resistor $R_{D4}$.

Figure 16:
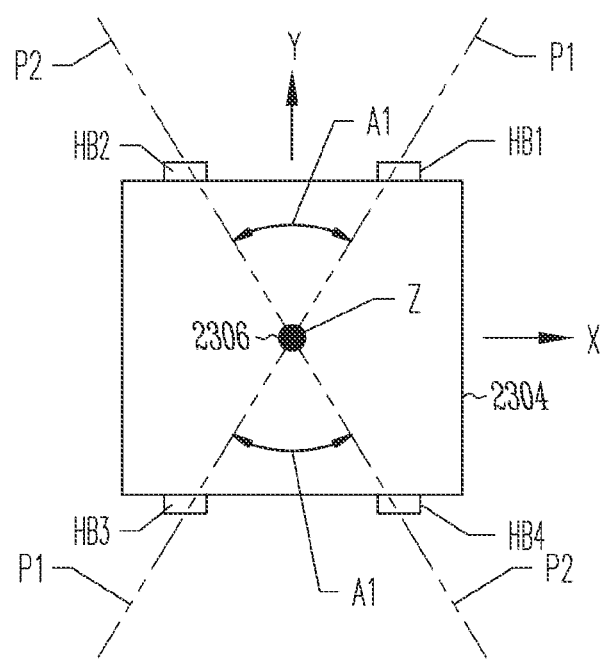
FIG. 16 is an illustrative proximal direction cross-section view of the example beam of FIGS. 13A-13B showing the first and second imaginary planes.
Figure 17B:
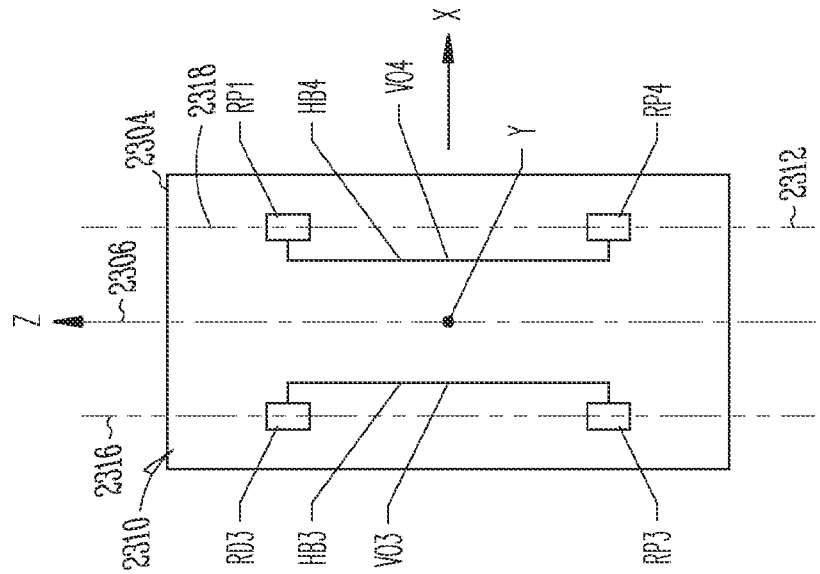
FIG. 17B is a side view of the beam showing a reverse second side of the beam of FIGS. 13A-13B.
Figure 17A:
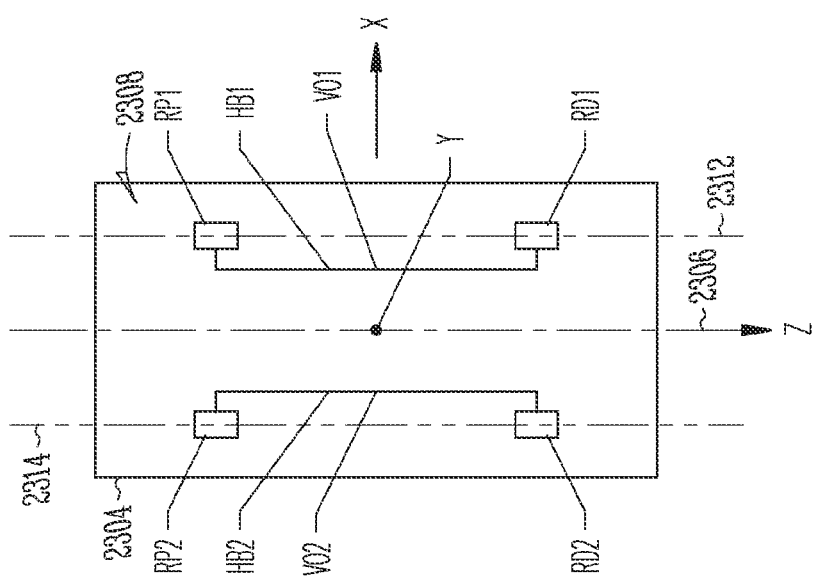
FIG. 17A is a side view of the beam showing a first side of the beam of FIGS. 13A-13B.

FIG. 16 is an illustrative proximal direction cross-section view of the example beam 2304 of FIGS. 13A-13B showing the first and second imaginary planes P1, P2. FIG. 17A is a side view of the beam 2304 showing the first side 308 of the beam of FIGS. 13A-13B, which includes first ($R_{P1}$) and second ($R_{D1}$) and second resistors coupled in a first half-bridge HB1 and includes third ($R_{P2}$) and fourth ($R_{D2}$) resistors coupled in a second half-bridge HB2. FIG. 17B is a side view of the beam 2304 showing the reverse second side 308 of the beam of FIGS. 13A-13B, which includes A second bridge includes fifth ($R_{P3}$) and sixth ($R_{D3}$) resistors coupled in a third half-bridge HB3 and includes seventh ($R_{P4}$) and eighth ($R_{D4}$) resistors coupled in a fourth half-bridge HB4.

The resistors can be placed on the beam 2304 manually or using automated machinery and can be adhered to the beam using an adhesive such as epoxy. Alternatively, the resistors can be deposited and laser etched directly on to the beam 2304. In both cases, an electrical circuit can be completed externally using wirebonds and flexible printed circuit.

Referring to FIG. 16, a proximal direction end view of the beam 2304 shows side views of the first and second planes P1, P2 that intersect one another along the center axis 306, which extends within both the first and second planes. The first plane P1 extends through the first and third half-bridges HB1, HB3 and through the center axis 306. The second plane P1 extends through the second and fourth half bridges HB2, HB4 and through the center axis 306. Portions of the first and second planes P1, P2 that extend through the respective first and second half bridges HB1, HB2 intersect the center axis 306 separated by a first separation angle A1. Portions of the first and second planes P1, P2 that extend through the respective third and fourth half bridges HB3, HB4 also intersect the center axis 306 separated by the first separation angle A1.

Referring to FIG. 17A, the first plane P1 is shown extending through the first half bridge HB1, which includes the first (proximal resistor $R_{P1}$ and the first distal resistor $R_{D1}$, which are arranged along the first lateral side axis 2312 on the first side 308 of the beam 2304, and the second plane P2 is shown extending through the second half-bridge HB2, which includes the second proximal resistor $R_{P2}$ and the second distal resistor $R_{D2}$, which are arranged along the second lateral side axis 2314 on the first side 308 of the beam 2304. Size of the first separation angle A1 corresponds to lateral spacing distance at the first side 308, between the first and second lateral side axes 2312, 2314, and therefore, corresponds to lateral spacing between the first half-bridge HB1 including the first proximal and distal resistors $R_{P1}$, $R_{D1}$ and a second resistor pair including the second proximal and distal resistors $R_{P2}$, $R_{D2}$. In an example force sensor 2302, the first lateral side axis 2312 and the second lateral side axis 2314 are equidistant from a neutral axis of the first side of the beam 2304, which is equidistant from the first and second lateral side edges 2312, 2314 of the first side 308 of the beam 2304.

Referring to FIG. 17B, the first plane P1 is shown extending through the third half bridge HB3, which includes the third proximal resistor $R_{P3}$ and the third distal resistor $R_{D3}$, which are arranged along the third lateral side axis 2316 on the second side 2310 of the beam 2304, and the second plane P2 is shown extending through the fourth half bridge HB4, which includes the fourth proximal resistor $R_{P4}$ and the fourth distal resistor $R_{D4}$, which are arranged along the fourth lateral side axis 2318 on the second side 2310 of the beam 2304. Size of the first separation angle A1 corresponds to lateral spacing distance at the second side 2310 of the beam 2304, between the third and fourth lateral side axes 2316-2318, and therefore, corresponds to lateral spacing between the third half-bridge HB3 including the third resistor pair including $R_{P3}$, $R_{D3}$, and the fourth half-bridge HB4 including the fourth resistor pair including $R_{P4}$, $R_{D4}$. In an example force sensor the third lateral side axis 2316 and the fourth lateral side axis 2318 are equidistant from a neutral axis of the second side 2310 of the beam 2304, which is equidistant from the third and fourth lateral side edges 2316, 2318 of the second side 2310 of the beam 2304.

The half-bridges HB1-HB4 are laterally located symmetrically about the beam 2304. separation angle A1 between the first and second half-bridges matches the first separation angle A1 between the third and fourth half-bridges HB3-HB4. Moreover, in an example force sensor 2302, spacing between the first and second lateral side axes 2312, 2314 matches spacing between the third and fourth lateral side axes 2316, 2318, although equidistant spacing is not required. The half-bridges HB1-HB4 are longitudinally located symmetrically along the beam 2304. Proximal resistors $R_{P1}$-$R_{P4}$ are positioned at matching longitudinal locations of the beam. In an example force sensor, the distal resistors $R_{D1}$-$R_{D4}$ are positioned at matching longitudinal locations of the beam.

Figure 18A:
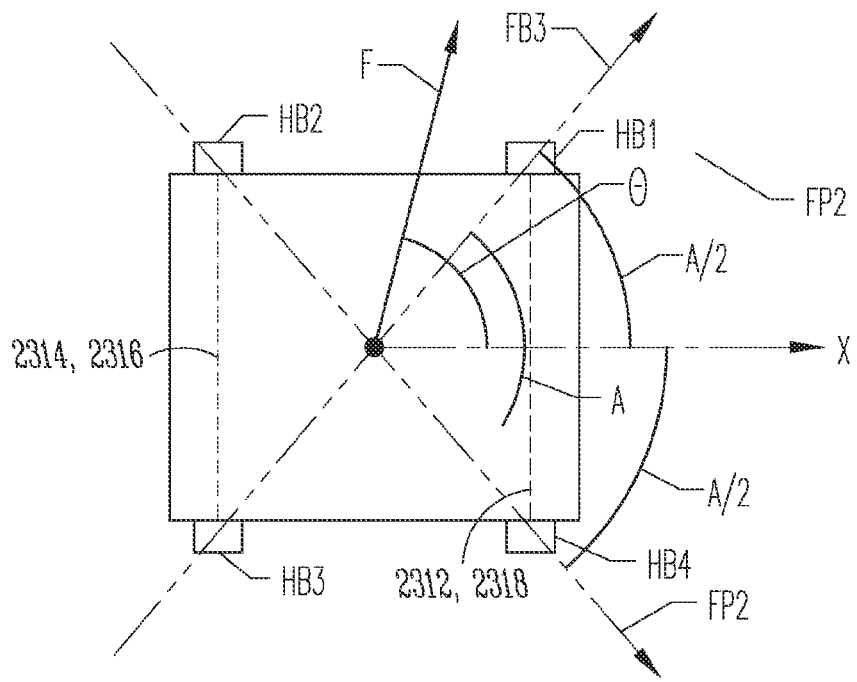
FIG. 18A is an illustrative proximal direction cross-section view of the example beam indicating a second plane strain force and a third plane strain force imparted to second and third half-bridges.
Figure 18B:
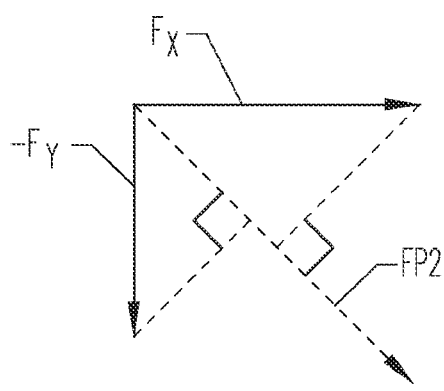
FIG. 18B is an illustrative force diagram that indicates X and Y force components of the second plane strain force to the second half-bridge.
Figure 18C:
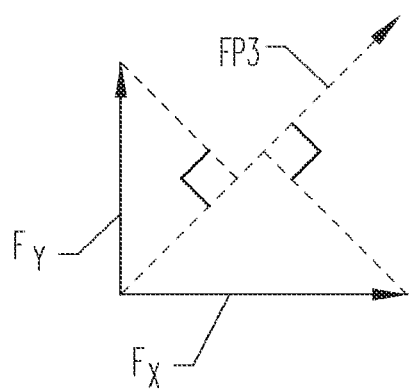
FIG. 18C is an illustrative force diagram that indicates X and Y force components of the third plane strain force imparted to the third half-bridge.

FIG. 18A is an illustrative proximal direction cross-section view of the example beam 2304 of FIGS. 13A-13B indicating a second plane strain force FP2 and a third plane strain force FP3 imparted to the respective second and third half-bridges HB2, HB3 by an applied force F upon the beam 2304. In the example beam of FIG. 18A, the second and third half-bridges HB2, HB3 contain only tension resistors. FIG. 18B is an illustrative force diagram that indicates X and Y force components of the second plane strain force FP2 imparted to the second half-bridge HB2 that includes the second proximal resistor $R_{P2}$ and the second distal resistor $R_{D2}$, in response to the applied force F. FIG. 18C is an illustrative force diagram that indicates orthogonal X and Y force components of the third plane strain force FP3 imparted to the third half-bridge HB3, which includes the third proximal resistor $R_{P3}$ and the third distal resistor $R_{D3}$, in response to the applied force.

In an example force sensor 2302, resistance values of the second pair of resistors, $R_{P2}$, $R_{D2}$, of the second half-bridge HB2 match resistance values of the third pair of resistors, $R_{P3}$, $R_{D3}$, of the third half-bridge HB3. In an example force sensor 2302, the second and third half-bridges HB2, HB3 are positioned upon an example beam 2304, such that an applied force imparted to the example beam 2304 imparts a second plane strain force FP2 to the second half-bridge HB2 within the second plane P2 and imparts a third plane strain force FP3 to the third half-bridge HB3 within the third plane P3. It will be appreciated that the second plane strain force FP2 is an off-axis force since it is a force imparted along the second lateral side axis 2314. Likewise, it will be appreciated that the third plane strain force FP3 is an off-axis force since it is a force imparted along the third lateral side axis 2316. In an example force sensor 2302, the second and third half-bridges HB2, HB3 are positioned upon an example beam 2304, such that a magnitude of the components of second plane strain force FP2 matches magnitude of the components of third plane strain force FP3.

An advantage of using strain gauge resistors of the same type is that magnitude of a force imparted perpendicular to the center axis 306 of a beam 2304 can be determined based upon a difference in magnitude of off-axis forces imparted to the different half-bridges of a full-bridge located on the beam. In the the example force sensor 2302, magnitude of a Y-direction force component $F_Y$ imparted to the beam 2304 by an applied force F can be determined based upon difference between the first off-axis force FP2 and the second off-axis force FP3 as follows.

Let A be angle between P2 and P3.

Let X axis bisect the angle A. Therefore, an angle between P2 and X is A/2 and an angle between P3 and X is A/2.

Let $\theta$ be an angle between the X axis and an applied force F.

Force along X axis $F_x = F \cos \theta$

Force along y axis $F_y = F \sin \theta$

Referring to FIG. 18B, force along P2=$F_x \cos A/2 + F_y \cos (90+A/2)$=FP2

Referring to FIG. 18C, force along P3=$F_x \cos A/2 + F_y \cos (90-A/2)$=FP3

FP2=$F_x \cos A/2 + F_y \cos (90+A/2)$

FP3=$F_x \cos A/2 + F_y \cos (90-A/2)$

Using $\cos (\theta) = -\cos (180-\theta)$ we get

FP3=$Fr \cos A/2 - F_y \cos (90+A/2)$

When we subtract FP1 and FP2 we get FP2-FP3=$F_x \cos A/2 + F_y \cos (90+A/2) - F_x \cos A/2 + F_y \cos (90+A/2)$ Therefore, FP2-FP2=2 $F_y \cos (90+A/2)$ Therefore, FP2-FP3 $\propto F_y$ Thus, the difference between FP2 and FP3 is proportional to the Y-direction force component $F_Y$ imparted to the beam by the applied force F.

Moreover, it will be appreciated that, $F_Y$=FP2-FP2

$F_Y \alpha V_{O2} - V_{O3}$ where $V_{O2}$ the output voltage of HB2 and $V_{O3}$ is the output voltage of HB3.

Figure 19:
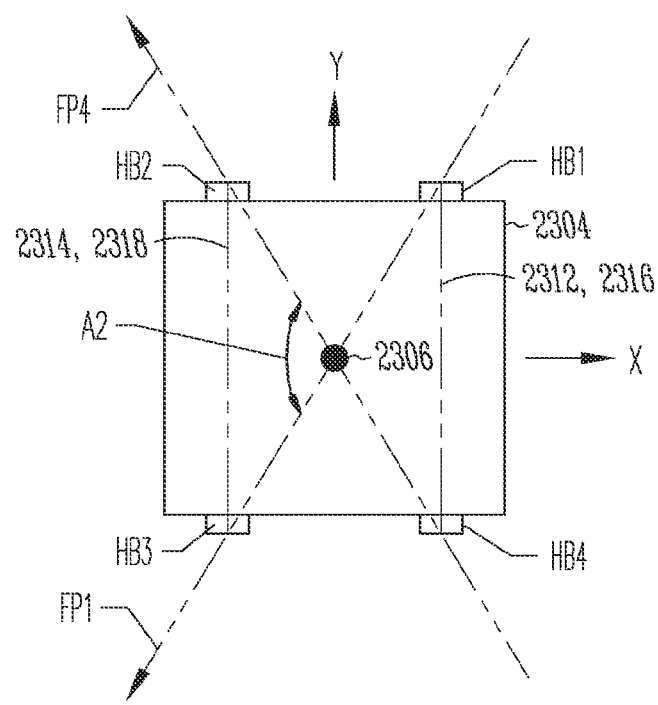
FIG. 19 is an illustrative proximal direction cross-section view of the example beam indicating a first plane strain force and a fourth plane strain force imparted to first and fourth half-bridges.

FIG. 19 is an illustrative proximal direction cross-section view of the example beam of FIGS. 13A-13B indicating a first plane strain force FP1 and a fourth plane strain force FP4 imparted to the respective first and fourth half-bridges HB1, HB4 by an applied force F upon the beam 2304. In the example beam of FIG. 19, the first and fourth half-bridges HB1, HB4 contain only tension resistors resistors. In an example force sensor 2302, resistance values of the first pair of resistors, $R_{P1}$, $R_{D1}$, of the first half-bridge HB1 match resistance values of the fourth pair of resistors, $R_{P4}$, $R_{D4}$, of the fourth half-bridge HB4. In an example force sensor 2302, the first and fourth half-bridges HB1, HB4 are positioned upon an example beam 2304, such that an applied force F imparted to the example beam 2304 imparts a first plane strain force FP1 to the first half-bridge HB1 within the first plane P1 and imparts a fourth plane strain force FP4 to the fourth half-bridge HB4 within the second plane P4. In an example force sensor 2302, the first and fourth half-bridges HB1, HB4 are positioned upon an example beam 2304, such that a magnitude of components of the first plane strain force FP1 matches a magnitude of components of the fourth plane strain force FP4.

In this example, the difference between FP1 and FP4 is proportional to the Y-direction force component $F_Y$ imparted to the beam by the applied force F. Persons skilled in the art will understand the process for determining the difference between FP1 and FP4 based upon the above explanation of a determination of a difference between FP2 and FP3.

Moreover, it will be appreciated that, $F_Y$=FP1-FP4

$F_Y \alpha V_{O1} - V_{O4}$ where $V_{O1}$ the output voltage of HB1 and $V_{O4}$ is the output voltage of HB4.

Figure 20:
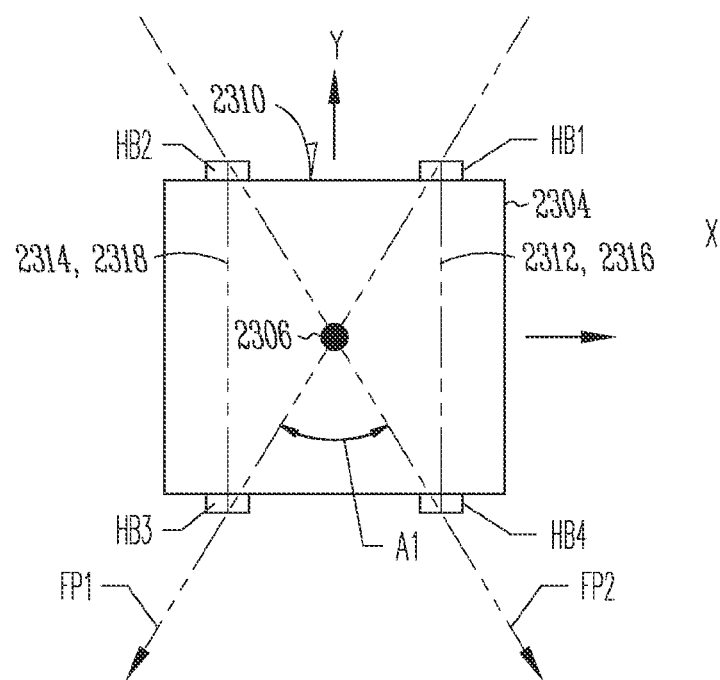
FIG. 20 is an illustrative proximal direction cross-section view of the example beam indicating a first plane strain force and a second plane strain force imparted to first and second half-bridges.

FIG. 20 is an illustrative proximal direction cross-section view of the example beam 2304 of FIGS. 13A-13B indicating a first plane strain force FP1 and a second plane strain force FP2 imparted to the respective first and second half-bridges HB1, HB2 by an applied force upon the beam 2304. In an example force sensor 2302, resistance values of the first pair of resistors, $R_{P1}$, $R_{D1}$, of the first half-bridge HB1 match resistance values of the second pair of resistors, $R_{P2}$, $R_{D2}$, of the second half-bridge HB2. In an example force sensor 2302, the first and second half-bridges HB1, HB2 are positioned upon an example beam 2304, such that an applied force imparted to the example beam 2304 imparts a first plane strain force FP1 to the first half-bridge HB1 within the first plane P1 and imparts a second plane strain force FP2 to the second half-bridge HB2 within the second plane P2. It will be appreciated that the first plane strain force FP1 is an off-axis force since it is a force imparted along the first lateral side axis 2312. Likewise, it will be appreciated that the second plane strain force FP2 is an off-axis force since it is a force imparted along the second lateral side axis 2314. The first and second half-bridges HB1, HB2 are positioned upon an example beam 2304, such that a magnitude of the first plane strain force $FP1_X$ matches a magnitude of the second plane strain force FP2. Force directions of the first plane strain force $FP1_X$ and the first plane P1 are separated from one another by the first separation angle A1.

In this example, the difference between FP1 and FP2 is proportional to the X-direction force component $F_x$ imparted to the beam by the applied force F. Persons skilled in the art will understand the process for determining the difference between FP1 and FP2 based upon the above explanation of a determination of a difference between FP2 and FP3.

Moreover, it will be appreciated that, $F_X$=FP1-FP2

Figure 21:
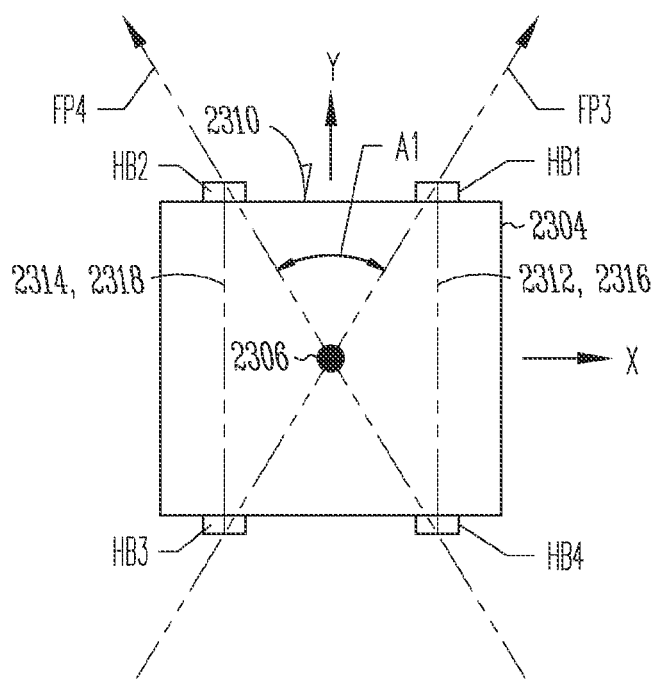
FIG. 21 is an illustrative proximal direction cross-section view of the example beam indicating a third plane strain force and a fourth plane strain force imparted to third and fourth half-bridges.

$F_X \alpha V_{O1} - V_{O2}$ where $V_{O1}$ the output voltage of HB1 and $V_{O2}$ is the output voltage of HB2. FIG. 21 is an illustrative proximal direction cross-section view of the example beam 2304 of FIGS. 13A-13B indicating a third plane strain force FP3 and a fourth plane strain force FP4 imparted to the respective third and fourth half-bridges HB3, HB4 by an applied force $F_X$ upon the beam. In an example force sensor 2302, resistance values of the third pair of resistors, $R_{P3}$, $R_{D3}$, of the third half-bridge HB3 match resistance values of the fourth pair of resistors, $R_{P4}$, $R_{D4}$, of the fourth half-bridge HB4. In an example force sensor 2302, the third and fourth half-bridges HB3, HB4 are positioned upon an example beam 2304, such that an applied force imparted to the example beam 2304 imparts a third plane strain force FP3 to the third half-bridge HB3 within the third plane P3 and imparts a fourth plane strain force FP4 to the fourth half-bridge HB4 within the fourth plane P4. It will be appreciated that the third plane strain force FP3 is an off-axis force since it is a force imparted along the third lateral side axis 2316. Likewise, it will be appreciated that the fourth plane strain force FP4 is an off-axis force since it is a force imparted along the fourth lateral side axis 2318. In an example force sensor 2302, the third and fourth half-bridges HB3, HB4 are positioned upon an example beam 2304, such that a magnitude of the FIG. 21 is an illustrative proximal direction cross-section view of the example beam 2304 of FIGS. 13A-13B indicating a third plane strain force FP3 and a fourth plane strain force FP4 imparted to the respective third and fourth half-bridges HB3, HB4 by an applied force $F_X$ upon the beam.

In this example, the difference between FP3 and FP4 is proportional to the X-direction force component $F_X$ imparted to the beam by the applied force F. Persons skilled in the art will understand the process for determining the difference between FP3 and FP4 based upon the above explanation of a determination of a difference between FP2 and FP3.

Moreover, it will be appreciated that, $F_X = FP3 - FP4$ $F_X \alpha V_{O3} - V_{O4}$ where $V_{O3}$ the output voltage of HB3 and $V_{O4}$ is the output voltage of HB4.

Thus, assuming that all resistors $R_{P1}$-$R_{P4}$ and $R_{D1}$-$R_{D4}$ operate properly, $F_X \alpha V_{O1} - V_{O2} = V_{O3} - V_{O4}$ and $F_Y \alpha V_{O1} - V_{O4} = V_{O2} - V_{O3}$ Furthermore, it will be appreciated that $F_X$ and $F_Y$ can be determined more generally based upon each one of the following four combinations of three half-bridges (HBs) set forth in the following Table 1.

TABLE 1

| HB Combinatino No. | HB Combinations Suitable to Determine Both $F_X$ and $F_Y$ |
|---|---|
| 1 | HB1, HB2, HB3 |
| 2 | HB1, HB2, HB4 |
| 3 | HB3, HB4, HB2 |
| 4 | HB4, HB3, HB1 |

Thus, the half-bridge combinations in the above Table 1 can be used to make redundant determinations of $F_X$ and $F_Y$. A comparison of the $F_X$ and $F_Y$ values determined based upon the above combinations of half-bridges can be used to determine whether the force sensor 2304 contains a malfunctioning resistor. If even a single resistor malfunctions, then then all four combinations would produce different $F_X$ and $F_Y$ values thus indicating failure. Since all four HBs would produce different results in the event of a failure, it will not be possible to determine the failing resistor. Adding one or more additional half-bridges to the beam can be used to achieve an error-tolerant design in that comparisons of five or more combinations of three bridges can be used to make a determination as to which half-bridge is defective, whereupon and measurements from the defective half-bridge can be ignored.

Redundant Single Sided XY Force Sensor

An example single sided XY force sensor includes a beam that includes four half-bridges located on a single side thereof. Two half-bridges are one of compression type and two half-bridges are tension type. Since compression and tension strain gauge resistors measure experience opposite direction strain in response to a force imparted to the beam, measurements by a combination of three half-bridges located on the same side of the beam in which one of the three has a different strain gauge resistor type than the other two can be used to measure both X-direction forces and Y-direction forces. The example single sided XY force sensor that includes four half-bridges, in which two are compression type and two are tension type, can perform redundant XY measurements.

In a sensor having four half-bridges and all gauges of same type on first and reverse sides, subtracting the half bridge voltages of adjacent two half bridges provides a force measurement in the axis parallel to the plane having all the gauges of the two half bridge. There are four ways to do this which provides two measurements of Fx and Fy.

FIG. 13A-13B show an illustrative first side perspective view (FIG. 13A) and second side perspective view (FIG. 13B) of an example force sensor 2302 that includes a rectangular beam 2304 with two four strain gauge resistors $R_{P1}$-$R_{P4}$, $R_{D1}$-$R_{D4}$ coupled in two half Wheatstone bridge circuits ('half-bridges") located on each of two reverse sides thereof. A second side 308 of the beam 2304 shown in FIG. 13B faces in a direction that is reverse of a direction faced by a first side 308 of the beam 2304 shown in FIG. 13A. An (X, Y, Z) beam coordinate system 2305 is provided to explain force directions relative to the beam 2304. An example beam 2304 can have a rectangular cross-section with planar side faces. More particularly, an example beam can have a square cross-section. The beam 2304 includes a proximal beam portion 2304P and a distal beam portion 2304D and includes a longitudinal center axis 306 extending between the proximal and distal beam portions 2304P, 2304D.

Referring to FIG. 13A, a first proximal strain gauge resistor ('resistor') $R_{P1}$ and a second proximal resistor $R_{P2}$ are located at the proximal beam portion 2304P of the first side 308 of the beam 2304. A first distal resistor $R_{D1}$ and a second distal resistor $R_{D2}$ are located at the distal beam portion 2304D of the first side 308 of the beam 2304. As explained below with reference to FIGS. 14A-14B, 15A-15B, a first pair of resistors, $R_{P1}$-$R_{D1}$, are electrically coupled in series and arranged in a first half-bridge, and a second pair of resistors, $R_{P2}$-$R_{D2}$, are electrically coupled in series and arranged in a second half-bridge.

Referring to FIG. 13B, a third proximal resistor $R_{P3}$ and a fourth proximal resistor $R_{P4}$ are located at the proximal beam portion 2304P of the second side 2310 (also referred to as the 'reverse' side) of the beam 2304 that faces in a reverse direction to a direction faced by the first side 308 of the beam 2304. A third distal resistor $R_{D3}$ and a fourth distal resistor $R_{D4}$ are located at a distal beam portion 2304D of the reverse second side 2310 of the beam 2304. As explained below with reference to FIGS. 14A-14B, 15A-15B, a third pair of resistors, $R_{P3}$-$R_{D3}$, are electrically coupled in series and arranged in a third half-bridge, and a fourth pair of resistors, $R_{P4}$-$R_{D4}$, are electrically coupled in series and arranged in a fourth half-bridge arranged in a fourth half-bridge.

FIG. 14A is an illustrative side view of an example beam including a first example half-bridge circuit layout 2402 having proximal and distal tension gauge strain resistors $RT_P$, $RT_D$ electrically coupled in series and having a voltage node coupled between them. The first example half-bridge bridge circuit layout 2402 includes input bias voltage conductors (EP, EN) and output an voltage node (Vo) between the proximal and distal tension resistors $RT_P$, $RT_D$. FIG. 14B is an illustrative first schematic circuit diagram 2404 representation of the first half-bridge circuit layout 2402. Referring to FIGS. 14A-14B, a proximal tension resistor $RT_P$ is electrically coupled between a positive first DC electrical potential (EP) and an output voltage node Vo. A distal tension resistor $RT_D$ is electrically coupled between a negative second DC electrical potential (EN) and the output voltage node Vo. In an example force sensor 2302, each of the first, second, third and fourth half-bridges has a layout 2402 and circuit schematic 2404 represented in FIGS. 14A-14B.

FIG. 15A is an illustrative side view of an example beam showing a second example half-bridge circuit layout 2502 having proximal and distal compression gauge strain resistors $RC_P$, $RC_D$ electrically coupled in series and having a voltage node coupled between them. The second example half-bridge bridge circuit layout 2502 includes input bias voltage conductors (EP, EN) and output an voltage node (Vo) between the proximal and distal compression resistors $RC_P$, $RC_D$. FIG. 15B is an illustrative second schematic circuit diagram 2504 representation of the second half-bridge circuit layout 2502. Referring to FIGS. 15A-15B, a proximal compression resistor $RC_P$ is electrically coupled between a positive first DC electrical potential (EP) and an output voltage node Vo. A distal compression resistor $RC_D$ is electrically coupled between a negative second DC electrical potential (EN) and the output voltage node Vo. In another example force sensor 2302, each of the first, second, third and fourth half-bridges has a layout 2502 and circuit schematic 2504 represented in FIGS. 15A-15B.

As shown in FIGS. 14A-14B and FIGS. 15A-15B, each half-bridge of an example force sensor 2302 includes a pair of strain gauge resistors having matching type, which can be either tension type (FIGS. 14A-14B) or compression type (FIGS. 15A-15B). As used herein reference to a set resistors having 'matching type' refers to a set of resistors in which either all resistors are tension resistors or all resistors are compression resistors. Although either tension or compression gauge resistors can be used to determine X direction and Y direction forces, in general, tension strain gauge resistors are more sensitive than compression gauge resistors.

Referring again to FIGS. 13A-13B, as explained more fully below, a voltage offset between a first half-bridge voltage at a first voltage node between the first pair of resistors $R_{P1}$, $R_{D1}$ and a second half-bridge voltage at a second voltage node between the second pair of resistors $R_{P2}$, $R_{D2}$ can be used to measure X-direction force imparted to the beam 2304. Additionally, a voltage offset between the third half-bridge voltage at a third voltage node between the third pair of resistors $R_{P3}$, $R_{D3}$ and a fourth half-bridge voltage at a fourth voltage node between the fourth pair of resistors $R_{P4}$, $R_{D4}$ can be used to measure X-direction force imparted to the beam 2304. Thus, together, the first, second, third, and fourth half-bridges provide redundant measures of X-direction force upon the beam.

Further, as explained more fully below, a voltage offset between the first half-bridge voltage at a first voltage node between the first pair of resistors $R_{P1}$, $R_{D1}$ and the fourth half-bridge voltage at the fourth voltage node between the fourth pair of resistors $R_{P4}$, $R_{D4}$ can be used to measure Y-direction force imparted to the beam 2304. Additionally, an offset between the second half-bridge voltage at the second voltage node between the second pair of resistors $R_{P2}$, $R_{D2}$ and the third half-bridge voltage at the third voltage node between the third pair of resistors $R_{P3}$, $R_{D3}$ can be used to measure Y-direction force imparted to the beam 2304.

Thus, together, the first, second, third, and fourth half-bridges can provide redundant measures of X-direction force upon the beam 2304 and can provide redundant measures of Y-direction forces upon the beam 2304. A malfunction of any one of resistors $R_{P1}$-$R_{P4}$ and RD-$R_{D4}$ results in differences in X-direction force measurements determined using the first and second half-bridges on the one hand and X-direction force determined measurements using the third and fourth half-bridges on the other. Similarly, a malfunction of any one of resistors $R_{P1}$-$R_{P4}$ and $R_{D1}$-$R_{D4}$ results in differences in Y-direction force measurements determined using the first and fourth half-bridges on the one hand and Y-direction force measurements determined using the second and third half-bridges on the other.

Still referring to FIG. 13A, the first proximal resistor $R_{P1}$ and the first distal resistor $R_{D1}$ are arranged upon the first side 308 of the beam 2304 within a first imaginary plane P1 in which the center axis 306 extends and that defines a first lateral side axis 2312 at a location on the first side 308 of the beam 2304 along which the first plane P1 intersects the first side 308. The first lateral side axis 2312 and the center axis 306 extend parallel to one another. An example first lateral side axis 2312 extends through the first proximal resistor $R_{P1}$ and through the first distal resistor $R_{D1}$. More particularly in an example force sensor, the example first lateral side axis 2312 bisects the example first proximal resistor $R_{P1}$ and bisects the example first distal resistor $R_{D1}$.

Referring to FIG. 13A, the second proximal resistor $R_{P2}$ and the second distal resistor $R_{D2}$ are arranged upon the first side 308 of the beam within a second imaginary plane P2 in which the center axis 306 extends and that defines a second lateral side axis 2314 at a location on the first side 308 of the beam 2304 along which the second plane P2 intersects the first side. The second lateral axis 2314 and the center axis 306 extend parallel to one another. An example second lateral side axis 2314 extends through the second proximal resistor $R_{P2}$ and through the second distal resistor $R_{D2}$. More particularly in an example force sensor, the example second lateral side axis bisects 2314 the example second proximal resistor $R_{P2}$ and bisects an example second distal resistor $R_{D2}$.

Referring to FIG. 13B, the third proximal resistor $R_{P3}$ and the third distal resistor $R_{D3}$ are arranged upon the reverse second side 2310 of the beam 2304 within the first imaginary plane P1, in which the center axis extends 306, and that defines a third lateral side axis 2316 at a location on the second side 2310 of the beam 2304 along which the first plane P1 intersects the second side 2310. An example third lateral side axis 2316 extends through the third proximal resistor $R_{P3}$ and through the third distal resistor $R_{D3}$. More particularly in an example force sensor, the example third side axis 2316 bisects the example third proximal resistor $R_{P3}$ and bisects an example third distal resistor $R_{D3}$.

Referring to FIG. 13B, the fourth proximal resistor $R_{P4}$ and the fourth distal resistor $R_{D4}$ are arranged upon the reverse second side 2310 of the beam 2304 within the second imaginary plane P2, in which the center axis 306 extends, and that defines a fourth lateral side axis 2318 at a location on the second side 2310 of the beam 2304 along which the second plane P2 intersects the second side 2310 of the beam 2304 and that includes the center axis 306. An example fourth lateral side axis 2318 extends through the fourth proximal resistor $R_{P4}$ and through the fourth distal resistor $R_{D4}$. More particularly in an example force sensor, the example fourth lateral side axis bisects an example fourth proximal resistor $R_{P4}$ and bisects an example first distal resistor $R_{D4}$.

FIG. 16 is an illustrative proximal direction cross-section view of the example beam 2304 of FIGS. 13A-13B showing the first and second imaginary planes P1, P2. FIG. 17A is a side view of the beam 2304 showing the first side 308 of the beam of FIGS. 13A-13B, which includes first ($R_{P1}$) and second ($R_{D1}$) and second resistors coupled in a first half-bridge HB1 and includes third ($R_{P2}$) and fourth ($R_{D2}$) resistors coupled in a second half-bridge HB2. FIG. 17B is a side view of the beam 2304 showing the reverse second side 308 of the beam of FIGS. 13A-13B, which includes A second bridge includes fifth ($R_{P3}$) and sixth ($R_{D3}$) resistors coupled in a third half-bridge HB3 and includes seventh ($R_{P4}$) and eighth ($R_{D4}$) resistors coupled in a fourth half-bridge HB4.

The resistors can be placed on the beam 2304 manually or using automated machinery and can be adhered to the beam using an adhesive such as epoxy. Alternatively, the resistors can be deposited and laser etched directly on to the beam 2304. In both cases, an electrical circuit can be completed externally using wirebonds and flexible printed circuit.

Referring to FIG. 16, a proximal direction end view of the beam 2304 shows side views of the first and second planes P1, P2 that intersect one another along the center axis 306, which extends within both the first and second planes. The first plane P1 extends through the first and third half-bridges HB1, HB3 and through the center axis 306. The second plane P1 extends through the second and fourth half bridges HB2, HB4 and through the center axis 306. Portions of the first and second planes P1, P2 that extend through the respective first and second half bridges HB1, HB2 intersect the center axis 306 separated by a first separation angle A1. Portions of the first and second planes P1, P2 that extend through the respective third and fourth half bridges HB3, HB4 also intersect the center axis 306 separated by the first separation angle A1.

Referring to FIG. 17A, the first plane P1 is shown extending through the first half bridge HB1, which includes the first (proximal resistor $R_{P1}$ and the first distal resistor $R_{D1}$, which are arranged along the first lateral side axis 2312 on the first side 308 of the beam 2304, and the second plane P2 is shown extending through the second half-bridge HB2, which includes the second proximal resistor $R_{P2}$ and the second distal resistor $R_{D2}$, which are arranged along the second lateral side axis 2314 on the first side 308 of the beam 2304. Size of the first separation angle A1 corresponds to lateral spacing distance at the first side 308, between the first and second lateral side axes 2312, 2314, and therefore, corresponds to lateral spacing between the first half-bridge HB1 including the first proximal and distal resistors $R_{P1}$, $R_{D1}$ and a second resistor pair including the second proximal and distal resistors $R_{P2}$, $R_{D2}$. In an example force sensor 2302, the first lateral side axis 2312 and the second lateral side axis 2314 are equidistant from a neutral axis of the first side of the beam 2304, which is equidistant from the first and second lateral side edges 2312, 2314 of the first side 308 of the beam 2304.

Referring to FIG. 17B, the first plane P1 is shown extending through the third half bridge HB3, which includes the third proximal resistor $R_{P3}$ and the third distal resistor $R_{D3}$, which are arranged along the third lateral side axis 2316 on the second side 2310 of the beam 2304, and the second plane P2 is shown extending through the fourth half bridge HB4, which includes the fourth proximal resistor $R_{P4}$ and the fourth distal resistor $R_{D4}$, which are arranged along the fourth lateral side axis 2318 on the second side 2310 of the beam 2304. Size of the first separation angle A1 corresponds to lateral spacing distance at the second side 2310 of the beam 2304, between the third and fourth lateral side axes 2316-2318, and therefore, corresponds to lateral spacing between the third half-bridge HB3 including the third resistor pair including $R_{P3}$, $R_{D3}$, and the fourth half-bridge HB4 including the fourth resistor pair including $R_{P4}$, $R_{D4}$. In an example force sensor the third lateral side axis 2316 and the fourth lateral side axis 2318 are equidistant from a neutral axis of the second side 2310 of the beam 2304, which is equidistant from the third and fourth lateral side edges 2316, 2318 of the second side 2310 of the beam 2304.

The half-bridges HB1-HB4 are laterally located symmetrically about the beam 2304. separation angle A1 between the first and second half-bridges matches the first separation angle A1 between the third and fourth half-bridges HB3-HB4. Moreover, in an example force sensor 2302, spacing between the first and second lateral side axes 2312, 2314 matches spacing between the third and fourth lateral side axes 2316, 2318, although equidistant spacing is not required. The half-bridges HB1-HB4 are longitudinally located symmetrically along the beam 2304. Proximal resistors $R_{P1}$-$R_{P4}$ are positioned at matching longitudinal locations of the beam. In an example force sensor, the distal resistors $R_{D1}$-$R_{D4}$ are positioned at matching longitudinal locations of the beam.

FIG. 18A is an illustrative proximal direction cross-section view of the example beam 2304 of FIGS. 13A-13B indicating a second plane strain force FP2 and a third plane strain force FP3 imparted to the respective second and third half-bridges HB2, HB3 by an applied force F upon the beam 2304. In the example beam of FIG. 18A, the second and third half-bridges HB2, HB3 contain only tension resistors. FIG. 18B is an illustrative force diagram that indicates orthogonal X and Y force components of the second plane strain force FP2 imparted to the second half-bridge HB2 that includes the second proximal resistor $R_{P2}$ and the second distal resistor $R_{D2}$, in response to the applied force F. FIG. 18C is an illustrative force diagram that indicates orthogonal X and Y force components of the third plane strain force FP3 imparted to the third half-bridge HB3, which includes the third proximal resistor $R_{P3}$ and the third distal resistor $R_{D3}$, in response to the applied force.

In an example force sensor 2302, resistance values of the second pair of resistors, $R_{P2}$, $R_{D2}$, of the second half-bridge HB2 match resistance values of the third pair of resistors, $R_{P3}$, $R_{D3}$, of the third half-bridge HB3. In an example force sensor 2302, the second and third half-bridges HB2, HB3 are positioned upon an example beam 2304, such that an applied force imparted to the example beam 2304 imparts a second plane strain force FP2 to the second half-bridge HB2 within the second plane P2 and imparts a third plane strain force FP3 to the third half-bridge HB3 within the third plane P3. It will be appreciated that the second plane strain force FP2 is an off-axis force since it is a force imparted along the second lateral side axis 2314. Likewise, it will be appreciated that the third plane strain force FP3 is an off-axis force since it is a force imparted along the third lateral side axis 2316. In an example force sensor 2302, the second and third half-bridges HB2, HB3 are positioned upon an example beam 2304, such that a magnitude of the components of second plane strain force FP2 matches magnitude of the components of third plane strain force FP3.

An advantage of using strain gauge resistors of the same type is that magnitude of a force imparted perpendicular to the center axis 306 of a beam 2304 can be determined based upon a difference in magnitude of off-axis forces imparted to the different half-bridges of a full-bridge located on the beam. In the the example force sensor 2302, magnitude of a Y-direction force component $F_Y$ imparted to the beam 2304 by an applied force F can be determined based upon difference between the first off-axis force FP2 and the second off-axis force FP3 as follows.

Let A be angle between P2 and P3.
Let X axis bisect the angle A. Therefore, an angle between P2 and X is A/2 and an angle between P3 and X is A/2.
Let θ be an angle between the X axis and an applied force F.
Force along X axis $F_x$=F cos θ
Force along y axis $F_y$=F sin θ
Referring to FIG. 18B, force along P2=$F_x$ cos A/2+$F_y$ cos (90+A/2)=FP2
Referring to FIG. 18C, force along P3=$F_x$ cos A/2+$F_y$ cos (90−A/2)=FP3
FP2=$F_x$ cos A/2+$F_y$ cos (90+A/2)
FP3=$F_x$ cos A/2+$F_y$ cos (90−A/2)
Using cos (θ)=−cos (180−θ)
we get
FP3=$F_x$ cos A/2−$F_y$ cos (90+A/2)
When we subtract FP1 and FP2
we get FP2−FP3=$F_x$ cos A/2+$F_y$ cos (90+A/2)−$F_x$ cos A/2+$F_y$ cos (90+A/2)
Therefore, FP2−FP2=2 $F_y$ cos (90+A/2)
Therefore, FP2−FP3 ∝$F_y$
Thus, the difference between FP2 and FP3 is proportional to the Y-direction force component $F_y$ imparted to the beam by the applied force F.

Moreover, it will be appreciated that,
$F_Y$=FP2−FP2
$F_Y$ α $V_{O2}$−$V_{O3}$
where $V_{O2}$ the output voltage of HB2 and $V_{O3}$ is the output voltage of HB3.

FIG. 19 is an illustrative proximal direction cross-section view of the example beam of FIGS. 13A-13B indicating a first plane strain force FP1 and a fourth plane strain force FP4 imparted to the respective first and fourth half-bridges HB1, HB4 by an applied force F upon the beam 2304. In the example beam of FIG. 19, the first and fourth half-bridges HB1, HB4 contain only tension resistors. In an example force sensor 2302, resistance values of the first pair of resistors, $R_{P1}$, $R_{D1}$, of the first half-bridge HB1 match resistance values of the fourth pair of resistors, $R_{P4}$, $R_{D4}$, of the fourth half-bridge HB4. In an example force sensor 2302, the first and fourth half-bridges HB1, HB4 are positioned upon an example beam 2304, such that an applied force F imparted to the example beam 2304 imparts a first plane strain force FP1 to the first half-bridge HB1 within the first plane P1 and imparts a fourth plane strain force FP4 to the fourth half-bridge HB4 within the second plane P4. In an example force sensor 2302, the first and fourth half-bridges HB1, HB4 are positioned upon an example beam 2304, such that a magnitude of components of the first plane strain force FP1 matches a magnitude of components of the fourth plane strain force FP4.

In this example, the difference between FP1 and FP4 is proportional to the Y-direction force component $F_Y$ imparted to the beam by the applied force F. Persons skilled in the art will understand the process for determining the difference between FP1 and FP4 based upon the above explanation of a determination of a difference between FP2 and FP3.

Moreover, it will be appreciated that,
$F_Y$=FP1−FP4
$F_Y$ α $V_{O1}$−$V_{O4}$
where $V_{O1}$ the output voltage of HB1 and $V_{O4}$ is the output voltage of HB4.

FIG. 20 is an illustrative proximal direction cross-section view of the example beam 2304 of FIGS. 13A-13B indicating a first plane strain force FP1 and a second plane strain force FP2 imparted to the respective first and second half-bridges HB1, HB2 by an applied force upon the beam 2304. In an example force sensor 2302, resistance values of the first pair of resistors, $R_{P1}$, $R_{D1}$, of the first half-bridge HB1 match resistance values of the second pair of resistors, $R_{P2}$, $R_{D2}$, of the second half-bridge HB2. In an example force sensor 2302, the first and second half-bridges HB1, HB2 are positioned upon an example beam 2304, such that an applied force imparted to the example beam 2304 imparts a first plane strain force FP1 to the first half-bridge HB1 within the first plane P1 and imparts a second plane strain force FP2 to the second half-bridge HB2 within the second plane P2. It will be appreciated that the first plane strain force FP1 is an off-axis force since it is a force imparted along the first lateral side axis 2312. Likewise, it will be appreciated that the second plane strain force FP2 is an off-axis force since it is a force imparted along the second lateral side axis 2314. The first and second half-bridges HB1, HB2 are positioned upon an example beam 2304, such that a magnitude of the first plane strain force FP1$_X$ matches a magnitude of the second plane strain force FP2. Force directions of the first plane strain force FP1$_X$ and the first plane P1 are separated from one another by the first separation angle A1.

In this example, the difference between FP1 and FP2 is proportional to the X-direction force component $F_x$ imparted to the beam by the applied force F. Persons skilled in the art will understand the process for determining the difference between FP1 and FP2 based upon the above explanation of a determination of a difference between FP2 and FP3.

Moreover, it will be appreciated that,
$F_X$=FP1−FP2
$F_X$ a $V_{O1}$−$V_{O2}$
where $V_{O1}$ the output voltage of HB1 and $V_{O2}$ is the output voltage of HB2. FIG. 21 is an illustrative proximal direction cross-section view of the example beam 2304 of FIGS. 13A-13B indicating a third plane strain force FP3 and a fourth plane strain force FP4 imparted to the respective third and fourth half-bridges HB3, HB4 by an applied force $F_X$ upon the beam. In an example force sensor 2302, resistance values of the third pair of resistors, $R_{P3}$, $R_{D3}$, of the third half-bridge HB3 match resistance values of the fourth pair of resistors, $R_{P4}$, $R_{D4}$, of the fourth half-bridge HB4. In an example force sensor 2302, the third and fourth half-bridges HB3, HB4 are positioned upon an example beam 2304, such that an applied force imparted to the example beam 2304 imparts a third plane strain force FP3 to the third half-bridge HB3 within the third plane P3 and imparts a fourth plane strain force FP4 to the fourth half-bridge HB4 within the fourth plane P4. It will be appreciated that the third plane strain force FP3 is an off-axis force since it is a force imparted along the third lateral side axis 2316. Likewise, it will be appreciated that the fourth plane strain force FP4 is an off-axis force since it is a force imparted along the fourth lateral side axis 2318. In an example force sensor 2302, the third and fourth half-bridges HB3, HB4 are positioned upon an example beam 2304, such that a magnitude of the FIG. 21 is an illustrative proximal direction cross-section view of the example beam 2304 of FIGS. 13A-13B indicating a third plane strain force FP3 and a fourth plane strain force FP4 imparted to the respective third and fourth half-bridges HB3, HB4 by an applied force $F_x$ upon the beam.

In this example, the difference between FP3 and FP4 is proportional to the X-direction force component $F_x$ imparted to the beam by the applied force F. Persons skilled in the art will understand the process for determining the difference between FP3 and FP4 based upon the above explanation of a determination of a difference between FP2 and FP3.

Moreover, it will be appreciated that, $F_X$=FP3−FP4

$F_X \alpha V_{O3} - V_{O4}$ where $V_{O3}$ the output voltage of HB3 and $V_{O4}$ is the output voltage of HB4.

Thus, assuming that all resistors $R_{P1}$-$R_{P4}$ and $R_{D1}$-$R_{D4}$ operate properly, $F_X \alpha V_{O1} - V_{O2} = V_{O3} - V_{O4}$ and $F_Y \alpha V_{O1} - V_{O4} = V_{O2} - V_{O3}$ Furthermore, it will be appreciated that $F_X$ and $F_Y$ can be determined more generally based upon each one of the following four combinations of three half-bridges (HBs) set forth in the following Table 1.

TABLE 1

| HB Combinatino No. | HB Combinations Suitable to Determine Both $F_X$ and $F_Y$ |
| --- | --- |
| 1 | HB1, HB2, HB3 |
| 2 | HB1, HB2, HB4 |
| 3 | HB3, HB4, HB2 |
| 4 | HB4, HB3, HB1 |

Thus, the half-bridge combinations in the above Table 1 can be used to make redundant determinations of $F_X$ and $F_Y$. A comparison of the $F_X$ and $F_Y$ values determined based upon the above combinations of half-bridges can be used to determine whether the force sensor 2304 contains a malfunctioning resistor. If even a single resistor malfunctions, then then all four combinations would produce different $F_X$ and $F_Y$ values thus indicating failure. Since all four HBs would produce different results in the event of a failure, it will not be possible to determine the failing resistor. Adding one or more additional half-bridges to the beam can be used to achieve an error-tolerant design in that comparisons of five or more combinations of three bridges can be used to make a determination as to which half-bridge is defective, whereupon and measurements from the defective half-bridge can be ignored.

Redundant Single Sided XY Force Sensor

An example single sided XY force sensor includes a beam that includes four half-bridges located on a single side thereof. Two half-bridges are one of compression type and two half-bridges are tension type. Since compression and tension strain gauge resistors measure experience opposite direction strain in response to a force imparted to the beam, measurements by a combination of three half-bridges located on the same side of the beam in which one of the three has a different strain gauge resistor type than the other two can be used to measure both X-direction forces and Y-direction forces. The example single sided XY force sensor that includes four half-bridges, in which two are compression type and two are tension type, can perform redundant XY measurements.

More generally, however, based upon any three of the four half-bridge measurements one would be able to measure Fx, Fy and temperature gradient. For a beam with four half-bridges, two tension and two compression, there are four ways to pick three of four half-bridges, and therefore, we can get four measurements of Fx and Fy and thus provide redundancy in measurement.

Figure 22:
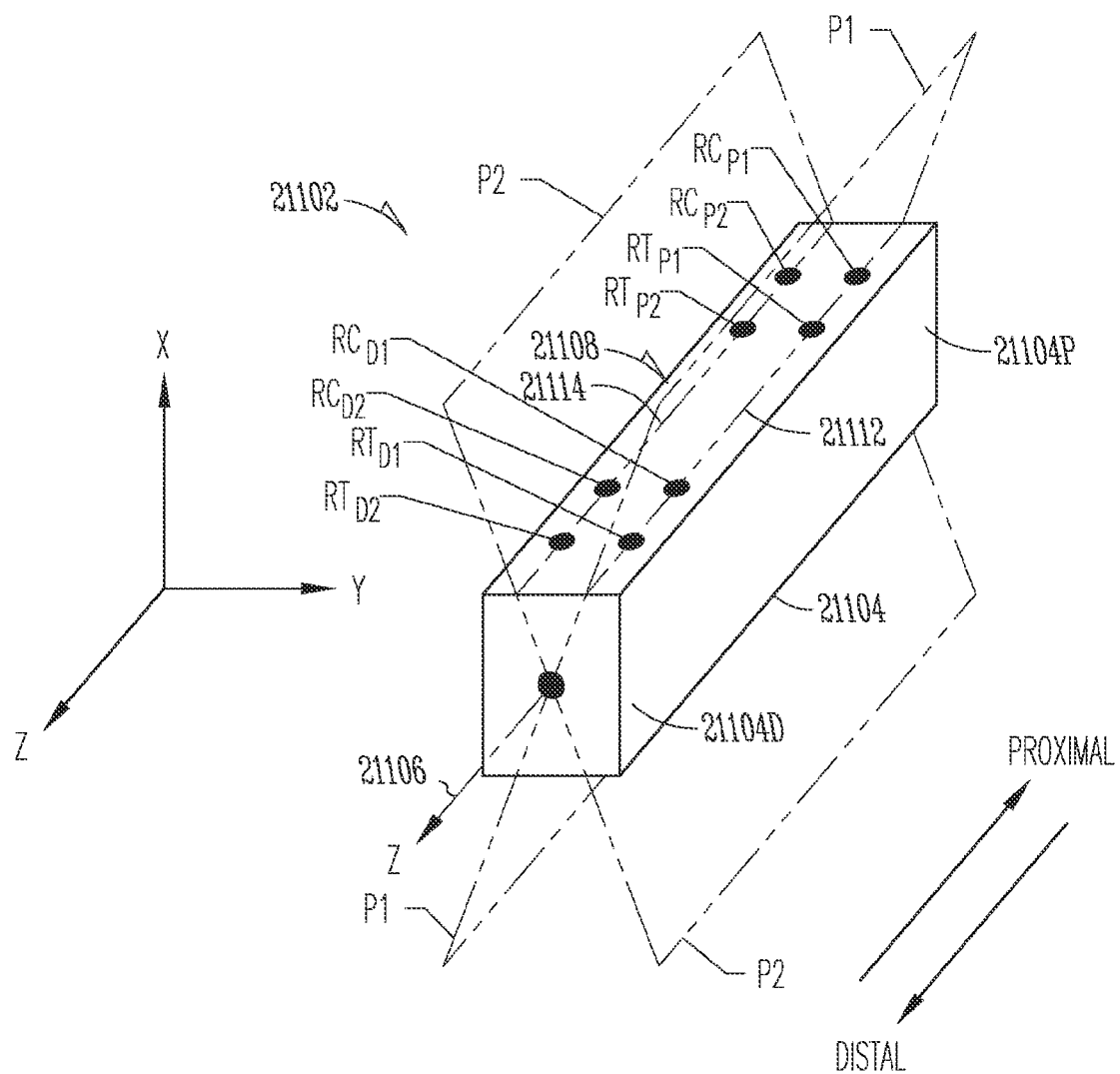
FIG. 22 shows an illustrative top perspective view of an example force sensor that includes a rectangular beam with two tension resistor half-bridge circuits and two compression resistor half-bridges circuits located on a first side thereof.

FIG. 22 shows an illustrative top perspective view of an example force sensor 21102 that includes a rectangular beam 21104 that includes two example tension resistor half-bridges and two example compression resistor half-brigs located on an outer first side surface 21108 thereof. An example beam 21104 includes a planar first side surface 21108. The beam 21104 includes a proximal beam portion 21104P and a distal beam portion 21104D and includes a center axis 21106 extending between the proximal and distal beam portions. The two example tension half-bridges have the first circuit layout 2402 and the first circuit schematic 2404 of FIGS. 14A-14B. The two example compression half-bridges have the second circuit layout 2502 and the second circuit schematic 2504 of FIGS. 15A-15B.

A first pair of tension resistors includes a first proximal tension resistor $RT_{P1}$ located at the proximal beam portion 21104P and a first distal tension resistor $RT_{D1}$ located at the distal beam portion 21104D. The first proximal tension resistor $RT_{P1}$ and the first distal tension resistor $RT_{D1}$ are electrically coupled in series and arranged in a first tension half-bridge HB1$_T$. A second pair of tension resistors includes a second proximal tension resistor ($RT_{P2}$) located at the proximal beam portion 21104P and a second distal tension resistor ($RT_{D2}$) located at the distal beam portion 21104D. The second proximal tension resistor $RT_{P2}$ and the second distal tension resistor $RT_{D2}$ are electrically coupled in series and arranged in a second tension half-bridge HB2$_T$. A first pair of compression resistors includes a first proximal compression resistor ($RC_{P1}$) located at the proximal beam portion 21104P and a first distal compression resistor ($RC_{D1}$) located at the distal beam portion 21104D. The first proximal compression resistor ($RC_{P1}$) and the first distal compression resistor ($RC_{D1}$) are electrically coupled in series and arranged in a third compression resistor half-bridge HB3$_C$. A second pair of compression resistors includes a second proximal compression resistor resistor ($RC_{P2}$) located at the proximal beam portion 21104P and an second distal compression resistor resistor ($RC_{D2}$) located at the distal beam portion 21104D. The second proximal compression resistor ($RC_{P2}$) and the second distal compression resistor ($RC_{D2}$) are electrically coupled in series and arranged in a fourth compression resistor half-bridge HB4c.

As will be appreciated from the explanation of illustrative FIGS. 14A-14B and FIGS. 15A-15B and as explained more fully below, a respective output voltage node is located between each of the respective first pair of tension resistors $RT_{P1}$, $RT_{D1}$ of HB1$_T$, the respective second pair of tension resistors $RT_{P2}$, $RT_{D2}$ of HB2$_T$, the respective first pair of compression resistors $RC_{P1}$, $RC_{D1}$ of HB3$_C$, and the respective second pair of compression resistors $RC_{P2}$, $RC_{D2}$ of $HB4_T$. Voltage offsets between certain combinations of these different output voltages can be used to determine redundant measures of X-force imparted to the beam. Voltage offsets between certain combinations of these different output voltages can be used to determine redundant measures of Y-force imparted to the beam. A malfunction of any one of resistors $RT_{P1}$, $RT_{P2}$, $RT_{D1}$, $RT_{D2}$, $RC_{P1}$, $RC_{P2}$, $RC_{D1}$, $RC_{D2}$ results in differences in redundant X-direction force measurements. Similarly, a malfunction of any one of the resistors results in differences in redundant Y-direction force measurements. A difference in the redundant X-direction force measurements and/or redundant Y-direction force measurements indicates a malfunction of the force sensor.

Still referring to FIG. 22, the first proximal tension resistor $RT_{P1}$, the first distal tension resistor $RT_{D1}$, the first proximal compression resistor $RC_{P1}$ and the first distal compression resistor $RC_{D1}$ are arranged upon the first side 21108 of the beam within a first imaginary plane P1, in which the center axis 21108 extends, and that defines a first lateral side axis 21112 at a location on the first side 21108 of the beam 21104 along which the first plane P1 intersects the first side 21108. The first lateral side axis 21112 and the center axis 21106 extend parallel to one another. An example first lateral side axis 21112 extends through the first proximal and distal tension resistors $RT_{P1}$-$RT_{D1}$ and through the first proximal and distal compression resistors $RC_{P1}$-$RC_{D1}$. An example first lateral side axis 21112 bisects the example first proximal and distal tension resistor and the example first proximal and distal compression resistors.

The second proximal tension resistor $RT_{P2}$, the second distal tension resistor $RT_{D2}$, the second proximal compression resistor $RC_{P2}$ and the second distal compression resistor $RC_{D2}$ are arranged upon the first side 21108 of the beam 21104 within a second imaginary plane P2, in which the center axis 21106 extends, and that defines a second lateral side axis 21114 at a location on the first side 21108 of the beam 21104 along which the second plane P2 intersects the first side 21108. The second lateral side axis 21114 and the center axis 21106 extend parallel to one another. An example second lateral side axis 21114 extends through the second proximal and distal tension resistors $RT_{P2}$-$RT_{D2}$ and through the second proximal and distal compression resistors $RC_{P2}$-$RC_{D2}$. An example second lateral side axis 21114 bisects the example second proximal and distal tension resistor and the example second proximal and distal compression resistors.

Figure 23:
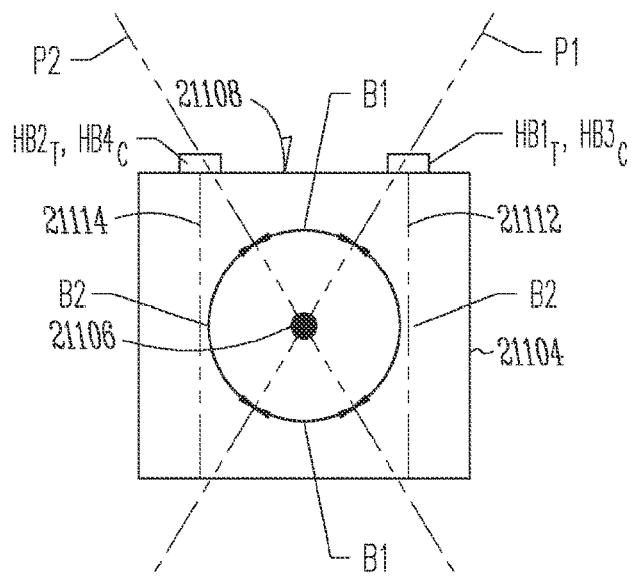
FIG. 23 is an illustrative proximal direction cross-section view of the example beam of FIG. 22.

FIG. 23 is an illustrative proximal direction cross-section view of the example beam 21104 of FIG. 22. The proximal direction end view of the beam shows side views of the first and second planes P1, P2 that intersect one another along the center axis 21106, which extends within both the first and second planes. The first and third half-bridges $HB1_T$, $HB3_C$ are longitudinally aligned along one lateral edge of the beam 21104, and the second and fourth half-bridges $HB2_T$, $HB4_C$ are longitudinally aligned along an opposite edge of the beam 21104. A portion of the first plane that extend through half-bridge circuits $HB1_T$, $HB3_C$ and a portion of the second plane P2 that extends through half-bridge circuits $HB2_T$, $HB4_C$ intersect the center axis 306 separated by a first separation angle B1.

Figure 24:
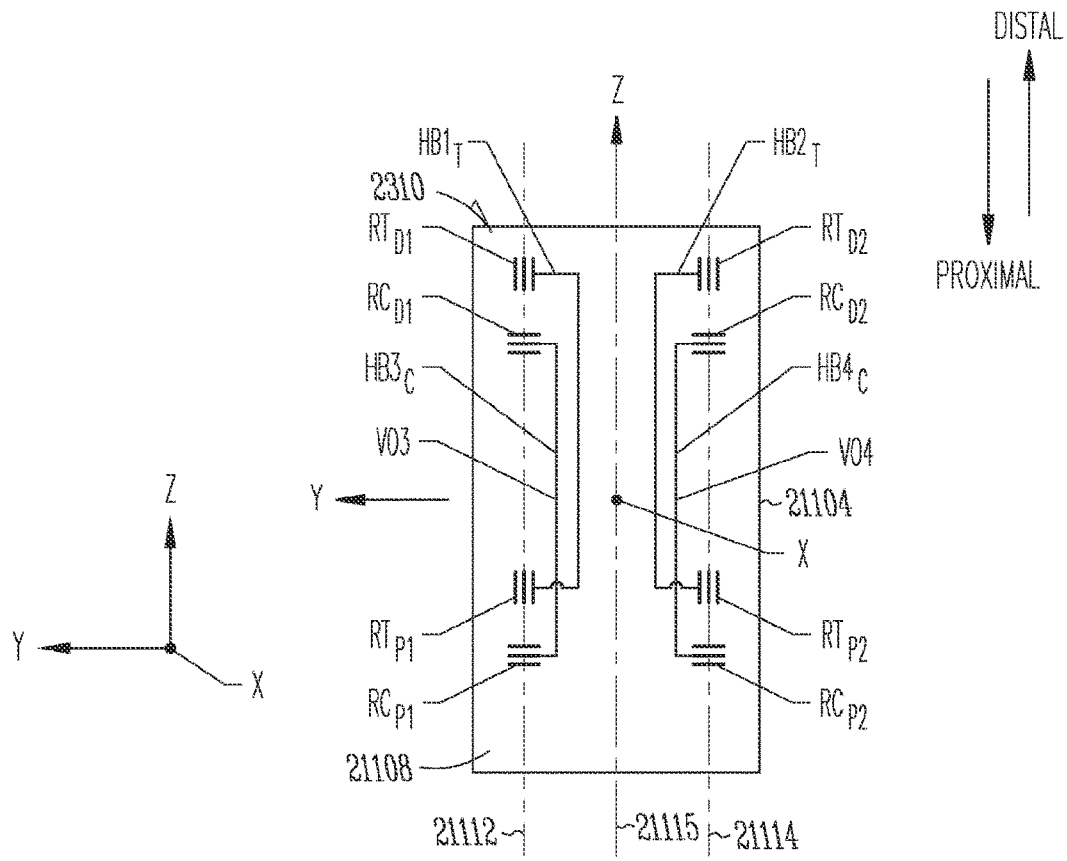
FIG. 24 is a side view of the first side of the example beam of FIG. 22 on which the two tension resistor half bridges and the two compression resistor half-bridges are located.

FIG. 24 is a side view of the outer surface first side 21108 of the example beam 21104 of FIG. 22 on which the two tension resistor half bridges $HB1_T$, $HB2_T$ and the two compression resistor half-bridges $HB3_C$, $HB4_C$ are located. The first plane FP1 is shown extending through the first tension resistor half-bridge $HB1_T$ containing the first proximal and distal tension resistors and proximal resistor $RT_{P1}$, $RT_{D1}$ and through the third compression resistor half-bridge $HB3_C$ containing the first proximal and distal compression resistors $RC_{P1}$, $RC_{D1}$. The second plane P2 is shown extending through the second tension resistor half-bridge $HB2_T$ containing the second proximal and distal tension resistors and proximal resistor $RT_{P2}$, $RT_{D2}$ and through the fourth compression resistor half-bridge $HB4_C$ containing the second proximal and distal compression resistors $RC_{P2}$, $RC_{D2}$. Size of the first separation angle B1 corresponds to lateral spacing distance at the first side 21108, between the first and second lateral side axes 21112, 21114, and therefore, corresponds to lateral spacing between the first tension resistor pair $R_{P1}$, $R_{D1}$ and the first compression resistor pair $RC_{P1}$, $RC_{D1}$ on the one hand and the second tension resistor pair $R_{P2}$, $R_{D2}$ and the second compression resistor pair $RC_{P2}$, $RC_{D2}$ on the other. In an example force sensor 21102 the first lateral side axis 21112 and the second lateral side axis 21114 are equidistant from a neutral axis 21115 that extends within a surface of the of the first side 21108 of the beam 21104, parallel to the center axis 21106 and equidistant from opposite lateral edges of the first side 21108.

The resistors of the first and third half-bridges $HB1_T$ and $HB3_C$ are interleaved. $RC_{D1}$ is aligned with the first lateral side axis 21112 between $RT_{D1}$ and $RT_{P1}$. $RT_{P1}$ is aligned along the first lateral side axis 21112 between between $RC_{D1}$ and $RC_{P1}$.

The resistors of the second and fourth half-bridges $HB2_T$ and $HB4_C$ are interleaved. $RC_{D4}$ is aligned with the second lateral side axis 21114 between $RT_{D2}$ and $RT_{P2}$. $RT_{P2}$ is aligned along the second lateral side axis 21114 between $RC_{D3}$ and $RC_{P4}$.

A first voltage node $V_{O1}$ is coupled between first tension resistor pair $RT_{D1}$ and $RT_{P1}$. A second voltage node $V_{O2}$ is coupled between second tension resistor pair $RT_{D2}$ and $RT_{P2}$. A third voltage node $V_{O3}$ is coupled between first compression resistor pair $RC_{D1}$ and $RC_{P1}$. A fourth voltage node $V_{O4}$ is coupled between second compression resistor pair $RC_{D2}$ and $RC_{P2}$.

In an example force sensor, the first and second proximal tension resistors $RT_{P1}$, $RT_{P2}$ are positioned at matching longitudinal locations of the beam 21104. In an example force sensor, the first and second distal resistors tension $RT_{D1}$, $RT_{D2}$ are positioned at matching longitudinal locations of the beam 21104. Similarly, in an example force sensor, the first and second proximal compression resistors $RC_{P1}$, $RC_{P2}$ are positioned at matching longitudinal locations of the beam 21104. In an example force sensor, the first and second distal resistors compression $RC_{D1}$, $RC_{D2}$ are positioned at matching longitudinal locations of the beam 21104.

Figure 25:
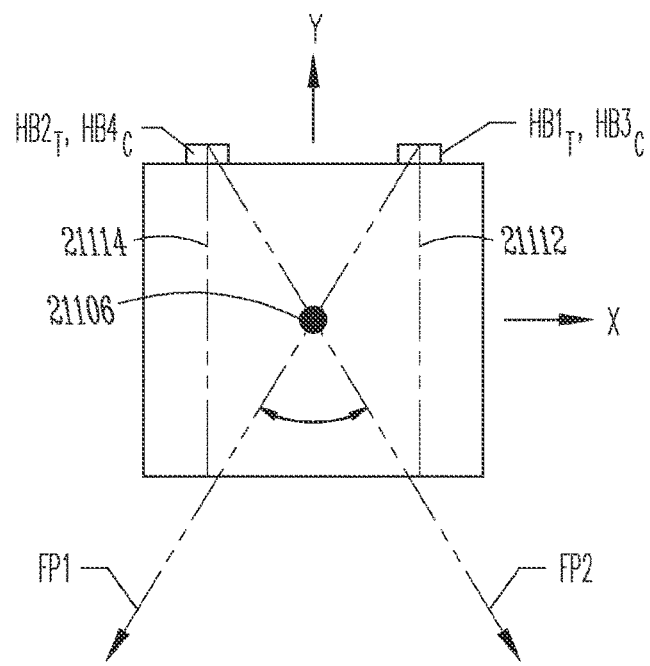
FIG. 25 is an illustrative cross-sectional end view of the example beam indicating a first plane strain force and a second plane strain force imparted to first and second half-bridges.

FIG. 25 is an illustrative cross-sectional end view of the example beam 21104 of FIG. 22 indicating a first plane strain force FP1 and a second plane strain force FP2 imparted to the respective first and second tension resistor half-bridges $HB1_T$, $HB2_T$ by an applied force F force upon the beam 21104. In an example force sensor 21102, resistance values of the first pair of resistors, $RT_{P1}$, $RT_{D1}$, of the first half-bridge $HB1_T$ match resistance values of the second pair of resistors, $RT_{P2}$, $RT_{D2}$, of the second half-bridge $HB2_T$. In an example force sensor 21102, the first and second half-bridges $HB1_T$, $HB2_T$ are positioned upon an example beam 21104, such that an X-direction force imparted to the example beam 21104 imparts a first plane strain force FP1 to the first half-bridge $HB1_T$ within the first plane P1 and imparts a second plane strain force FP2 to the second half-bridge $HB2_T$ within the second plane P2. $HB1_T$ and $HB2_T$ can be used to determine X-direction component of the applied force by determining differences between plane forces.

Figure 26:
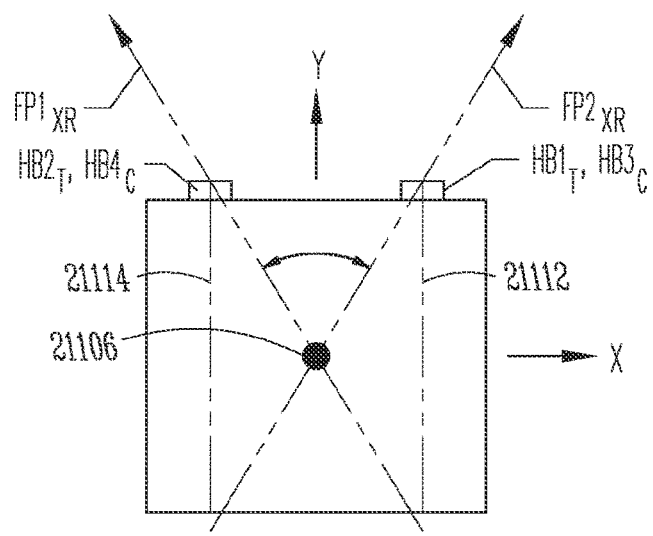
FIG. 26 is an illustrative end cross-section view of an example beam indicating a first plane strain force and a second plane strain force imparted to third and fourth half-bridges.

FIG. 26 is an illustrative cross sectional end cross-section view of the example beam 21104 of FIG. 22 indicating a first plane strain force FP1 and a second plane strain force FP2 imparted to the respective third and fourth compression resistor half-bridges $HB3_C$, $HB4_C$ by an applied force upon the beam 21104. In an example force sensor 21102, the third and compression fourth half-bridges $HB3_C$, $HB4_C$ are positioned upon an example beam 21104, such that an applied force imparted to the example beam 21104 imparts a third plane strain force FP3 to the third compression half-bridge $HB3_C$ within the first plane P1 and imparts a fourth plane strain force FP4 to the fourth compression half-bridge $HB4_C$ within the second plane P2. $HB3_C$ and $HB4_C$ can be used to determine X-direction component of the applied force by determining differences between plane forces.

Figure 27:
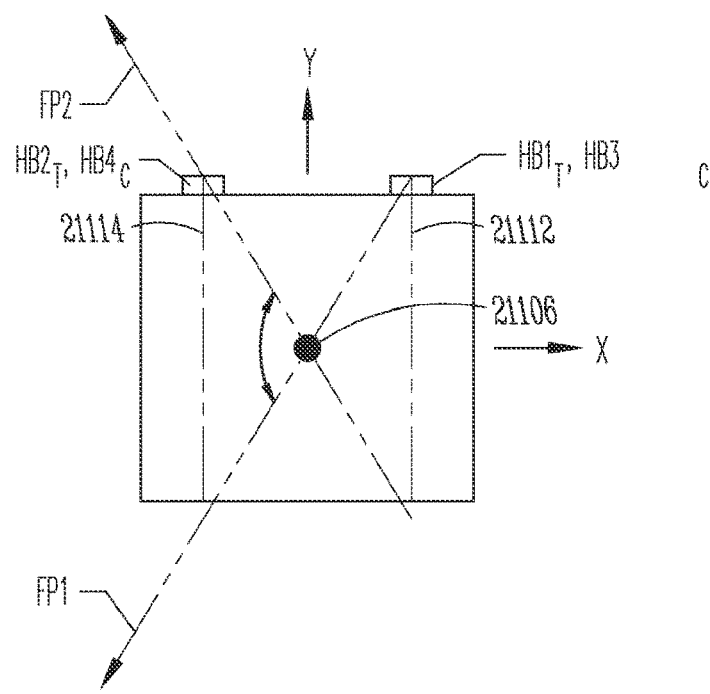
FIG. 27 is an illustrative cross-section end view of the example beam indicating a first plane strain force and a fourth plane strain force imparted to first and fourth half-bridges.

FIG. 27 is an illustrative cross-sectional end view of the example beam 21104 of FIG. 22 indicating a first plane strain force FP1 and a fourth plane strain force FP2 imparted to the respective first tension and fourth compression resistor half-bridges $HB1_T$, $HB4_C$ by an applied force upon the beam 21104. In an example force sensor 21102, the first tension and fourth compression half-bridges $HB1_T$, $HB4_C$ are positioned upon an example beam 21104, such that an applied force imparted to the example beam 21104 imparts a first plane strain force FP1 to the first tension half-bridge $HB1_T$ within the first plane P1 and imparts a fourth plane strain force FP4 to the fourth compression half-bridge $HB4_C$ within the second plane P2. $HB1_T$ and $HB4_C$ can be used together with one of $HB2_T$ or $HB3_C$ to determine Y-direction component of the applied force as explained below with reference to FIG. 29.

Figure 28:
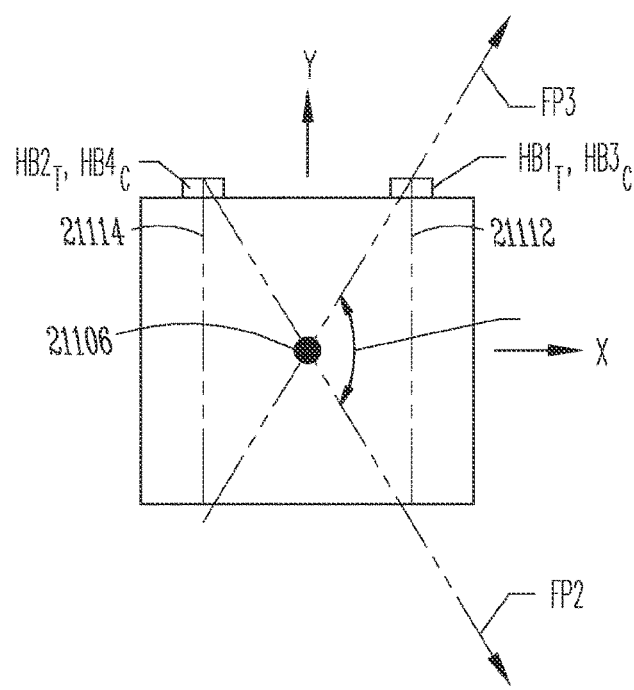
FIG. 28 is an illustrative cross-section end view of the example beam indicating a second plane strain force and a third plane strain force imparted to second and third half-bridges.

FIG. 28 is an illustrative cross-sectional end view of the example beam 21104 of FIG. 22 indicating a reverse second plane strain force FP2 and a third plane strain force FP3 imparted to the respective second tension and third compression resistor half-bridges $HB2_T$, $HB3_C$ by an applied force upon the beam 21104. In an example force sensor 21102, the second tension and third compression half-bridges $HB2_T$, $HB3_C$ are positioned upon an example beam 21104, such that an applied force imparted to the example beam 21104 imparts a third plane strain force FP2 to the third compression half-bridge $HB3_C$ within the first plane P1 and imparts a second plane strain force FP2 to the second tension half-bridge $HB2_T$ within the second plane P2. $HB2_T$ and $HB3_C$ be used together with one of $HB1_T$ or $HB4_C$ to determine Y-direction component of the applied force as explained below with reference to FIG. 29.

Determining a force components by subtracting off-axis force components does not work for half-bridge pairs that have different resistor types since compression and tension resistor have non-matching sensitivities. However, in the example sensor 21102, which includes both tension resistor type half-bridges and compression resistor-type half-bridges, any combination of three half bridges can be used to determine both an $F_X$ component and an $F_Y$ component, which are orthogonal to one another, of an applied force F, which is explained as follows with reference to FIG. 29.

Figure 29:
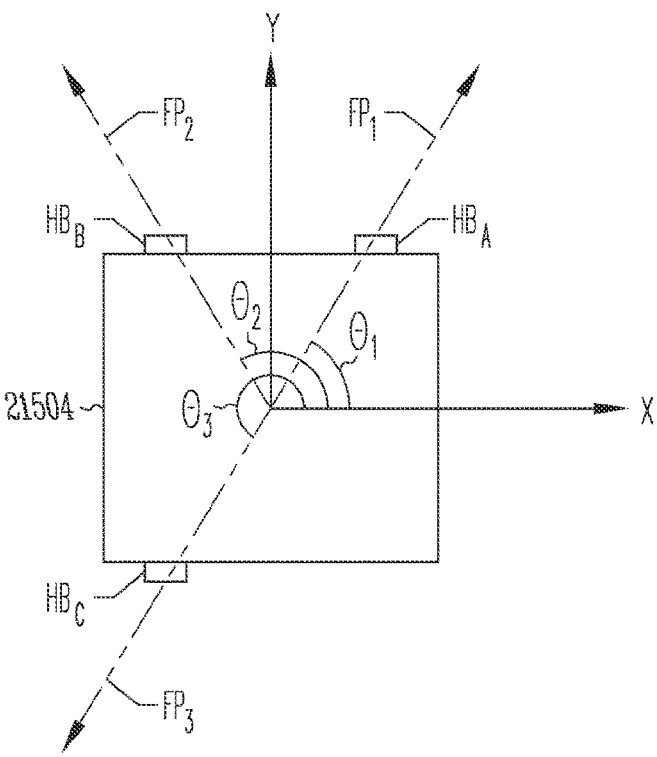
FIG. 29 is an illustrative end cross-section view of the example beam indicating forces imparted to the three example half-bridges located thereon.

FIG. 29 is an illustrative end cross-section view of the example beam 21504 indicating forces imparted to the three example half-bridges $HB_A$, $HB_B$, $HB_C$ located thereon. In the following explanation, two half-bridges can be same type (either tension resistor type or compression resistor type) and a third half-bridge can be of the same type or opposite type. It is noted that unlike the beam 21102 of FIG. 22, which has four half-bridges on one side, the beam 21504 has two half-bridges, $HB_A$ and $HB_B$, both located together on a same side of a beam and has a third half-bridge, $HB_C$, located on an opposite side of the beam. Persons skilled in the art will appreciate that following process to determine of $F_X$ and $F_Y$ components of an applied force F, based upon force measurements using three half-bridges in which two half-bridges have matching resistor type that may or may not match the resistor type of a third half-bridge, is agnostic as to circumferential location of the half-bridges on the beam and is agnostic as to half-bridge type.

Let the applied force $F=(F_X, F_Y)$.
Then force along, $$FP_1 = F_X \cos \theta_1 + F_Y \sin \theta_1 \quad (1)$$

$$FP_2 = F_X \cos \theta_2 + F_Y \sin \theta_2 \quad (2)$$

$$FP_3 = F_X \cos \theta_3 + F_Y \sin \theta_3 \quad (3)$$

Let V1, V2, V3, be output voltages of $HB_A$, $HB_B$, $HB_C$ Then, $$V1 = g1 FP_1 + V\Delta_T \quad (4)$$

$$V2 = g2 FP_2 + V\Delta_T \quad (5)$$

$$V3 = g3 FP_3 + V\Delta_T \quad (6)$$

Where $V\Delta_T$ is voltage due to temperature gradient along the half bridge; $g_i$ is the sensitivity/gain of the HB toward force along $FP_i$.

Substituting in (1), (2), (3) into (4), (5), (6), we get, $$V1 = g1 \cos \theta_1 F_X + g1 \sin \theta_1 F_Y + V\Delta_T \quad (7)$$

$$V2 = g2 \cos \theta_2 F_X + g2 \sin \theta_2 F_Y + V\Delta_T \quad (8)$$

$$V3 = g3 \cos \theta_3 F_X + g3 \sin \theta_3 F_Y + V\Delta_T \quad (9)$$

Values for $g_i$ and $\theta i$ are known by design or calibration, and therefore, the unknowns are $F_X$, $F_Y$, and $V\Delta_T$. We have three equations and three unknowns. This is a straight forward linear algebra problem.

$$F_X = (V1(g3 \sin \theta_3 - g2 \sin \theta_2) + V2(g1 \sin \theta_1 - g3 \sin \theta_3) + V3(g2 \sin \theta_2 - g1 \sin \theta_1))/DEN \quad (10)$$

$$F_Y = (V1(g2 \cos \theta_2 - g3 \cos \theta_3) + V2(g3 \cos \theta_3 - g1 \cos \theta_1) + V3(g1 \cos \theta_1 - g2 \cos \theta_2))/DEN \quad (11)$$

Where.

$$DEN = g2g3(\sin \theta_2 \cos \theta_3 - \cos \theta_2 \sin \theta_3)$$

$$-g1g3(\sin \theta_1 \cos \theta_3 - \cos \theta_1 \sin \theta_3)$$

$$+g1g2(\sin \theta_1 \cos \theta_2 - \cos \theta_1 \sin \theta_2)$$

A value of gi for $HB_i$ depends on the type of HB.

If we assume sensitivity for all tension gauge HBs is g thene following is gi

If we assume value of gi is g for a tension gauge HB; then value of gi is $-\rho g$ if HB is compression gauge, where $\rho$ is the Poisson ratio of the material.

Thus, it will be appreciated that $F_X$ and $F_Y$ can be determined based upon each one of the following four combinations of three half-bridges (HBs) set forth in the following Table 2.

TABLE 2

| HB Combinatino No. | HB Combinations Suitable to Determine Both $F_X$ and $F_Y$ |
|---|---|
| 1 | $HB1_T$, $HB2_T$, $HB3_C$ |
| 2 | $HB3_C$, $HB4_C$, $HB1_T$ |
| 3 | $HB2_T$, $HB3_C$, $HB4_C$ |
| 4 | $HB1_T$, $HB4_C$, $HB2_T$ |

The following is an example of use of the process described with reference to FIG. 29 to determine example $F_X$ and $F_Y$ force component for the example of FIG. 26.

This example assumes the following values in Table 3:

TABLE 3

| Half-Bridge | Angle | Sensitivity/Gain |
|---|---|---|
| $HB1_T$ | $\theta1 = 90 - \theta$ | $g1 = g$ |
| $HB2_T$ | $\theta2 = 90 + \theta$ | $g2 = g$ |
| $HB3_C$ | $\theta3 = 90 - \theta$ | $g3 = -\rho g$ |
| $HB4_C$ | $\theta4 = 90 + \theta$ | $g4 = -\rho g$ |

The value $\theta$ is the half-angle (A/2) between the FP1 and FP2 force planes in FIG. 26. The value g is the sensitivity of the tension gauge half-bridge.

In this example, we use $HB1_T$, $HB2_T$, and $HB3_C$, with equations (10), (11) to determine, $$F_X = (V1 - V2)/2g \sin \theta$$

$$F_Y = (V1(1-\varphi) + V2(1+\rho) - 2V3)/2g \cos \theta(1+\rho)$$

Thus, the half-bridge combinations in the above Table 2 can be used to make redundant determinations of $F_X$ and $F_Y$. A comparison of the $F_X$ and $F_Y$ values determined based upon the above combinations of half-bridges can be used to determine whether the force sensor 21102 contains a malfunctioning resistor. If even a single resistor malfunctions, then then all four combinations would produce different $F_X$ and $F_Y$ values thus indicating failure. Since all four HBs would produce different results in the event of a failure, it will not be possible to determine the failing resistor.

Figure 30:
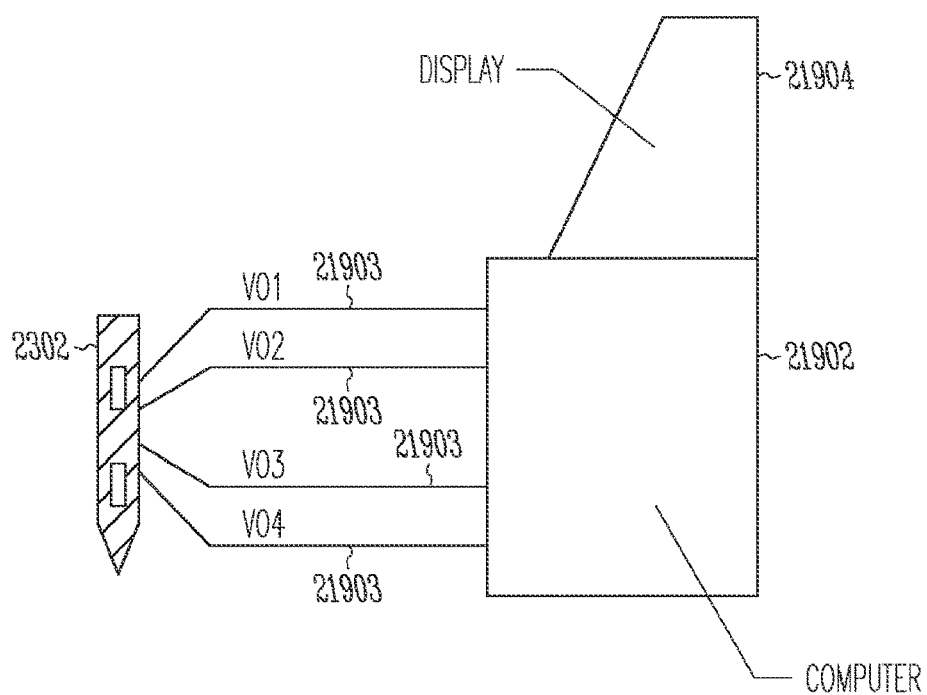
FIG. 30 is an illustrative drawing representing an computer system configured to monitor force sensor voltage measurements.
Figure 31:
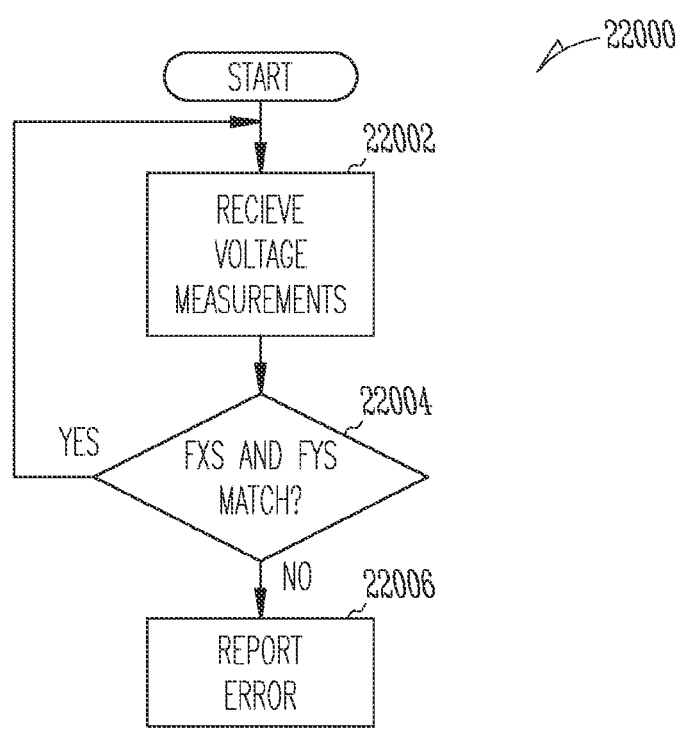
FIG. 31 is an illustrative flow diagram representing an example diagnostic process to detect an occurrence of a malfunctioning strain gauge resistor within a force sensor.

FIG. 30 is an illustrative drawing representing an computer system 21902 configured to monitor force sensor 2302 voltage measurements. An example computer system 21902 includes a display screen 21904. The computer system 21902 is configured to receive voltage measurements $V_{O1}$, $V_{O2}$, $V_{O3}$, and $V_{O4}$ on lines 21903 produced by the force sensor 2302. FIG. 31 is an illustrative flow diagram 22000 representing an example diagnostic process to detect an occurrence of a malfunctioning strain gauge resistor in a force sensor 2302 or 21102. The computer system 21902 is configured with computer readable instructions to perform steps of the diagnostic process 22000. At block 22002, the computer system receives voltage measurements $V_{O1}$, $V_{O2}$, $V_{O3}$, and $V_{O4}$. At block 22004, determines whether respective $F_X$ values match and whether respective $F_Y$ values match for each of the HB combinations 1-4 of Table 1. More particularly, for example the computer system 21902 uses voltage measurements from HB1, HB2, HB3, and HB4 to determine $F_X$ and $F_Y$. If values match, then control flows back to block 22002. If values do not match then block 22006 sends an electronic signal to report an error. In an example computer system 21902, the electronic signal causes display of an error message on the display screen 21904 It will be understood that the process 200 also can be performed for the sensor 21102 and the combinations 1-4 of Table 2.

Spread Bridge Reverse Disded XY Force Sensor

Figure 32A:
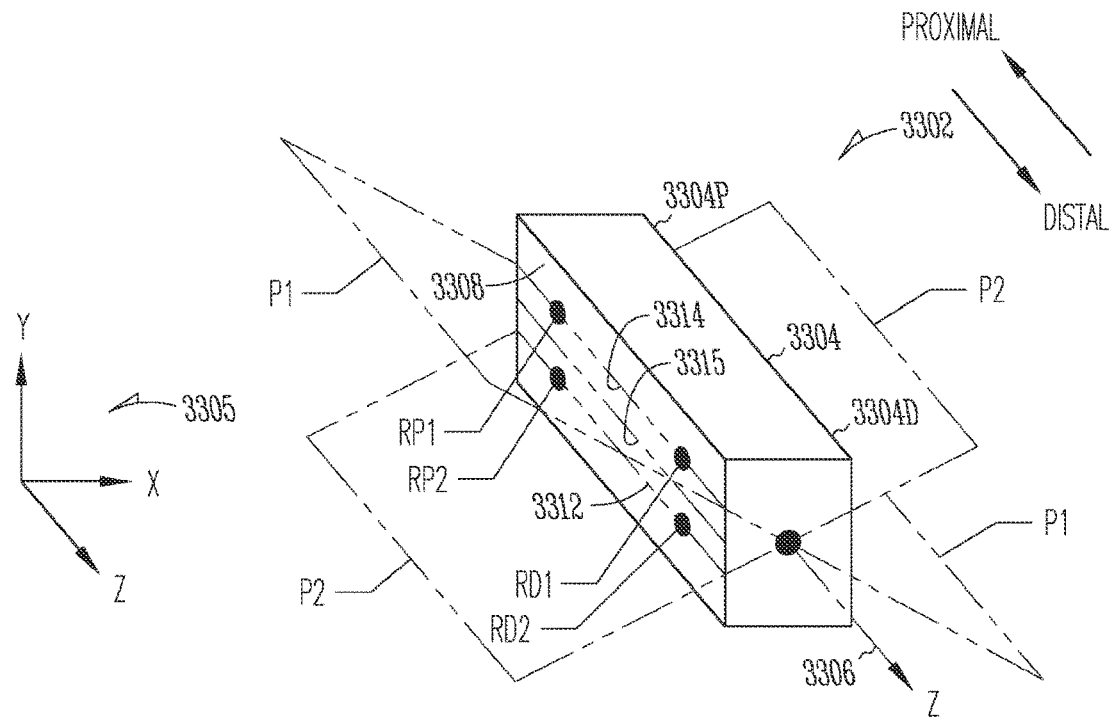
FIGS. 32A-32B show an illustrative top perspective view (FIG. 32A) and bottom perspective view (FIG. 32B) of an example force sensor that includes a rectangular beam with Wheatstone bridge circuits located on two reverse sides thereof.
Figure 32B:
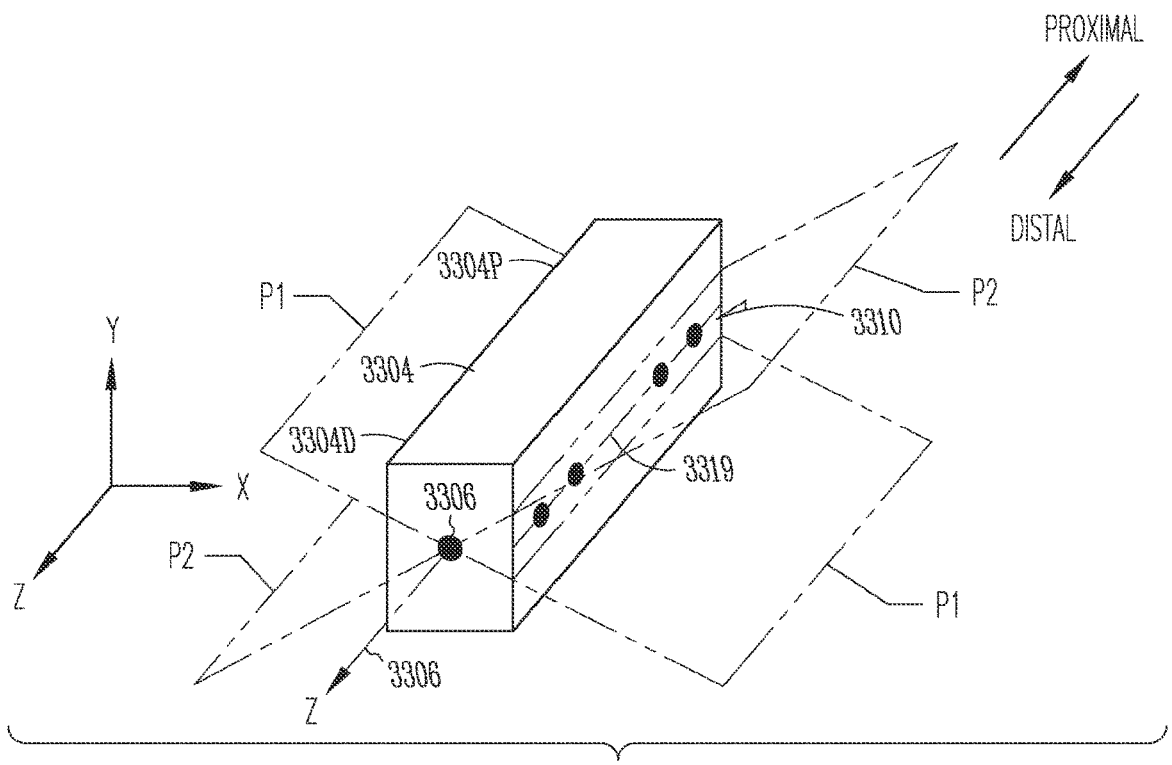

FIGS. 32A-32B show an illustrative top perspective view (FIG. 32A) and bottom perspective view (FIG. 32B) of an example force sensor 3302 that includes a rectangular beam 3304 with Wheatstone bridge circuits ('full-bridges') located on two reverse sides thereof. A first full-Wheatstone bridge includes first ($R_{P1}$), second ($R_{D1}$), third ($R_{P2}$), and fourth ($R_{D2}$) resistors. A second bridge includes fifth ($R_{P3}$), sixth ($R_{D3}$), seventh ($R_{P4}$), and eighth ($R_{D4}$) resistors. In an example first full-Wheatstone bridge 3352, the first and second resistors are coupled in a first half bridge, and the third and fourth resistors are coupled in a second half bridge. A second side 3308 of the beam 3304 shown in FIG. 32B faces in a direction that is reverse of a direction faced by a first side 3308 of the beam 3304 shown in FIG. 32A. An (X, Y, Z) beam coordinate system 3305 is shown to explain force directions relative to the beam 3304. An example beam 3304 can have a rectangular cross-section with planar side faces. More particularly, an example beam can have a square cross-section. The beam 3304 includes a proximal beam portion 3304P and a distal beam portion 3304D and includes a longitudinal center axis 3306 extending between the proximal and distal beam portions. Referring to FIG. 32A, a first proximal strain gauge resistor ('resistor') $R_{P1}$ and a second proximal resistor $R_{P2}$ are located at a proximal beam portion 3304P of a first side 3308 of the beam 3304. A first distal resistor $R_{D1}$ and a second distal resistor $R_{D2}$ are located at a distal beam portion 3304D of the first side 3308 of the beam 3304. Resistors $R_{P1}$-$R_{P2}$ and $R_{D1}$-$R_{D2}$ of a first set of resistors located on the first side 3308 of the beam are arranged in a first spread full-Wheatstone bridge, explained below in which a first pair of resistors $R_{P1}$-$R_{D1}$ and a second pair of resistors $R_{P2}$-$R_{D2}$ are located laterally spread apart from one another on opposite sides of a first side neutral axis 3315. Referring to FIG. 32B, a third proximal strain gauge resistor ('resistor') $R_{P3}$ and a fourth proximal resistor $R_{P4}$ are located at a proximal portion of a second side (also referred to as the 'reverse' side) of the beam. A third distal resistor $R_{D3}$ and a fourth distal resistor $R_{D4}$ are located at a distal portion of the second side of the beam. Resistors $R_{P3}$-$R_{P4}$ and $R_{D3}$-$R_{D4}$ of a second set of resistors are arranged in a second split full-Wheatstone bridge aligned with a third axis 3319, which is a neutral axis, of the second side of the beam.

As explained more fully below, the first and second full-bridge circuits are 'spread' in that portions of each bridge circuit are laterally spaced apart from one another on the beam 3304. For example, each full-bridge can include two half-bridges that are laterally spread apart from each other. An advantage of laterally spreading apart the half-bridges is that conductor traces that couple resistors to bias voltages or to one another, for example, can be routed to pass through the middle of a face of a beam 3304 or close a neutral axis of the beam 3304, on each face of the beam. Alternatively, in a circular cross-section beam (not shown), conductor traces advantageously can be routed along the neutral axes of individual half-bridges. This routing helps reduce strain on the traces and in turn improves the accuracy of the sensor, by rejecting unwanted signal.

The resistors can be placed on the beam 3304 manually or using automated machinery and can be adhered to the beam using an adhesive such as epoxy. Alternatively, the resistors can be deposited and laser etched directly on to the beam 3304. In both cases, an electrical circuit can be completed externally using wirebonds and flexible printed circuit.

As explained more fully below, a first pair of resistors $R_{P1}$-$R_{P2}$ and second pair of resistors $R_{D1}$-$R_{D2}$ located at the first 3304 side of the beam act as Y-direction force sensor elements, and third pair of resistors $R_{P3}$-$R_{P4}$ and a fourth pair of resistors $R_{D3}$-$R_{D4}$ located at the reverse second side of the beam act as X-direction force sensor elements. Referring again to FIG. 32A, the first proximal resistor $R_{P1}$ and the first distal resistor $R_{D1}$ are arranged upon the first side 3308 of the beam 3304 within a first imaginary plane P1 in which the longitudinal center axis 3306 extends and that defines a first lateral side axis 3312 at a location on the first side 3308 of the beam 3304 along which the first plane P1 intersects the first side 3308. The first later axis 3312 and the center axis 3306 extend parallel to one another and parallel to the first side neutral axis 3315. An example first lateral side axis 3312 extends through the first proximal resistor $R_{P1}$ and through the first distal resistor $R_{D1}$. Moreover, an example first lateral side axis 3312 bisects the example first proximal resistor $R_{P1}$ and bisects an example first distal resistor $R_{D1}$.

Still referring to FIG. 32A the second proximal resistor $R_{P2}$ and the second distal resistor $R_{D2}$ are arranged upon the reverse first side 3308 of the beam 3304 within a second imaginary plane P2 in which the longitudinal center axis 3306 extends and that defines a second lateral side axis 3314 at a location on the first side 3308 of the beam 3304 along which the second plane P2 intersects the first side 3308. The second later axis 3314 and the center axis 3306 extend parallel to one another and parallel to the first side neutral axis 3315. An example second lateral side axis 3314 extends through the second proximal resistor $R_{P2}$ and through the second distal resistor $R_{D2}$. Moreover an example second lateral side axis 3314 bisects the example second proximal resistor $R_{P2}$ and bisects an example second distal resistor $R_{D2}$.

Each of resistors of the first and second pairs of resistors $R_{P1}$-$R_{D1}$ and $R_{P2}$-$R_{D2}$ is the same type of strain gauge resistor. More particularity in the example force sensor 3302 described herein, the resistors $R_{P1}$-$R_{D1}$ and $R_{P2}$-$R_{D2}$ are tension type gauge resistors used to measure tensile strain. In an alternative example force sensor, the first and second pairs of resistors can be compression type gauge resistors used to measure compression strain. As used herein reference to a set resistors having 'matching type' refers to a set of resistors in which either all resistors are tension resistors or all resistors are compression resistors. Resistors that have matching type are more likely to have similar sensitivity and performance, making a sensor better suited for situation of low signal to noise ratio where the common mode cancellation is crucial and much better. In general, although either tension or compression gauge resistors can be used to determine X direction and Y direction forces, in general, tension strain gauge resistors are more sensitive than compression gauge resistors.

Referring to FIG. 32B, a third pair of resistors $R_{P3}$-$R_{D3}$ and fourth pair of resistors $R_{P4}$-$R_{D4}$ are arranged along a second side third axis 3319 of the second reverse side 3310 of the beam 3304. The second side third axis 3319 is a neutral axis that extends within the second side face, parallel to the center axis 3306, equidistant from the lateral edges of the second side. The third and fourth pairs of resistors include non-matching types of resistors. In particular, one of $R_{P3}$, $R_{P4}$ is a tension resistor and the other is a compression resistor, and one of $R_{D3}$, $R_{D4}$ is a tension resistor and the other is a compression resistor. The pitch between tension gauges and compression gauges also are matching.

Figure 33:
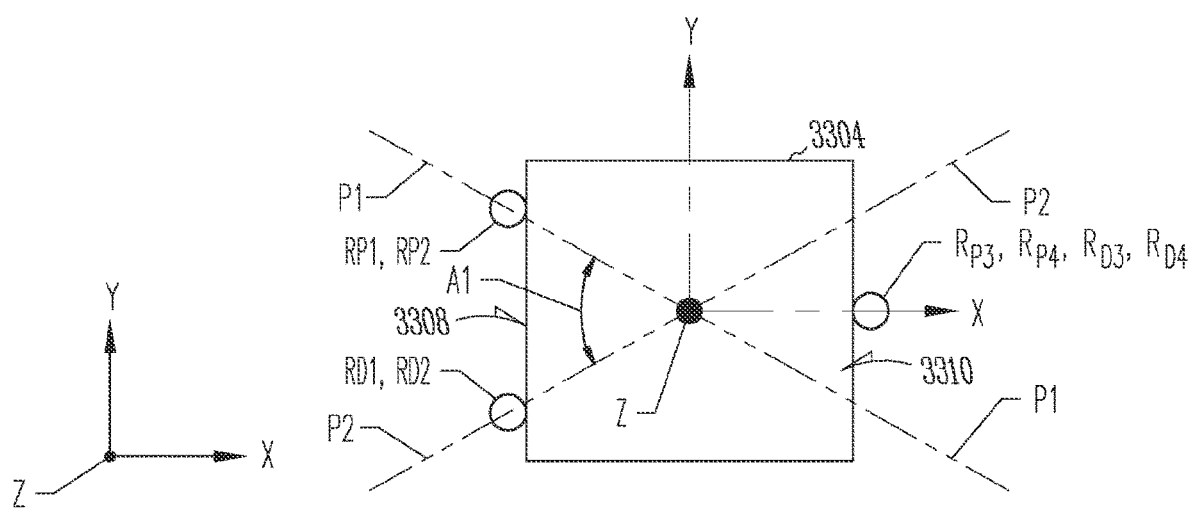
FIG. 33 is an illustrative proximal direction cross-section view of the example beam of FIGS. 32A-32B.
Figure 34B:
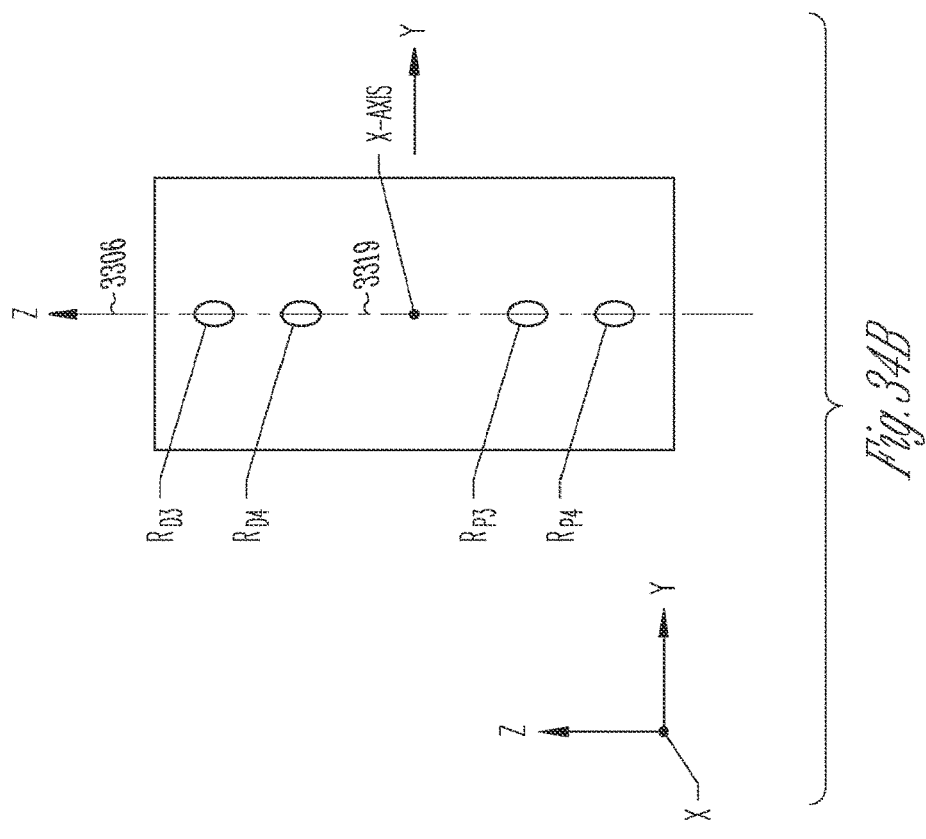
FIG. 34B is a side elevation view of the beam showing the second side of the beam.
Figure 34A:
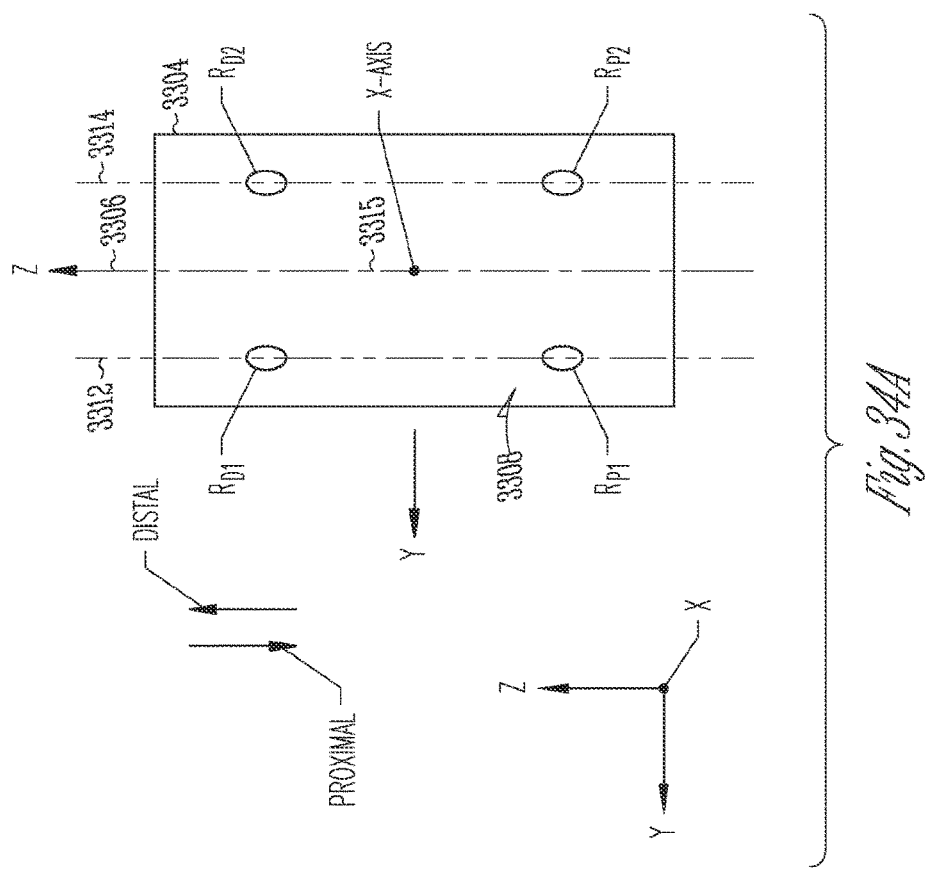
FIG. 34A is a side elevation view of the beam showing the first side of the beam.

FIG. 33 is an illustrative proximal direction cross-section view of the example beam 3304 of FIGS. 32A-32B. FIG. 34A is a side elevation view of the beam showing the first side 3308 of the beam 3304. FIG. 34B is a side elevation view of the beam showing the second side 3310 of the beam 3304.

Referring to FIG. 33, the proximal direction end view of the beam 3304 shows side views of the first and second planes P1, P2 that intersect one another along the longitudinal center axis 3306, which extends within both the first and second planes P1, P2. The (X, Y, Z) beam coordinate system 3305 is shown to explain force directions relative to the beam 3304. It is noted that in FIG. 33, the Z axis is shown emerging from the page. The first and second planes P1, P2 are separated from one another about the center axis 3306 by a first separation angle A1.

Referring to FIG. 34A, the first lateral side axis 3312 is shown extending through the first proximal resistor $R_{P1}$ and the first distal resistor $R_{D1}$ on the first side 3308 of the beam 3304. It is noted that in FIG. 34A, the X-axis extends into the page. The second lateral side axis 3314 is shown extending through the second proximal resistor $R_{P2}$ and the second distal resistor $R_{D2}$ on the first side 3308 of the beam 3304. Size of the first separation angle A1 corresponds to lateral spacing distance at the first side 3308, between the first and second lateral side axes 3312, 3314, and therefore, corresponds to lateral spacing between the a first resistor pair $R_{P1}$, $R_{D1}$ from the second resistor pair $R_{P2}$, $R_{D2}$. In an example force sensor the first lateral side axis 3312 and the second lateral side axis 3314 are equidistant from the first side neutral axis 3315, which extends within a first side face of the beam and is equidistant from the opposite lateral edges of the first side 3308.

Referring to FIG. 34B, the resistors $R_{P3}$-$R_{P4}$ and $R_{D3}$-$R_{D4}$ are aligned along the second third axis 3319, which extends within a second side face of the beam 3304 and is equidistant from the opposite lateral edges of the second side 3310. It is noted that in FIG. 34A, the X-axis emerges from the page.

Figure 37B:
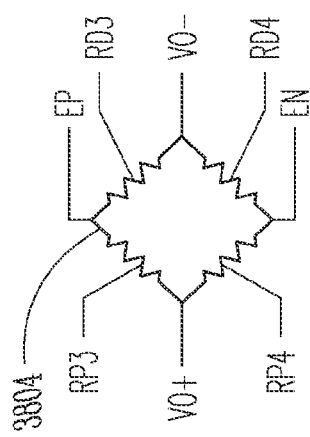
FIG. 37B is an illustrative schematic circuit diagram representation of the first example layout of the second full-bridge circuit.
Figure 37D:
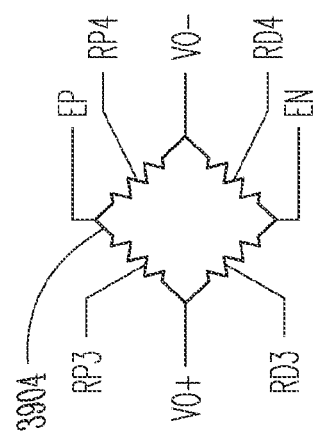
FIG. 37D is an illustrative schematic circuit diagram representation of the second example layout of the second full-bridge circuit.
Figure 37A:
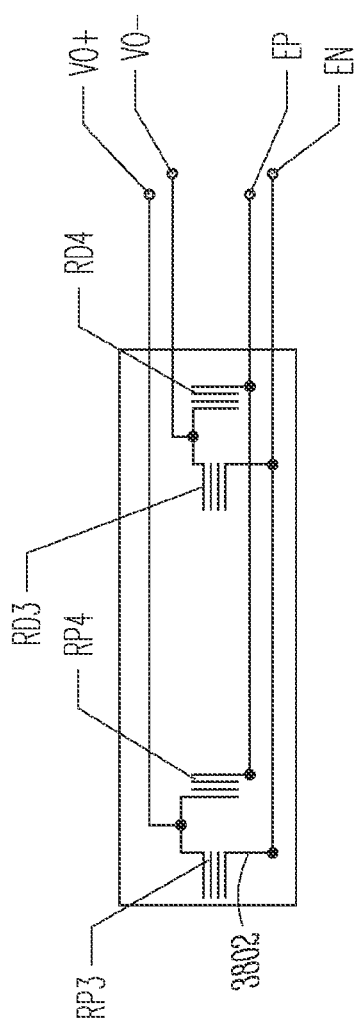
FIG. 37A is an illustrative side view of an example beam showing an example first circuit layout of a second full-Wheatstone bridge circuit located at the second side of the beam.
Figure 37C:
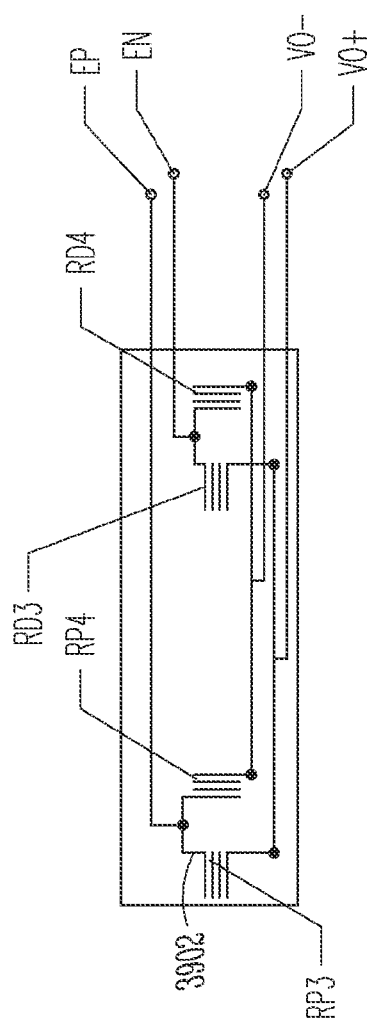
FIG. 37C is an illustrative side view of an example beam showing an example second layout of a second example full-Wheatstone bridge located at the second side of the beam 3304.

As explained below, resistors of the first bridge circuit are arranged laterally separated to measure force in a first direction perpendicular to the beam center axis 3306, based upon off-neutral axis forces imparted along the first and second planes P1, P2. As shown in FIG. 37A, lateral separation of the resistors of the first bridge 3352 makes possible routing of first center conductor traces 3356 parallel to the beam center axis 3306 in a region of the beam 3304 between proximal and distal resistors of a full-Wheatstone bridge.

Figure 35B:
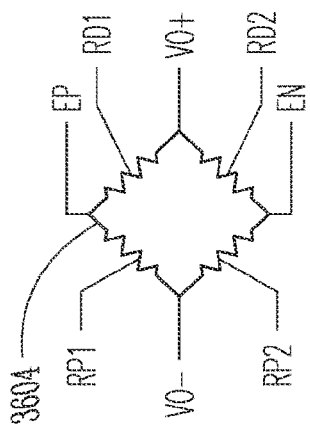
FIG. 35B is an illustrative first schematic circuit diagram representation of the first full-Wheatstone bridge layout topology.
Figure 35A:
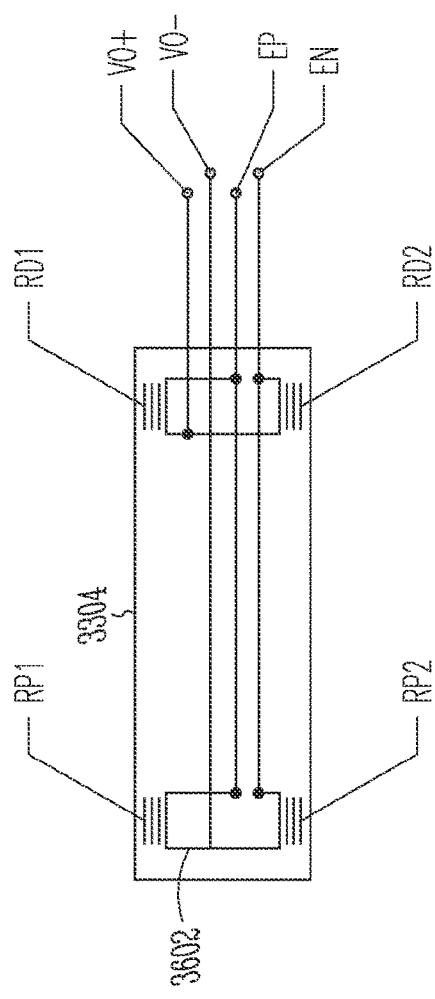
FIG. 35A is an illustrative side elevation view of an example beam showing a first example layout of a first full-Wheatstone bridge circuit.

FIG. 35A is an illustrative side elevation view of an example beam 3304 showing a first example layout of a first full-Wheatstone bridge 3602 that includes resistors $R_{P1}$-$R_{P2}$ and $R_{D1}$-$R_{D2}$. The first Wheatstone bridge layout is coupled in a first configuration to input bias voltage conductors (EP, EN) and output voltage conductors (Vo−, Vo+). FIG. 35B is an illustrative first schematic circuit diagram 3604 representation of the first full-Wheatstone bridge layout topology. Referring to FIGS. 35A-35B, the first proximal resistor $R_{P1}$ is electrically coupled between a positive first DC electrical potential (EP) and a second (also referred to as 'negative' potential) output Vo−. The second proximal resistor $R_{P2}$ is electrically coupled between a negative second DC electrical potential (EN) and the second output Vo−. The first distal resistor $R_{D1}$ is electrically coupled between the positive first DC electrical potential (EP) and a first output Vo+(also referred to as a 'positive' output). The second distal resistor $R_{D2}$ is electrically coupled between the negative second DC electrical potential (EN) and the first output Vo+.

Figure 36B:
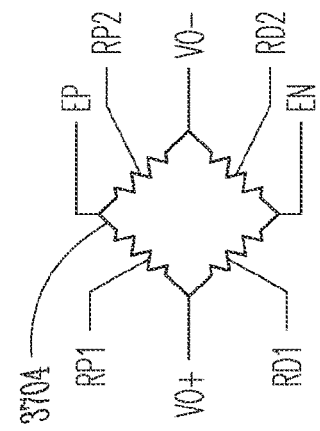
FIG. 36B is an illustrative first schematic circuit diagram representation of the alternative example second layout topology of the first full-Wheatstone bridge circuit.
Figure 36A:
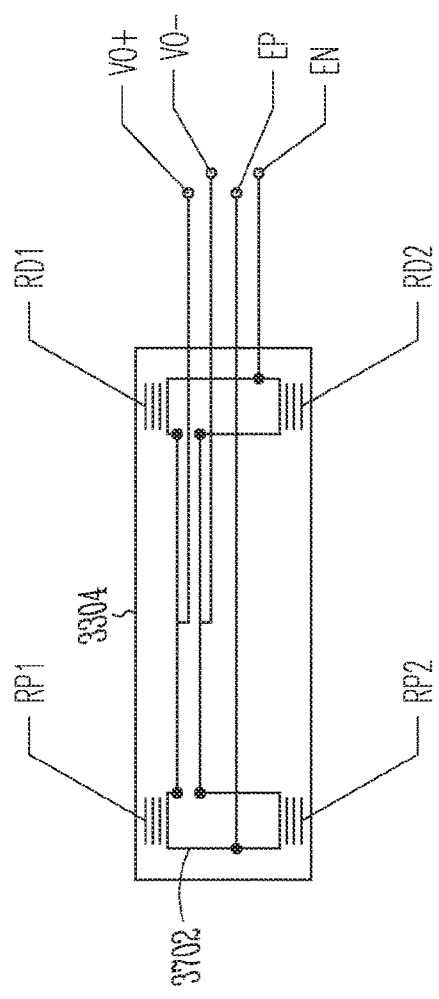
FIG. 36A is an illustrative side elevation view of an example beam showing an alternative second example layout of the first full-Wheatstone bridge circuit.

FIG. 36A is an illustrative side elevation view of an example beam 3304 showing an alternative second example layout of a first full-Wheatstone bridge 3702 that includes resistors $R_{P1}$-$R_{P2}$ and $R_{D1}$-$R_{D2}$. The second Wheatstone bridge layout is coupled in a second configuration to input bias voltage conductors (EP, EN) and output voltage conductors (Vo−, Vo+). FIG. 36B is an illustrative first schematic circuit diagram 3704 representation of the second alternative example layout of the first full-Wheatstone bridge circuit. Referring to FIGS. 36A-36B, the first proximal resistor $R_{P1}$ is electrically coupled between the positive first DC electrical potential (EP) and the first output Vo+. The second proximal resistor $R_{P2}$ is electrically coupled between the positive first DC electrical potential (EP) and the second output Vo−. The first distal resistor $R_{D1}$ is electrically coupled between the negative second DC electrical potential (EN) and the first output Vo+. The second distal resistor $R_{D2}$ is electrically coupled between the negative second DC electrical potential (EN) and the second output Vo−.

In general, the layout in FIG. 35A is better for reducing the number of traces that must span the length of the beam and also reduces the effect of traces picking up strain. On the other hand, the layout in FIG. 36A layout is preferred if the force sensor uses half bridge voltage measurements. FIG. 37A is an illustrative side view of an example beam 3304 showing an example layout of a second example full-Wheatstone bridge 3802 located at the second side 3310 of the beam 3304 and including resistors $R_{P3}$-$R_{P4}$ and $R_{D3}$-$R_{D4}$. Proximal resistor $R_{P3}$ is located proximal of proximal resistor $R_{P4}$. Distal resistor $R_{D3}$ is located proximal of distal resistor $R_{D4}$. Proximal resistor $R_{P3}$ and distal resistor $R_{D3}$ are tension gauge resistors and proximal resistor $R_{P4}$ and distal resistor $R_{D4}$ are compression gauge resistors. In the second bridge's first layout shown in FIG. 37A, the second bridge is coupled in a first configuration to input bias voltage conductors (EP, EN) and to output voltage conductors (Vo−, Vo+). FIG. 37B is an illustrative schematic circuit diagram 3804 representation of the first example layout of the second full-bridge circuit. Referring to FIGS. 37A-37B, the third proximal resistor $R_{P3}$ is electrically coupled between the negative second DC electrical potential (EN) and the first output Vo+. The fourth proximal resistor $R_{P4}$ is electrically coupled between the positive first DC electrical potential (EP) and the first output Vo+. The third distal resistor $R_{D3}$ is electrically coupled between the negative second DC electrical potential (EN) and the second output Vo−. The fourth distal resistor $R_{D4}$ is electrically coupled between the positive first DC electrical potential (EP) and the second output Vo−.

FIG. 37A is an illustrative side view of an example beam 3304 showing an example second layout of a second example full-Wheatstone bridge 3902 located at the second side 3310 of the beam 3304 and including resistors $R_{P3}$-$R_{P4}$ and $R_{D3}$-$R_{D4}$. Proximal resistor $R_{P3}$ is located proximal of proximal resistor $R_{P4}$. Distal resistor $R_{D3}$ is located proximal of distal resistor $R_{D4}$. Proximal resistor $R_{P3}$ and distal resistor $R_{D3}$ are tension gauge resistors and proximal resistor $R_{P4}$ and distal resistor $R_{D4}$ are compression gauge resistors. In the second bridge's second layout shown in FIG. 37A, the second full-bridge is coupled in a first configuration to input bias voltage conductors (EP, EN) and to output voltage conductors (Vo−, Vo+). FIG. 37B is an illustrative schematic circuit diagram 904 representation of the second example layout of the second full-bridge circuit. Referring to FIGS. 37A-37B, the third proximal resistor $R_{P3}$ is electrically coupled between the positive first DC electrical potential (EP) and the first output Vo+. The fourth proximal resistor $R_{P4}$ is electrically coupled between the positive first DC electrical potential (EP) and the second output Vo−. The third distal resistor $R_{D3}$ is electrically coupled between the negative second DC electrical potential (EN) and the first output Vo+. The fourth distal resistor $R_{D4}$ is electrically coupled between the negative second DC electrical potential (EP) and the second output Vo−.

FIG. 38A is an illustrative side view of an example beam 3304 showing a spread layout of the Wheatstone bridge 3352 located on the first side 3308 of the beam 3304 and showing and routing of center conductor traces 3356 that extend within the center of the bridge, between proximal and distal resistors of the bridge. The bridge 3352 includes $R_{P1}$, $R_{P2}$ and distal resistors $R_{D1}$, $R_{D2}$ and has a first neutral axis 3362 that extends parallel to the beam axis 3306 between proximal resistors $R_{P1}$, $R_{P2}$ and the distal resistors $R_{D1}$, $R_{D2}$. In an example bridge, the first neutral is equally spaced from each of $R_{P1}$ and $R_{P2}$ and is equally spaced from each of $R_{D1}$ and $R_{D2}$. The first bridge 3352 is longitudinally split in that the proximal resistors $R_{P1}$, $R_{P2}$ are longitudinally separated from the distal resistors $R_{D1}$, $R_{D2}$. The first bridge is laterally spread in that proximal resistors $R_{P1}$, $R_{P2}$ are laterally spread apart and the distal resistors $R_{D1}$, $R_{D2}$ are laterally spread apart from one another.

It will be appreciated that since the resistors of the first full-Wheatstone bridge 3352 are laterally spread apart, they do not occupy the first neutral axis 3362. Therefore conductor traces can be routed close to and in parallel with the first neutral axes 3362, which can reduce the amount of strain imparted to the traces. Also, routing of traces along the neutral axis of a bridge circuit can be easier to produce to manufacture or assembly.

An example first full-bridge includes a first group of center conductor traces 3356 that extend longitudinally along a center portion of the first bridge 3352, parallel to the first neutral axis 3362, along a region of an outer surface of the beam 3304 between the pair of proximal resistors $R_{P1}$, $R_{P2}$ and the pair of distal resistors $R_{D1}$, $R_{D2}$ of the first bridge 3352. The first group of center traces 3356 include trace segments 3356-1 coupled to a first positive output voltage VO1+. The first group of center traces 3356 includes trace segments 3356-1 coupled to a first negative voltage output VO1−. The first group of center traces 3356 include trace segments 3356-3 coupled to a negative voltage potential EN.

FIG. 38B is an illustrative first schematic circuit diagram representation of the first and second full-Wheatstone bridges of FIG. 38A. The full-Wheatstone bridge 3352 includes $R_{P1}$ and $R_{D1}$ coupled between EP and EN to provide a first half-bridge voltage divider circuit that includes a trace conductor coupled to the first positive output voltage VO1+. The first full-Wheatstone bridge 3352 also includes $R_{P2}$ and $R_{D2}$ coupled between EP and EN to provide a second half-bridge voltage divider circuit that includes a trace conductor coupled to the first negative output voltage VO1−.

Figure 39A:
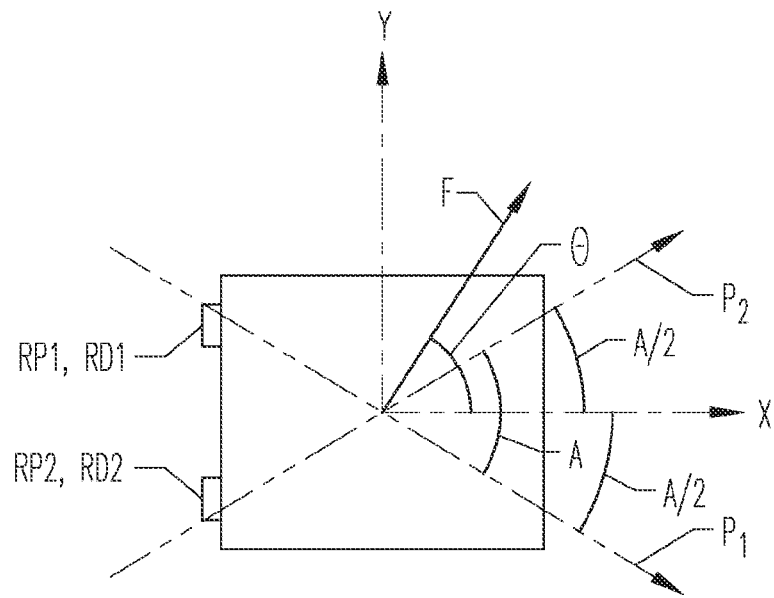
FIG. 39A is an illustrative cross-sectional end view of the example beam of FIG. 33 indicating the resistors on the first side and indicating a first plane force and a second plane force.
Figure 39B:
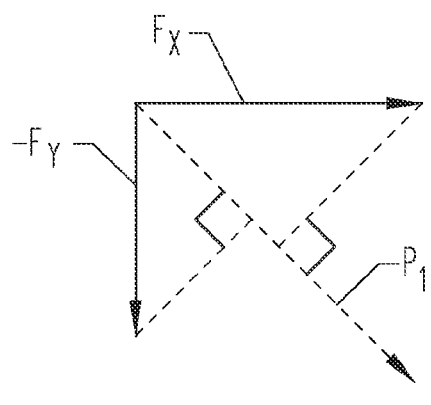
FIG. 39B is an illustrative force diagram that indicates X and Y force components of the first plane force imparted to a first proximal resistor and a first distal resistor in response to an applied force.
Figure 39C:
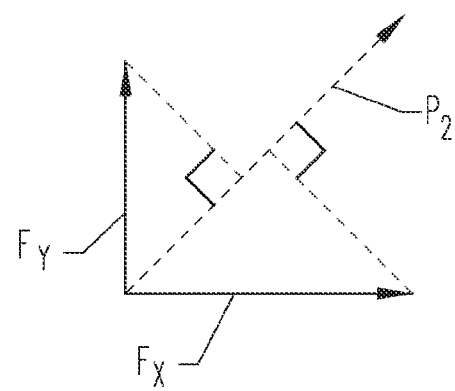
FIG. 39C is an illustrative force diagram that indicates X and Y force components of the second plane force imparted to a second proximal resistor and second distal resistor in response to an applied force.

FIG. 39A is an illustrative cross-sectional end view of the example beam 3304 of FIG. 33 indicating the resistors on the first side and indicating a first plane force FP1 and a second plane force FP2. FIG. 39B is an illustrative force diagram that indicates X and Y force components of the first plane force FP1 imparted to the first proximal resistor $R_{P1}$ and the first distal resistor $R_{D1}$ in response to an applied force F. FIG. 39C is an illustrative force diagram that indicates X and Y force components of the second plane Y-force FP2 imparted to the second proximal resistor $R_{P2}$ and the second distal resistor $R_{D2}$ in response to the applied force F.

In an example force sensor 3302, resistance values of the first pair of resistors, $R_{P1}$, $R_{D1}$, match resistance values of the second pair of resistors, $R_{P2}$, $R_{D2}$. In an example force sensor 3302, the first and second pairs of resistors are positioned upon an example beam 3304, such that an applied force F imparted to the example beam 3304 imparts a first plane strain force FP1 to the first pair of resistors within the first plane P1 and imparts a second plane strain force FP2 to the second pair of resistors within the second plane P2. It will be appreciated that the first plane strain force FP1 is an off-axis force since it is a force imparted along the first lateral side axis 3312, which is laterally offset from a neutral axis 3315 of the first bridge 3352. Likewise, it will be appreciated that the second plane strain force FP2 is an off-axis force since it is a force imparted along the second lateral side axis 3314, which is latterly offset from a neutral axis 3315 of the first bridge 3352. The first and second pairs of resistors are positioned upon an example beam 3304, such that a magnitude of the first plane strain force FP1 matches a magnitude of the second plane strain force FP2. Force directions of the first plane strain force FP1 and second plane strain force FP2 are separated from one another by the first separation angle 'A'.

An advantage of using strain gauge resistors of the same type is that magnitude of a force imparted perpendicular to the center axis 3306 of a beam 3304 can be determined based upon a difference in magnitude of off-axis forces imparted to the different half-bridges of a full-bridge located on the beam. In the example force sensor 3302, magnitude of a Y-direction force component $F_Y$ imparted to the beam 3304 by an applied force F can be determined based upon difference between the first off-axis force FP1 and the second off-axis force FP2 as follows.

Let A be angle between P1 and P2.
Let X axis bisect the angle A. Therefore, an angle between P1 and X is A/2 and an angle between P2 and X is A/2.
Let θ be an angle between the X axis and an applied force F.
Force along X axis $F_x$=F cos θ
Force along y axis $F_y$=F sin θ
Referring to FIG. 37B, force along P1=$F_x$ cos A/2+$F_y$ cos (90+A/2)=FP1
Referring to FIG. 9C, force along P2=$F_x$ cos A/2+$F_y$ cos (90−A/2)=FP2
FP1=$F_x$ cos A/2+$F_y$ cos (90+A/2)
FP2=$F$, cos A/2+$F_y$ cos (90−A/2)
Using cos (θ)=−cos (180−θ)
we get
FP2=$F_x$ cos A/2−$F_y$ cos (90+A/2)
When we subtract FP1 and FP2
we get FP1−FP2=$F_x$ cos A/2+$F_y$ cos (90+A/2)−$F_x$ cos A/2+$F_y$ cos (90+A/2)
Therefore, FP1−FP2=2 $F_y$ cos (90+A/2)
Therefore, FP1−FP2 ∝$F_y$
Thus, the difference between FP1 and FP2 is proportional to the Y-direction force component $F_Y$ imparted to the beam by the applied force F.

Moreover, it will be appreciated that,
$F_Y$ α $V_{S1O+}$−$V_{S1O−}$,
where $V_{S1O+}$ is positive output voltage and $V_{S1O−}$ is negative output voltage of the first bridge circuit 3352, and $V_{S1O+}$−$V_{S1O−}$ is a voltage offset produced by the first bridge circuit 3352 located on the first side 3308 of the beam 3304.

Figure 40:
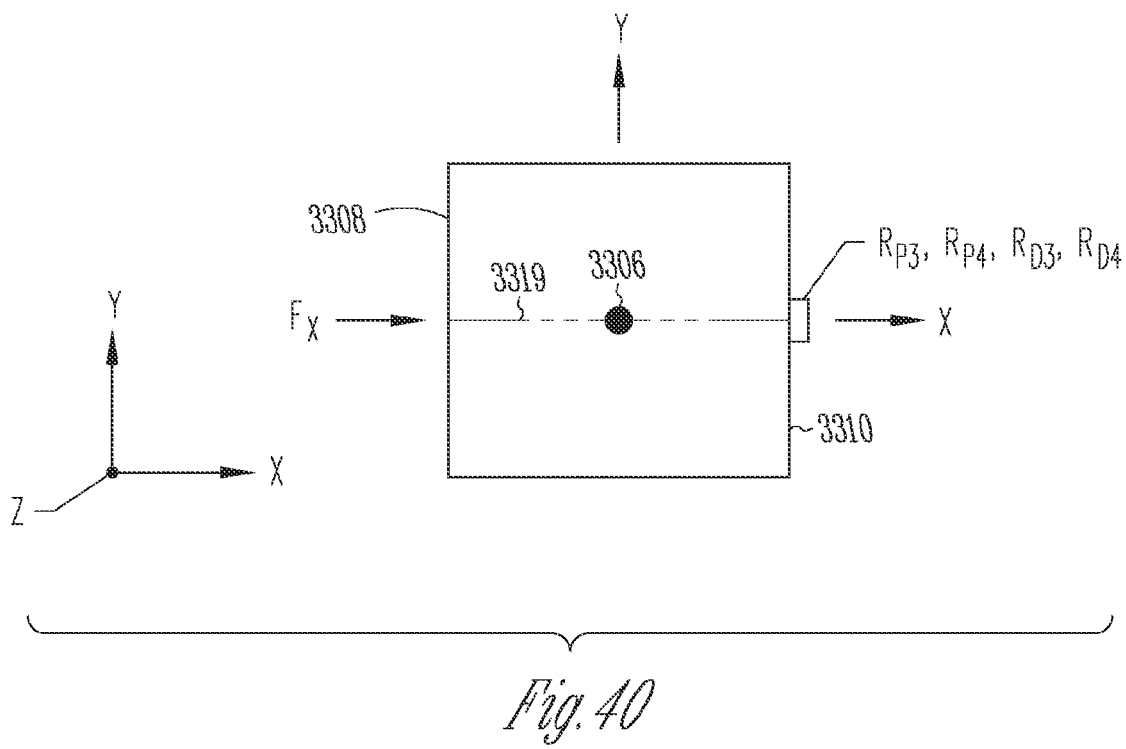
FIG. 40 is an illustrative proximal direction cross-section view of the example beam of FIG. 33 indicating the resistors indicating an X-axis force.

FIG. 40 is an illustrative proximal direction cross-section view of the example beam 3304 of FIG. 33 indicating the resistors $R_{P3}$, $R_{P4}$, $R_{D3}$, $R_{D4}$, of an example second full bridge 3802 or 3902 on the second side 3310 and indicating an X-axis force $F_X$. The example second full-bridge 3802 or 3902 measures the X-axis force, which is perpendicular to the longitudinal axis 3306 and to the third axis 3319 of the second side 3310. An example full bridge circuit includes tension resistors and compression resistors longitudinally aligned parallel with a beam center axis and along a neutral axis is disclosed in PCT/US2018/061113 filed Nov. 14, 2018, which is expressly incorporated herein in its entirety by this reference.

Figure 41:
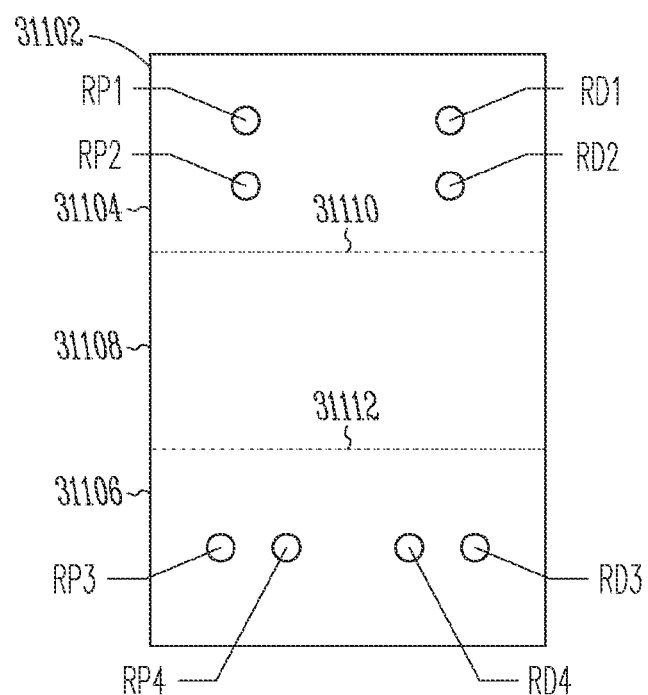
FIG. 41 is an illustrative drawing representing a metal sheet containing cut-outs that define example resistors for assembly into respective first and second full-Wheatstone bridges on reverse-facing first and second sides of a beam.

FIG. 41 is an illustrative drawing representing a metal sheet 31102 containing cut-outs that define example resistors $R_{P1}$-$R_{P4}$ and $R_{D1}$-$R_{D4}$ for assembly into respective first and second full-Wheatstone bridges on reverse-facing first and second sides 3308, 3310 of a beam 3304. A first region 31104 of the metal sheet 31102 includes resistors $R_{P1}$-$R_{P2}$ and $R_{D1}$-$R_{D2}$ to be coupled within a first full-bridge to be located at a first side 3308 of an example beam. A second region 31106 of the metal sheet includes resistors $R_{P3}$-$R_{P4}$ and $R_{D3}$-$R_{D4}$ to be coupled within a second full-bridge to be located at a reverse second side 3310 of an example beam 3304. A middle third region 31108 that extends between the first and second regions and is sized to overlay a third intermediate side 3320 of the beam 3304 located between the first and second sides 3308, 3310 of the beam 3304. A first fold line 1110 separates the first region from the second region and a second fold line 1112 separates the second region from the middle region.

Figure 42A:
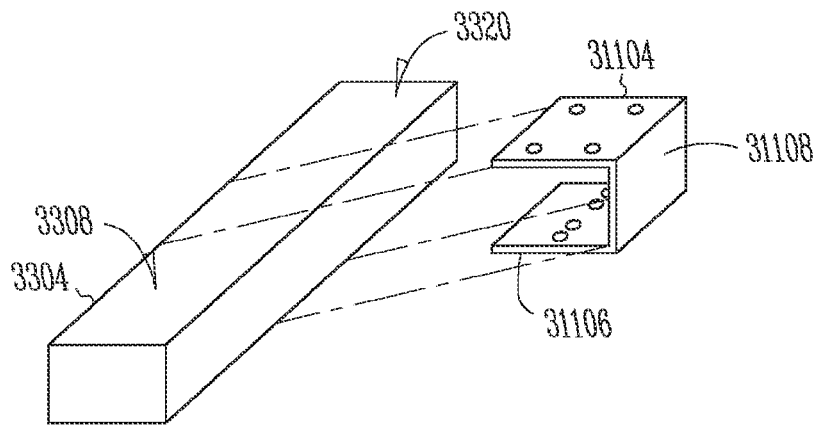
FIG. 42A is an illustrative drawing representing a process of wrapping the metal sheet about an example beam to position a first set of resistors at the first side of the beam and to position a second set of resistors at e second side of the beam.
Figure 42B:
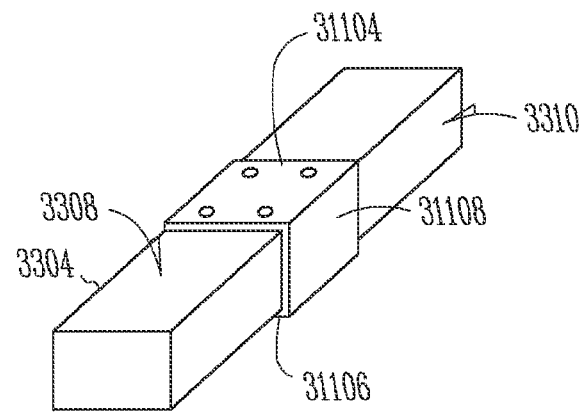
FIG. 42B is an illustrative top perspective view of the beam with the metal sheet wrapped around three sides thereof.
Figure 42C:
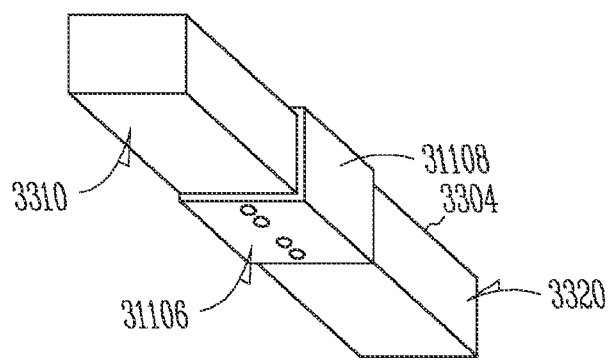
FIG. 42C is an illustrative bottom perspective view of the beam with the metal sheet wrapped around three sides thereof.

FIG. 42A is an illustrative drawing representing a process of folding the metal sheet 31102 along the first and second fold lines 1110, 1112 to wrap the first, second, and third 31104, 31104, 31106 regions of the metal sheet 31102 about an example beam 3304 to position a first set of resistors, $R_{P1}$-$R_{P2}$ and $R_{D1}$-$R_{D2}$, at the first side 3308 of the beam 3304 and to position a second set of resistors $R_{P3}$-$R_{P4}$ and $R_{D3}$-$R_{D4}$ at the second side 3310 of the beam 3304, and to position the middle third region 31108 over the third intermediate side 3320 of the beam 3304. FIG. 42B is an illustrative top perspective view of the beam 3304 with the metal sheet 31102 wrapped around three sides thereof. In particular, FIG. 42B shows the first region 31104 of the metal sheet 31102 overlaying the first side 3310 of the beam 3304 to position the first set of resistors at the first side. FIG. 42C is an illustrative bottom perspective view of the beam 3304 with the metal sheet 31102 wrapped around three sides thereof. In particular, FIG. 42C shows the second region 31106 of the metal sheet 31102 overlaying the second side 3310 of the beam 3304 to position the second set of resistors at the second side. In an example rectangular beam, the first side includes a first face of the beam and the second side includes a second side face that is reverse to the first side face.

Although illustrative examples have been shown and described, a wide range of modification, change and substitution is contemplated in the foregoing disclosure and in some instances, some features of the examples may be employed without a corresponding use of other features. For example, a rectangular beam is described herein. However, beams having alternate example beams having circular cross sections or octagonal cross-sections can be used. More generally, an example beam can be used that has a second area moment of inertia that is isotropic for all axes within a cross section plane extending through a proximal portion of the beam perpendicular to the center axis of the beam and that also is isotropic for all axes within a distal cross section plane extending through a distal portion of the beam perpendicular to the center axis of the beam.

The second area moment of inertia requirement is expressed as, $$I_X = I_Y$$

where $I_X$ represents a moment of inertia about an arbitrarily chosen X axis lying on the plane perpendicular to the central axis and $I_Y$ represents a moment of inertia about an axis that lies on the same plane but perpendicular to the X axis and $$I_{XY} = 0,$$

where $I_{XY}$ represents a product moment of inertia for the cross section of the beam.

Figure 43:
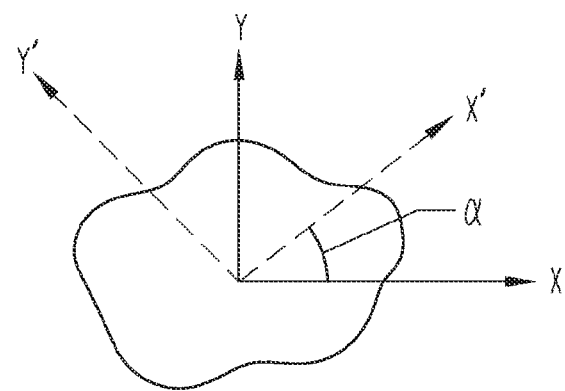
FIG. 43 is an illustrative cross-sectional view of a beam.

FIG. 43 is an illustrative cross-sectional view of a beam 1500 having cross-section area A. For cross section A of the beam 1500, Let $I_x$, $I_y$, $I_{xy}$ be the 2nd moment of Inertia where $I_x = \iint x^2 dA$ $$I_y = \iint y^2 dA$$

$$I_{xy} = \iint xy\, dA$$

For a new frame inclined at angle θ

$$x^1 = x\cos\theta + y\sin\theta$$

$$y^1 = Y\cos\theta - x\sin\theta$$

$$\therefore I_{x'} = \iint x'^2 dA = \frac{I_x + I_y}{2} + \frac{I_x - I_y}{2}\cos2\sigma - I_{xy}\sin2\theta$$

For I to be isotropic in all directions, the requirement is that, $$I_x = I_y \text{ and } I_{xy} = 0$$

The second area moment of inertia requirement is expressed as, $$I_X = I_Y$$

where $I_X$ represents a moment of inertia about an arbitrarily chosen X axis lying on the plane perpendicular to the central axis and $I_Y$ represents a moment of inertia about an axis that lies on the same plane but perpendicular to the X axis and $$I_{XY} = 0,$$

where $I_{XY}$ represents a product moment of inertia for the cross section of the beam.

EXAMPLES

Example 1 can include a force sensor comprising: a rectangular beam having a proximal portion and a distal portion and having a longitudinal center axis extending between the proximal portion and the distal portion; a first full-bridge circuit including: a first gauge resistor ('first resistor') and a second gauge resistor ('second resistor') coupled to provide a first voltage divider output; and a third gauge resistor ('third resistor') and a fourth gauge resistor ('fourth resistor') coupled to provide a second voltage divider output; a second full-bridge circuit including: a fifth gauge resistor ('fifth resistor') and a sixth gauge resistor ('sixth resistor') coupled to provide a third voltage divider output; and a seventh gauge resistor ('seventh resistor') and an eighth gauge resistor ('eighth resistor') coupled to provide a fourth voltage divider output; wherein the first, second, third, fourth, fifth, sixth, seventh, and eighth resistors have matching resistor type; wherein the first, second, third, and fourth resistors are located at a first side face of the beam, such that a voltage offset between the first and second voltage divider outputs represents magnitude of a first force imparted to the beam in a first force direction normal to the longitudinal axis and parallel to a face of the beam; and wherein the fifth, sixth, seventh, and eighth resistors are located at a second side face of the beam adjacent to the first side face, such that a voltage divider offset between the third and fourth voltage divider outputs represents magnitude of a second force imparted to the beam in a second force direction normal to the longitudinal axis and normal to the first force direction.

Example 2 can include the subject matter of Example 1 wherein the first, second, third, fourth, fifth, sixth, seventh, and eighth resistors are strain type resistors.

Example 3 can include the subject matter of Example 1 wherein the first, third, fifth, and seventh resistors are located at the proximal portion of the beam; and wherein the second, fourth, sixth, and eighth resistors are located at the proximal portion of the beam.

Example 4 can include the subject matter of Example 3 wherein the first and third resistors have matching values, second and fourth resistors have matching values, the fifth and seventh resistors have matching values, and the sixth and eighth resistors have matching values.

Example 5 can include the subject matter of Example 3 wherein the first and third resistors have matching longitudinal locations of the beam, second and fourth resistors have matching longitudinal locations of the beam, the fifth and seventh resistors have matching longitudinal locations of the beam, and the sixth and eighth resistors have matching longitudinal locations of the beam.

Example 6 can include a force sensor comprising: a beam having a proximal portion and a distal portion and having a longitudinal center axis extending between the proximal portion and the distal portion; a first full-bridge circuit including: a first gauge resistor ('first resistor') and a second gauge resistor ('second resistor') coupled to provide a first voltage divider output, arranged to extend along a first side axis that extends along the beam parallel to the longitudinal center axis; and a third gauge resistor ('third resistor') and a fourth gauge resistor ('fourth resistor') coupled to provide a second voltage divider output, arranged to extend along a second side axis that extends along the beam parallel to the longitudinal center axis; a second full-bridge circuit including: a fifth gauge resistor ('fifth resistor') and a sixth gauge resistor ('sixth resistor') coupled to provide a third voltage divider output, arranged to extend along a third side axis that extends along the beam parallel to the longitudinal center axis, and a seventh gauge resistor ('seventh resistor') and an eighth gauge resistor ('eighth resistor') coupled to provide a fourth voltage divider output, arranged to extend along a fourth side axis that extends along the beam parallel to the longitudinal center axis; wherein the first, second, third, fourth, fifth, sixth, seventh, and eighth resistors have matching resistor type; wherein the first and second resistors that extend along the first side axis, and the third and fourth resistors that extend along the second side axis, are positioned upon the beam such that a voltage offset between the first and second voltage divider outputs represents magnitude of a first force imparted to the beam in a first force direction normal to the longitudinal axis and normal to the first and second side axes and parallel to the third and fourth side axis; and wherein the fifth and sixth resistors that extend along the third side axis, and the seventh and eighth resistors that extend along the fourth side axis, are positioned upon the beam such that a voltage offset between the third and fourth voltage divider outputs represents magnitude of a second force imparted to the beam in a second force direction normal to the longitudinal axis, parallel to the first and second axes and normal to the third and fourth side axes.

Example 7 can include the subject matter of Example 6 wherein the first, second, third, fourth, fifth, sixth, seventh, and eighth resistors are strain type resistors.

Example 8 can include the subject matter of Example 6 wherein the first, second, third, fourth, fifth, sixth, seventh, and eighth resistors have matching resistor values.

Example 9 can include the subject matter of Example 6 wherein the first, third, fifth, and seventh resistors are located at the proximal portion of the beam; and wherein the second, fourth, sixth, and eighth resistors are located at the proximal portion of the beam.

Example 10 can include the subject matter of Example 6 wherein the first, third, fifth, and seventh resistors are positioned at matching longitudinal locations of the beam; and wherein the second, fourth, sixth, and eighth resistors are positioned at matching longitudinal locations of the beam.

Example 11 can include the subject matter of Example 6 wherein the first and third resistors are located in a proximal cross-section plane of the beam that is normal to the center axis and that has a second area moment of inertia that is isotropic for all axes within the proximal cross-section plane that pass through the longitudinal center axis; wherein the fifth and seventh resistors are located in a proximal cross-section plane of the beam that is normal to the center axis and that has a second area moment of inertia that is isotropic for all axes within the proximal cross-section plane that pass through the longitudinal center axis; wherein the second and fourth resistors are located in a distal cross-section plane of the beam that is normal to the center axis and that has a second area moment of inertia that is isotropic for all axes within the distal cross-section plane that pass through the longitudinal center axis; and wherein the sixth and eighth resistors are located in a distal cross-section plane of the beam that is normal to the center axis and that has a second area moment of inertia that is isotropic for all axes within the distal cross-section plane that pass through the longitudinal center axis.

Example 12 can include the subject matter of Example 6 wherein the first side axis extends within a first plane that includes the longitudinal center axis; wherein the first side axis extends within a first plane that includes the longitudinal center axis; wherein the second force direction bisects a first separation angle between the first and second planes; wherein the third side axis extends within a third plane that includes the longitudinal center axis; wherein the fourth side axis extends within a fourth plane that includes the longitudinal center axis; and wherein the first force direction bisects a second separation angle between the third and fourth planes.

Example 13 can include the subject matter of Example 12 wherein the first separation angle equals the second separation angle.

Example 14 can include the subject matter of Example 6 wherein the first gauge resistor, the second gauge resistor, the third gauge resistor, and the fourth gauge resistor are located at respective locations of the beam that have matching cross sections; and wherein the fifth gauge resistor, the sixth gauge resistor, the seventh gauge resistor, and the eighth gauge resistor are located at respective locations of the beam that have matching cross sections.

Example 15 can include the subject matter of Example 9 wherein the first gauge resistor, the second gauge resistor, the third gauge resistor, and the fourth gauge resistor are located at respective locations of the beam that have matching cross sections; and wherein the fifth gauge resistor, the sixth gauge resistor, the seventh gauge resistor, and the eighth gauge resistor are located at respective locations of the beam that have matching cross sections.

Example 16 can include, for use with a rectangular beam having a proximal portion and a distal portion and having a longitudinal center axis extending between the proximal portion and the distal portion, a metal sheet comprising: a first cut-out section configured to overlay a first side face of the beam, including: a first gauge resistor ('first resistor') and a second gauge resistor ('second resistor') coupled to provide a first voltage divider output; and a third gauge resistor ('third resistor') and a fourth gauge resistor ('fourth resistor') coupled to provide a second voltage divider output; a second cut-out section configured to overlay a second side face of the beam adjacent to the first side face of the beam, including: a fifth gauge resistor ('fifth resistor') and a sixth gauge resistor ('sixth resistor') coupled to provide a third voltage divider output; and a seventh gauge resistor ('seventh resistor') and an eighth gauge resistor ('eighth resistor') coupled to provide a fourth voltage divider output, arranged to extend along a fourth side axis that extends along the beam parallel to the longitudinal center axis; wherein the first, second, third, fourth, fifth, sixth, seventh, and eighth resistors have matching resistor type; wherein the first, second, third, and fourth resistors arranged to overlay first side face of the beam, are located at a first side face of the beam, such that a voltage offset between the first and second voltage divider outputs represents magnitude of a first force imparted to the beam in a first force direction normal to the longitudinal axis; and wherein the fifth, sixth, seventh, and eighth resistors arranged to overlay a second side face of the beam adjacent to the first side face of the beam, are positioned upon the beam such that a voltage offset between the third and fourth are located at a second side face of the beam adjacent to the first side face, such that a voltage divider offset between the first and second voltage divider outputs represents magnitude of a second force imparted to the beam in a second force direction normal to the longitudinal axis and normal to the first force direction.

Example 17 can include the subject matter of Example 16 wherein the first, second, third, fourth, fifth, sixth, seventh, and eighth resistors are strain type resistors.

Example 18 can include the subject matter of Example 16 wherein the first, second, third, fourth, fifth, sixth, seventh, and eighth resistors have matching resistor values.

Example 19 can include the subject matter of Example 16 wherein the first, third, fifth, and seventh resistors are arranged to be located at the proximal portion of the beam; and wherein the second, fourth, sixth, and eighth resistors are arranged to be located at the proximal portion of the beam.

Example 20 can include the subject matter of Example 16 wherein the first, third, fifth, and seventh resistors are arranged to be positioned at matching longitudinal locations of the beam; and wherein the second, fourth, sixth, and eighth resistors are arranged to be positioned at matching longitudinal locations of the beam.

Example 21 can include, for use with a beam having a proximal portion and a distal portion and having a longitudinal center axis extending between the proximal portion and the distal portion, a metal sheet comprising: a first cut-out section configured to overlay a first portion of the beam including: a first gauge resistor ('first resistor') and a second gauge resistor ('second resistor') coupled to provide a first voltage divider output, arranged to overlay the first portion of the beam and to extend along a first side axis that extends along the beam parallel to the longitudinal center axis; and a third gauge resistor ('third resistor') and a fourth gauge resistor ('fourth resistor') coupled to provide a second voltage divider output, arranged to overlay the first portion of the beam and to extend along a second side axis that extends along the beam parallel to the longitudinal center axis; a second cut-out section configured to overlay a second portion of the beam including: a fifth gauge resistor ('fifth resistor') and a sixth gauge resistor ('sixth resistor') coupled to provide a third voltage divider output, arranged to overlay the second portion of the beam and to extend along a third side axis that extends along the beam parallel to the longitudinal center axis; and a seventh gauge resistor ('seventh resistor') and a eighth gauge resistor ('eighth resistor') coupled to provide a fourth voltage divider output, arranged to overlay the second portion of the beam and to extend along a fourth side axis that extends along the beam parallel to the longitudinal center axis; wherein the first, second, third, fourth, fifth, sixth, seventh, and eighth resistors have matching resistor type; wherein the first and second resistors arranged to overlay the first portion of the beam and to extend along the first side axis, and the third and fourth resistors arranged to overlay the first portion of the beam and extend along the second side axis, are arranged to be positioned upon the beam such that a voltage offset between the first and second voltage divider outputs represents magnitude of a first force imparted to the beam in a first force direction normal to the longitudinal axis and normal to the first and second side axes and parallel to the third and fourth side axis; and wherein the fifth and sixth resistors arranged to overlay the second portion of the beam and to extend along the third side axis, and the seventh and eighth resistors arranged to overlay the second portion of the beam and to extend along the fourth side axis, are arranged to be positioned upon the beam such that a voltage offset between the third and fourth voltage divider outputs represents magnitude of a second force imparted to the beam in a second force direction normal to the longitudinal axis, parallel to the first and second axes and normal to the third and fourth side axes.

Example 22 can include the subject matter of Example 22 wherein the first side axis extends within a first plane that includes the longitudinal center axis; wherein the first side axis extends within a first plane that includes the longitudinal center axis; wherein the second force direction bisects a first separation angle between the first and second planes; wherein the third side axis extends within a third plane that includes the longitudinal center axis; wherein the fourth side axis extends within a fourth plane that includes the longitudinal center axis; and wherein the first force direction bisects a second separation angle between the third and fourth planes.

Example 23 can include the subject matter of Example 22 wherein the first separation angle equals the second separation angle.

Example 24 can include a force sensor comprising: a beam having a proximal portion and a distal portion and having a longitudinal center axis extending between the proximal portion and the distal portion; a first full-bridge circuit on the beam, having a first neutral axis and including: a first half-bridge circuit first gauge resistor ('first resistor') and a second gauge resistor ('second resistor') arranged along a first lateral side axis parallel to the longitudinal center axis and coupled to provide a first voltage divider output; and a second half-bridge circuit including third gauge resistor ('third resistor') and a fourth gauge resistor ('fourth resistor') arranged along a second lateral side axis parallel to the longitudinal center axis and coupled to provide a second voltage divider output; wherein the first and second lateral side axes are laterally spaced apart from one another on opposite sides of the first neutral axis; further including: multiple first center conductor traces extending parallel to the neutral axis in a region of the beam that is between the first resistor and the second resistor and that is between the third resistor and the fourth resistor.

Example 25 can include a force sensor comprising: a beam having a proximal portion and a distal portion and having a longitudinal center axis extending between the proximal portion and the distal portion; a first full-bridge circuit on the beam, having a first neutral axis and including: a first half-bridge circuit first gauge resistor ('first resistor') and a second gauge resistor ('second resistor') arranged along a first lateral side axis parallel to the longitudinal center axis and coupled to provide a first voltage divider output; and a second half-bridge circuit including third gauge resistor ('third resistor') and a fourth gauge resistor ('fourth resistor') arranged along a second lateral side axis parallel to the longitudinal center axis and coupled to provide a second voltage divider output; wherein the first and second lateral side axes are laterally spaced apart from one another on opposite sides of the first neutral axis, wherein the first, second, third, and fourth resistors have a matching resistor type; and wherein the first full-bridge circuit is arranged on the beam such that a component of an applied force in a first direction perpendicular to the longitudinal center axis can be determined based upon a difference between a first off-axis force imparted to the first half-bridge and a second off-axis force imparted to the second half-bridge.

Example 26 includes the subject matter of claim 25 further including: a second full-bridge circuit on the beam, having a second neutral axis and including: a fifth gauge resistor ('fifth resistor') and a sixth gauge resistor ('sixth resistor') arranged along a third lateral side axis parallel to the longitudinal center axis and coupled to provide a third voltage divider output; and a seventh gauge resistor ('seventh resistor') and an eighth gauge resistor ('eighth resistor') arranged along a fourth lateral side axis parallel to the longitudinal center axis and coupled to provide a fourth voltage divider output; wherein the third and fourth lateral side axes are laterally spaced apart from one another on opposite sides of the second neutral axis; further including: multiple first center conductor traces extending parallel to the second neutral axis in a region of the beam that is between the fifth resistor and the sixth resistor and that is between the seventh resistor and the eighth resistor.

Example 27 includes the subject matter of claim 26 wherein the first, second, third, and fourth resistors have a matching resistor type; wherein the first full-bridge circuit is arranged on the beam such that a component of an applied force in a first direction perpendicular to the longitudinal center axis can be determined based upon a difference between a first off-axis force imparted to the first half-bridge and a second off-axis force imparted to the second half-bridge; wherein the fifth, sixth, seventh, and eighth resistors have a matching resistor type; and wherein the second full-bridge circuit is arranged on the beam such that a component of the applied force in a second direction perpendicular to the longitudinal center axis and perpendicular to the first direction can be determined based upon a difference between a third off-axis force imparted to the third half-bridge and a fourth off-axis force imparted to the fourth half-bridge.

Example 28 includes a force sensor comprising: a rectangular beam having a proximal portion and a distal portion and having a longitudinal center axis extending between the proximal portion and the distal portion; a first half-bridge circuit that includes a first gauge resistor ('first resistor') and a second gauge resistor ('second resistor') coupled to provide a first voltage divider output; a second half-bridge circuit that includes a third gauge resistor ('third resistor') and a fourth gauge resistor ('fourth resistor') coupled to provide a second voltage divider output; a third half-bridge circuit that includes a fifth gauge resistor ('fifth resistor') and a sixth gauge resistor ('sixth resistor') coupled to provide a third voltage divider output; and a fourth half-bridge circuit that includes a seventh gauge resistor ('seventh resistor') and an eighth gauge resistor ('sixth resistor') coupled to provide a fourth voltage divider output; wherein the first, second, third, fourth, fifth, sixth, seventh and eighth resistors have matching resistor type; wherein the first, second, third, and fourth resistors are positioned upon a first face of the beam and the fifth, sixth, seventh, and eighth resistors are positioned upon a second face of the beam that is reverse to the first face of the beam, such that, a voltage offset between the first and second voltage divider outputs represents magnitude of a first force imparted to the beam in a first force direction normal to the longitudinal axis; a voltage offset between the third and fourth voltage divider outputs represents magnitude of the first force; a voltage offset between the first and fourth voltage divider outputs represents magnitude of a second force imparted to the beam in a second force direction normal to the longitudinal axis and normal to the first force direction; and a voltage offset between the second and third voltage divider outputs represents magnitude of the second force.

Example 29 includes the subject matter of claim 28 wherein the first, second, third, fourth, fifth, sixth, seventh, and eighth resistors are strain type resistors.

Example 29 includes the subject matter of claim 28 wherein the first, second, third, fourth, fifth, sixth, seventh, and eighth resistors have matching resistor values.

Example 30 includes the subject matter of claim 28 wherein the first, third, fifth, and seventh resistors are located at the proximal portion of the beam; and wherein the second, fourth, sixth, and eighth resistors are located at the distal portion of the beam.

Example 31 includes the subject matter of claim 30 wherein the first, third, fifth, and seventh resistors are positioned at matching longitudinal locations of the beam; and wherein the second, fourth, sixth, and eighth resistors are positioned at matching longitudinal locations of the beam.

Exam 32 includes a force sensor comprising: a beam having a proximal portion and a distal portion and having a longitudinal center axis extending between the proximal portion and the distal portion; a first half-bridge circuit that includes a first gauge resistor ('first resistor') and a second gauge resistor ('second resistor') coupled to provide a first voltage divider output, arranged to extend along a first side axis that extends along the beam parallel to the longitudinal center axis; a second half-bridge circuit that includes a third gauge resistor ('third resistor') and a fourth gauge resistor ('fourth resistor') coupled to provide a second voltage divider output, arranged to extend along a second side axis that extends along the beam parallel to the longitudinal center axis; a third half-bridge circuit that includes a fifth gauge resistor ('fifth resistor') and a sixth gauge resistor ('sixth resistor') coupled to provide a third voltage divider output, arranged to extend along a third side axis that extends along the beam parallel to the longitudinal center axis; and a fourth half-bridge circuit that includes a seventh gauge resistor ('seventh resistor') and an eighth gauge resistor ('sixth resistor') coupled to provide a fourth voltage divider output, arranged to extend along a fourth side axis that extends along the beam parallel to the longitudinal center axis; wherein the first, second, third, fourth, fifth, sixth, seventh and eighth resistors have matching resistor type; wherein the first and second resistors that extend along the first side axis, and the third and fourth resistors that extend along the second side axis, are positioned upon the beam such that a voltage offset between the first and second voltage divider outputs represents magnitude of a first force imparted to the beam in a first force direction normal to the longitudinal axis and normal to the first, second, third, and fourth side axes; wherein the fifth and sixth resistors that extend along the third side axis, and the seventh and eighth resistors that extend along the fourth side axis, are positioned upon the beam such that a voltage offset between the third and fourth voltage divider outputs represents magnitude of the first force imparted to the beam in the first force direction normal to the longitudinal axis and normal to the first, second, third, and fourth side axes; wherein the first and second resistors that extend along the first side axis, and the seventh and eighth resistors that extend along the fourth side axis, are positioned upon the beam such that a voltage offset between the first and fourth voltage divider outputs represents magnitude of a second force imparted to the beam in a second force direction normal to the longitudinal axis and parallel to the first, second, third, and fourth side axes; and wherein the third and fourth resistors that extend along the first side axis, and the fifth and sixth resistors that extend along the third side axis, are positioned upon the beam such that a voltage offset between the second and third voltage divider outputs represents magnitude of the second force imparted to the beam in the second force direction normal to the longitudinal axis and parallel to the first, second, third, and fourth side axes.

Example 33 includes the subject matter of Example 32 wherein the first, second, third, fourth, fifth, sixth, seventh, and eighth resistors are strain type resistors.

Example 34 includes the subject matter of Example 32 wherein the first, second, third, fourth, fifth, sixth, seventh, and eighth resistors have matching resistor values.

Example 35 includes the subject matter of Example 32 wherein the first, third, fifth, and seventh resistors are located at the proximal portion of the beam; and wherein the second, fourth, sixth, and eighth resistors are located at the distal portion of the beam.

Example 36 includes the subject matter of Example 35 wherein the first, third, fifth, and seventh resistors are positioned at matching longitudinal locations of the beam; and wherein the second, fourth, sixth, and eighth resistors are positioned at matching longitudinal locations of the beam.

Example 37 includes the subject matter of Example 35 wherein the first, third, fifth, and seventh resistors are located in a proximal cross-section plane of the beam that is normal to the center axis and that has a second area moment of inertia that is isotropic for all axes within the proximal cross-section plane that pass through the longitudinal center axis; and wherein the second, fourth, sixth, and eighth resistors are located in a distal cross-section plane of the beam that is normal to the center axis and that has a second area moment of inertia that is isotropic for all axes within the distal cross-section plane that pass through the longitudinal center axis.

Example 38 includes the subject matter of Example 32 wherein the first side axis extends within a first plane that includes the longitudinal center axis; wherein the second force direction bisects a first separation angle between the first and second planes; wherein the third side axis extends within a third plane that includes the longitudinal center axis; wherein the fourth side axis extends within a fourth plane that includes the longitudinal center axis, and wherein the first force direction bisects a second separation angle between the first and fourth planes.

Example 39 includes the subject matter of claim 37 wherein the first and second angles are supplementary angles.

Example 40 includes a force sensor comprising: a rectangular beam having a proximal portion and a distal portion and having a longitudinal center axis extending between the proximal portion and the distal portion; a first half-bridge circuit that includes a first gauge resistor ('first resistor') and a second gauge resistor ('second resistor') coupled to provide a first voltage divider output; a second half-bridge circuit that includes a third gauge resistor ('third resistor') and a fourth gauge resistor ('fourth resistor') coupled to provide a second voltage divider output; a third half-bridge circuit that includes a fifth gauge resistor ('fifth resistor') and a sixth gauge resistor ('sixth resistor') coupled to provide a third voltage divider output; and a fourth half-bridge circuit that includes a seventh gauge resistor ('seventh resistor') and an eighth gauge resistor ('sixth resistor') coupled to provide a fourth voltage divider output; wherein the first, second, third, and fourth resistors are one of tension type and compression type and the fifth, sixth, seventh and eighth resistors are the other of tension type and compression type.

Example 41 includes the subject matter of Example 40 wherein the first, second, third, and fourth resistors are strain type resistors and the fifth, sixth, seventh, and eighth resistors are compression type resistors.

Example 42 includes the subject matter of Example 40 wherein the first, second, third, fourth, fifth, sixth, seventh, and eighth resistors have matching resistor values.

Example 43 includes the subject matter of Example 40 wherein the first, third, fifth, and seventh resistors are located at the proximal portion of the beam; and wherein the second, fourth, sixth, and eighth resistors are located at the distal portion of the beam.

Example 44 includes the subject matter of Example 43 wherein the first, third, fifth, and seventh resistors are positioned at matching longitudinal locations of the beam; and wherein the second, fourth, sixth, and eighth resistors are positioned at matching longitudinal locations of the beam.

Example 45 includes a force sensor comprising: a beam having a proximal portion and a distal portion and having a longitudinal center axis extending between the proximal portion and the distal portion; a first half-bridge circuit that includes a first gauge resistor ('first resistor') and a second gauge resistor ('second resistor') coupled to provide a first voltage divider output, arranged to extend along a first side axis that extends along the beam parallel to the longitudinal center axis; a second half-bridge circuit that includes a third gauge resistor ('third resistor') and a fourth gauge resistor ('fourth resistor') coupled to provide a second voltage divider output, arranged to extend along a second side axis that extends along the beam parallel to the longitudinal center axis; a third half-bridge circuit that includes a fifth gauge resistor ('fifth resistor') and a sixth gauge resistor ('sixth resistor') coupled to provide a third voltage divider output, arranged to extend along a third side axis that extends along the beam parallel to the longitudinal center axis; and a fourth half-bridge circuit that includes a seventh gauge resistor ('seventh resistor') and an eighth gauge resistor ('sixth resistor') coupled to provide a fourth voltage divider output, arranged to extend along a fourth side axis that extends along the beam parallel to the longitudinal center axis; wherein the first, second, third, and fourth resistors are tension type resistors; wherein the fifth, sixth, seventh, and eighth resistors are compression type resistors.

Example 46 includes the subject matter of Example 45 wherein the first, second, third, and fourth resistors are tension type resistors and the fifth, sixth, seventh, and eighth resistors are compression type resistors.

Example 47 includes the subject matter of Example 45 wherein the first, second, third, fourth, fifth, sixth, seventh, and eighth resistors have matching resistor values.

Example 48 includes the subject matter of Example 45 wherein the first, third, fifth, and seventh resistors are located at the proximal portion of the beam; and wherein the second, fourth, sixth, and eighth resistors are located at the proximal portion of the beam.

Example 49 includes the subject matter of Example 48 wherein the first, third, fifth, and seventh resistors are arranged to be positioned at matching longitudinal locations of the beam; and wherein the second, fourth, sixth, and eighth resistors are arranged to be positioned at matching longitudinal locations of the beam.

Example 50 includes the subject matter of Example 48 wherein the first, third, fifth, and seventh resistors are located in a proximal cross-section plane of the beam that is normal to the center axis and that has a second area moment of inertia that is isotropic for all axes within the proximal cross-section plane that pass through the longitudinal center axis; and wherein the second, fourth, sixth, and eighth resistors are located in a distal cross-section plane of the beam that is normal to the center axis and that has a second area moment of inertia that is isotropic for all axes within the distal cross-section plane that pass through the longitudinal center axis.

Example 51 includes the subject matter of claim 45 wherein the first side axis extends within a first plane that includes the longitudinal center axis; wherein the first side axis extends within a first plane that includes the longitudinal center axis; wherein the second force direction bisects a first separation angle between the first and second planes; wherein the third side axis extends within a third plane that includes the longitudinal center axis; wherein the fourth side axis extends within a fourth plane that includes the longitudinal center axis; and wherein the first force direction bisects a second separation angle between the third and fourth planes.

Example 52 includes the subject matter of claim 51 wherein the first and second angles are supplementary angles.

Example 53 includes a force sensor comprising: a beam having a proximal portion and a distal portion and having a longitudinal center axis extending between the proximal portion and the distal portion; a first full-bridge circuit including: a first gauge resistor ('first resistor') and a second gauge resistor ('second resistor') coupled to provide a first voltage divider output; and a third gauge resistor ('third resistor') and a fourth gauge resistor ('fourth resistor')

coupled to provide a second voltage divider output; and a second full-bridge circuit including: a fifth gauge resistor ('fifth resistor') and a sixth gauge resistor ('sixth resistor') a seventh gauge resistor ('seventh resistor') coupled to provide a third voltage divider output and an eighth gauge resistor ('eighth resistor') coupled to provide a fourth voltage divider output; wherein the first, second, third, and fourth resistors have matching resistor type; wherein the fifth and sixth resistors are a one of tension and compression resistor type and the seventh and eighth resistors are the other of tension and compression resistor type; wherein the first, second, third, and fourth resistors are located at a first side face of the beam, such that a voltage offset between the first and second voltage divider outputs represents magnitude of first force imparted to the beam in a first force direction normal to the longitudinal axis; and wherein the fifth, sixth, seventh, and eighth resistors are located at a second side face of the beam that is reverse to the first side face of the beam, such that a voltage offset between the third and fourth voltage divider outputs represents magnitude of second force imparted to the beam in a second force direction normal to the longitudinal axis and normal to the first force direction.

Example 54 includes the subject matter of Example 53 wherein the first, second, third, and fourth resistors are strain type resistors.

Example 54 includes the subject matter of Example 53 wherein the first, second, third, fourth, fifth, sixth, seventh, and eighth resistors have matching resistor values.

Example 55 includes the subject matter of Example 53 wherein the first, third, fifth, and seventh resistors are located at the proximal portion of the beam; and wherein the second, fourth, sixth, and eighth resistors are located at the proximal portion of the beam.

Example 56 includes the subject matter of Example 55 wherein the first, third, fifth, and seventh resistors are positioned at matching longitudinal locations of the beam; and wherein the second, fourth, sixth, and eighth resistors are positioned at matching longitudinal locations of the beam.

Example 57 includes a force sensor comprising: a beam having a proximal portion and a distal portion and having a longitudinal center axis extending between the proximal portion and the distal portion; a first full-bridge circuit including: a first gauge resistor ('first resistor') and a second gauge resistor ('second resistor') coupled to provide a first voltage divider output, arranged to extend along a first side axis that extends along the beam parallel to the longitudinal center axis; and a third gauge resistor ('third resistor') and a fourth gauge resistor ('fourth resistor') coupled to provide a second voltage divider output, arranged to extend along a second side axis that extends along the beam parallel to the longitudinal center axis; and a second full-bridge circuit including: a fifth gauge resistor ('fifth resistor') and a sixth gauge resistor ('sixth resistor') a seventh gauge resistor ('seventh resistor') coupled to provide a third voltage divider output and an eighth gauge resistor ('eighth resistor') coupled to provide a fourth voltage divider output, arranged to extend along a third side axis that extends along the beam parallel to the longitudinal center axis; wherein the first, second, third, and fourth resistors have matching resistor type; wherein the fifth and sixth resistors are a one of tension and compression resistor type and the seventh and eighth resistors are the other of tension and compression resistor type; wherein the first and second resistors that extend along the first side axis, and the third and fourth resistors that extend along the second side axis, are positioned upon the beam such that a voltage offset between the first and second voltage divider outputs represents magnitude of first force imparted to the beam in a first force direction normal to the longitudinal axis and normal to the first and second side axes; and wherein the fifth, sixth, seventh, and eighth resistors that extend along the third side axis, are positioned upon the beam such that a voltage offset between the third and fourth voltage divider outputs represents magnitude of second force imparted to the beam in a second force direction normal to the longitudinal axis and parallel to the first and second side axes.

Example 58 includes the subject matter of Example 57 wherein the first, second, third, and fourth resistors are strain type resistors.

Example 59 includes the subject matter of Example 57 wherein the first, second, third, fourth, fifth, sixth, seventh, and eighth resistors have matching resistor values.

Example 60 includes the subject matter of Example 57 wherein the first, third, fifth, and seventh resistors are located at the proximal portion of the beam; and wherein the second, fourth, sixth, and eighth resistors are located at the proximal portion of the beam.

Example 61 includes the subject matter of Example 60 wherein the first, third, fifth, and seventh resistors are positioned at matching longitudinal locations of the beam; and wherein the second, fourth, sixth, and eighth resistors are positioned at matching longitudinal locations of the beam.

Example 61 includes the subject matter of Example 57 wherein the first side axis extends within a first plane that includes the longitudinal center axis; wherein the first side axis extends within a first plane that includes the longitudinal center axis; wherein the second force direction bisects a first separation angle between the first and second planes.

Example 62 includes, for use with a rectangular beam having a proximal portion and a distal portion and having a longitudinal center axis extending between the proximal portion and the distal portion, a metal sheet comprising: a first cut-out section configured to overlay a first side face of the beam including; a first gauge resistor ('first resistor') and a second gauge resistor ('second resistor') coupled to provide a first voltage divider output; and a third gauge resistor ('third resistor') and a fourth gauge resistor ('fourth resistor') coupled to provide a second voltage divider output; and a second cut-out section configured to overlay a second side face of the beam that faces reverse to the first side face of the beam including: a fifth gauge resistor ('fifth resistor') and a sixth gauge resistor ('sixth resistor') a seventh gauge resistor ('seventh resistor') coupled to provide a third voltage divider output and an eighth gauge resistor ('eighth resistor') coupled to provide a fourth voltage divider output; wherein the first, second, third, and fourth resistors have matching resistor type; wherein the fifth and sixth resistors have a one of tension and compression resistor type and the seventh and eighth resistors have the other of tension and compression resistor type; wherein the first, second, third, and fourth resistors arranged to overlay the first side face of the beam, such that a voltage offset between the first and second voltage divider outputs represents magnitude of first force imparted to the beam in a first force direction normal to the longitudinal axis; and wherein the fifth, sixth, seventh, and eighth resistors are arranged to overlay the second side face of the beam that is reverse to the first side face of the beam, such that a voltage offset between the third and fourth voltage divider outputs represents magnitude of second force imparted to the beam in a second force direction normal to the longitudinal axis and normal to the first force direction.

Example 63 includes the subject matter of Example 61 wherein the first, second, third, fourth, fifth, sixth, seventh, and eighth resistors are strain type resistors.

Example 64 includes the subject matter of Example 61 wherein the first, second, third, fourth, fifth, sixth, seventh, and eighth resistors have matching resistor values.

Example 65 includes the subject matter of Example 61 wherein the first, third, fifth, and seventh resistors are located at the proximal portion of the beam; and wherein the second, fourth, sixth, and eighth resistors are located at the proximal portion of the beam.

Example 66 includes the subject matter of Example wherein the first, third, fifth, and seventh resistors are positioned at matching longitudinal locations of the beam; and wherein the second, fourth, sixth, and eighth resistors are positioned at matching longitudinal locations of the beam.

Example 68 includes, for use with a beam having a proximal portion and a distal portion and having a longitudinal center axis extending between the proximal portion and the distal portion, a metal sheet comprising: a first cut-out section configured to overlay a first portion of the beam including: a first gauge resistor ('first resistor') and a second gauge resistor ('second resistor') coupled to provide a first voltage divider output, arranged to overlay the first portion of the beam and to extend along a first side axis that extends along the beam parallel to the longitudinal center axis; and a third gauge resistor ('third resistor') and a fourth gauge resistor ('fourth resistor') coupled to provide a second voltage divider output, arranged to overlay the first portion of the beam and to extend along a second side axis that extends along the beam parallel to the longitudinal center axis; and a second cut-out section configured to overlay a second portion of the beam including: a fifth gauge resistor ('fifth resistor') and a sixth gauge resistor ('sixth resistor') a seventh gauge resistor ('seventh resistor') coupled to provide a third voltage divider output and an eighth gauge resistor ('eighth resistor') coupled to provide a fourth voltage divider output, arranged to overlay the second portion of the beam and to extend along a third side axis that extends along the beam parallel to the longitudinal center axis; wherein the first, second, third, and fourth resistors have matching resistor type; wherein the fifth and seventh resistors are strain type resistors; wherein the sixth and eighth resistors compression type resistors; wherein the first and second resistors arranged to overlay the first portion of the beam and to extend along the first side axis, and the third and fourth resistors arranged to overlay the first portion of the beam and to extend along the second side axis, are arranged to be positioned upon the beam such that a voltage offset between the first and second voltage divider outputs represents magnitude of first force imparted to the beam in a first force direction normal to the longitudinal axis and normal to the first and second side axes; and wherein the fifth, sixth, seventh, and eighth resistors arranged to overlay the second portion of the beam and to extend along the third side axis, are arranged to be positioned upon the beam such that a voltage offset between the third and fourth voltage divider outputs represents magnitude of second force imparted to the beam in a second force direction normal to the longitudinal axis and parallel to the first and second side axes; wherein the first side axis extends within a first plane that includes the longitudinal center axis; wherein the second side axis extends within a second plane that includes the longitudinal center axis; wherein the second force direction bisects a first separation angle between the first and second planes.

Example 69 includes the subject matter of Example 68 wherein the first side axis extends within a first plane that includes the longitudinal center axis; and wherein the first side axis extends within a first plane that includes the longitudinal center axis.

Example 70 includes a force sensor comprising: a beam including a proximal portion and a distal portion, a longitudinal center axis and a neutral axis that extends along a beam surface parallel to the center axis; a first Wheatstone half-bridge ("half-bridge") including tension resistors; a second half-bridge including tension resistors; a third half-bridge including compression resistors; a fourth half-bridge including compression resistors; the first and third half-bridges arranged along a first side axis; the second and fourth half-bridges are arranged along a second a side axis; the first and second side axes extend along the beam surface parallel to the neutral axis on opposite sides of the neutral axis and equidistant from the neutral axis.

Example 71 includes method to identify a malfunction of the force sensor of Example 70 comprising: imparting a force to the force sensor; measuring a pair of orthogonal components of the imparted force using each of four different combinations of three half-bridges from a group, the group consisting of the first half-bridge, the second half-bridge, the third half-bridge, and the fourth half-bridge, to produce four pairs of force measurements, each pair of force measurements including a first force component measurement of the imparted force and a second force component measurement of the imparted force, the first force component orthogonal to the second force component; comparing the first force component measurements from each pair of force measurements; comparing the second force component measurements from each pair of force measurements; producing an electronic signal to report an error in response to a mismatch of a first force component measurement of one of the pairs of force measurements and a first force component measurement of at least one other of the pairs of force measurements; and producing an electronic signal to report an error in response to a mismatch of a second force component measurement of one of the pairs of force measurements and a second force component measurement of at least one other of the pairs of force measurements.

One of ordinary skill in the art would recognize many variations, alternatives, and modifications. Thus, the scope of the disclosure should be limited only by the following claims, and it is appropriate that the claims be construed broadly and, in a manner, consistent with the scope of the examples disclosed herein. The above description is presented to enable any person skilled in the art to create and use a force sensor with a beam and a distributed bridge circuit. Various modifications to the examples will be readily apparent to those skilled in the art, and the generic principles defined herein may be applied to other examples and applications without departing from the scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of examples in accordance with the present invention are merely illustrative of the principles of the invention. Therefore, it will be understood that various modifications can be made to the examples by those skilled in the art without departing from the scope of the invention, which is defined in the appended claims.

The invention claimed is:

1. A force sensor comprising:
a beam, the beam including a planar lateral surface and a longitudinal center axis with each extending longitudinally between a proximal portion and a distal portion, a neutral axis extending along the lateral surface parallel to the longitudinal center axis, a first lateral side axis and a second lateral side axis extending in parallel along the lateral surface on either side of and parallel to the neutral axis; and
a first half-bridge circuit, a second half-bridge circuit, a third half-bridge circuit, and a fourth half-bridge circuit coupled to the planar lateral surface, wherein:
a first plane is defined by the longitudinal center axis and the first lateral side axis,
a second plane is defined by the longitudinal center axis and the second lateral side axis,
the first half-bridge circuit includes a first proximal tension strain gauge resistor and a first distal tension strain gauge resistor arranged along the first lateral side axis,
the second half-bridge circuit includes a second proximal tension strain gauge resistor and a second distal tension stain gauge resistor arranged along the second lateral side axis,
the third half-bridge circuit includes a first proximal compression strain gauge resistor and a first distal compression strain gauge resistor arranged along the first lateral side axis,
the fourth half-bridge circuit includes a second proximal compression strain gauge resistor and a second distal compression strain gauge resistor arranged along the second lateral side axis,
an output of each of the first and third half-bridge circuits in response to an external force applied to the beam is indicative of a first plane strain force within the first plane that is an off-axis force relative to a beam coordinate system,
an output of each of the second and fourth half-bridge circuits in response to the external force applied to the beam is indicative of a second plane strain force within the second plane that is an off-axis force relative to the beam coordinate system, and
a combination of the first plane strain force indications and the second plane strain force indications is indicative of a magnitude and a direction of the external force applied to the beam.

2. The force sensor of claim 1, wherein:
the first lateral side axis and the second lateral side axis are equidistant from the neutral axis.

3. The force sensor of claim 1, wherein:
the first plane and the second plane are separated by a separation angle;
the beam coordinate system is defined for the beam and has three coordinate axes orthogonal to one another;
the three coordinate axes include a first coordinate axis and a second coordinate axis;
the first plane strain force includes a first strain force component in the first coordinate axis and a second strain force component in the second coordinate axis;
the second plane strain force includes a third strain force component in the first coordinate axis and a fourth strain force component in the second coordinate axis;
the first strain force component, the second strain force component, the third strain force component, and the fourth strain force component are determined at least in part by the separation angle; and
a combination of the first strain force component, the second strain force component, the third strain force component, and the fourth strain force component is indicative of the magnitude and the direction of the external force applied to the beam.

4. The force sensor of claim 3, wherein:
a first bridge circuit combination includes any three of the first half-bridge circuit, the second half-bridge circuit, the third half-bridge circuit, and the fourth half-bridge circuit;
a second bridge circuit combination includes any three of the first half-bridge circuit, the second half-bridge circuit, the third half-bridge circuit, and the fourth half-bridge circuit, the second bridge circuit combination being different than the first bridge circuit combination;
an output of the first bridge circuit combination provides a first indication of the magnitude and the direction of the external force applied to the beam;
an output of the second bridge circuit combination provides a second indication of the magnitude and the direction of the external force applied to the beam; and
the first indication and the second indication are redundant.

5. The force sensor of claim 4, wherein:
a difference between the first indication and the second indication is indicative of a malfunction of the force sensor.

6. The force sensor of claim 1, wherein:
the first proximal tension strain gauge resistor, the first distal tension strain gauge resistor, the first proximal compression strain gauge resistor, and the first distal compression strain gauge resistor are arranged along the first lateral side axis;
the second proximal tension strain gauge resistor, the second distal tension strain gauge resistor, the second proximal compression strain gauge resistor, and the second distal compression strain gauge resistor are arranged along the second lateral side axis;
one of the first proximal tension strain gauge resistor and the first distal tension strain gauge resistor is located along the first lateral side axis between the first proximal compression strain gauge resistor and the first distal compression strain gauge resistor; and
one of the second proximal tension strain gauge resistor and the second distal tension strain gauge resistor is located along the second lateral side axis between the second proximal compression strain gauge resistor and the second distal compression strain gauge resistor.

7. The force sensor of claim 6, wherein:
one of the first proximal compression strain gauge resistor and the first distal compression strain gauge resistor is located along the first lateral side axis between the first proximal tension strain gauge resistor and the first distal tension strain gauge resistor; and
one of the second proximal compression strain gauge resistor and the second distal compression strain gauge resistor is located along the second lateral side axis between the second proximal tension strain gauge resistor and the second distal tension strain gauge resistor.

8. The force sensor of claim 6, wherein:
the first proximal tension strain gauge resistor and the second proximal tension strain gauge resistor are positioned at matching longitudinal locations on the lateral surface of the beam;
the first distal tension strain gauge resistor and the second distal tension strain gauge resistor are positioned at matching longitudinal locations on the lateral surface of the beam;
the first proximal compression strain gauge resistor and the second proximal compression strain gauge resistor are positioned at matching longitudinal locations on the lateral surface of the beam; and
the first distal compression strain gauge resistor and the second distal compression strain gauge resistor are positioned at matching longitudinal locations on the lateral surface of the beam.

9. The force sensor of claim 1, wherein:
the force sensor further includes a metal sheet overlaying the beam; and
the first half-bridge circuit, the second half-bridge circuit, the third half-bridge circuit, and the fourth half-bridge circuit are coupled to the metal sheet.

10. A method for controlling an instrument, the method comprising:
receiving, at a computer system, a plurality of outputs from a force sensor coupled to the instrument, the force sensor including a first half-bridge circuit, a second half-bridge circuit, a third half-bridge circuit, and a fourth half-bridge circuit coupled to a planar lateral surface of a beam that includes a longitudinal center axis extending longitudinally between a proximal portion and a distal portion, a neutral axis extending along the lateral surface parallel to the longitudinal center axis, a first lateral side axis and a second lateral side axis extending in parallel along the lateral surface on either side of and parallel to the neutral axis, wherein:
a first plane is defined by the longitudinal center axis and the first lateral side axis and a second plane is defined by the longitudinal center axis and the second lateral side axis,
the first half-bridge circuit and the third half-bridge circuit are arranged along the first lateral side axis,
the second half-bridge circuit and the fourth half-bridge circuit are arranged along the second lateral side axis,
the plurality of outputs from the force sensor includes at least a first half-bridge circuit voltage, a second half-bridge circuit voltage, a third half-bridge circuit voltage, and a fourth half-bridge circuit voltage
wherein the first half-bridge circuit voltage is from the first half-bridge circuit or the third half-bridge circuit, and
wherein the second half-bridge circuit voltage is from the second half-bridge circuit or the fourth half-bridge circuit;
determining, via the computer system, a first indication of a first plane strain force in the first plane based at least in part on the first half-bridge circuit voltage and a second indication of the first plane strain force based at least in part on the third half-bridge circuit voltage, the first plane strain force being an off-axis force relative to a beam coordinate system defined for the beam;
determining, via the computer system, a first indication of a second plane strain force in the second plane based at least in part on the second half-bridge circuit voltage and a second indication of the second plane strain force based at least in part on the fourth half-bridge circuit voltage, the second plane strain force being an off-axis force relative to a beam coordinate system;
determining, via the computer system, a determined external force applied to the beam based on any three of the first indication of the first plane strain force, the second indication of the first plane strain force, the first indication of the second plane strain force, and the second indication of the second plane strain force; and
providing a haptic feedback to an operator of the instrument based at least in part on the determined external force applied to the beam.

11. The method of claim 10, wherein:
the first lateral side axis and the second lateral side axis are equidistant from the neutral axis.

12. The method of claim 10, wherein:
the first plane and the second plane are separated by a separation angle;
the beam coordinate system has three coordinate axes orthogonal to one another
the three coordinate axes include a first coordinate axis and a second coordinate axis;
determining, via the computer system, the determined external force applied to the beam based on the first plane strain force and the second plane strain force includes:
determining for each of the first indication and the second indication of the first plane strain force a first strain force component of the first plane strain force in the first coordinate axis and a second strain force component of the first plane strain force in the second coordinate axis via the computer system and based at least in part on the separation angle,
determining for each of the first indication and the second indication of the second plane strain force a third strain force component of the second plane strain force in the first coordinate axis and a fourth strain force component of the second plane strain force in the second coordinate axis via the computer system and based at least in part on the separation angle, and
determining, via the computer system, a determined direction and a determined magnitude of the determined external force based on a portion of the strain force components in the first coordinate axis and a portion of the strain force components in the second coordinate axis corresponding to each of the first plane and the second plane; and
the haptic feedback is based at least in part on the determined direction and the determined magnitude of the determined external force.

13. The method of claim 10, wherein:
determining the determined external force applied to the beam includes determining a first determined external force applied to the beam based on a first combination of any three of the first indication of the first plane strain force, the second indication of the first plane strain force, the first indication of the second plane strain force, and the second indication of the second plane strain force and a second determined external force applied to the beam based on a second combination of any three of the first indication of the first plane strain force, the second indication of the first plane strain force, the first indication of the second plane strain force, and the second indication of the second plane strain force;

the second combination is different than the first combination; and the second indication is redundant to the first indication.

14. The method of claim 13, wherein:

the method further includes outputting an indication of a malfunction of the force sensor upon an event in which a difference between the first indication and the second indication exists.

15. The method of claim 10, wherein:

the first half-bridge circuit includes a first proximal tension strain gauge resistor located at the proximal portion of the beam and a first distal tension strain gauge resistor located at the distal portion of the beam;

the second half-bridge circuit includes a second proximal tension strain gauge resistor located at the proximal portion of the beam and a second distal tension strain gauge resistor located at the distal portion of the beam;

the third half-bridge circuit includes a first proximal compression strain gauge resistor located at the proximal portion of the beam and a first distal compression strain gauge resistor located at the distal portion of the beam;

the fourth half-bridge circuit includes fourth a second proximal compression strain gauge resistor located at the proximal portion of the beam a second distal compression strain gauge resistor located at the distal portion of the beam;

the first proximal tension strain gauge resistor, the first distal tension strain gauge resistor, the first proximal compression strain gauge resistor, and the first distal compression strain gauge resistor are arranged along the first lateral side axis;

the second proximal tension strain gauge resistor, the second distal tension strain gauge resistor, the second proximal compression strain gauge resistor, and the second distal compression strain gauge resistor are arranged along the second lateral side axis;

one of the first proximal tension strain gauge resistor and the first distal tension strain gauge resistor is located along the first lateral side axis between the first proximal compression strain gauge resistor and the first distal compression strain gauge resistor; and one of the second proximal tension strain gauge resistor and the second distal tension strain gauge resistor is located along the second lateral side axis between the second proximal compression strain gauge resistor and the second distal compression strain gauge resistor.

16. The method of claim 15, wherein:

one of the first proximal compression strain gauge resistor and the first distal compression strain gauge resistor is located along the first lateral side axis between the first proximal tension strain gauge resistor and the first distal tension strain gauge resistor; and one of the second proximal compression strain gauge resistor and the second distal compression strain gauge resistor is located along the second lateral side axis between the second proximal tension strain gauge resistor and the second distal tension strain gauge resistor.

17. The method of claim 15, wherein:

the first proximal tension strain gauge resistor and the second proximal tension strain gauge resistor are positioned at matching longitudinal locations on the lateral surface of the beam;

the first distal tension strain gauge resistor and the second distal tension strain gauge resistor are positioned at matching longitudinal locations on the lateral surface of the beam;

the first proximal compression strain gauge resistor and the second proximal compression strain gauge resistor are positioned at matching longitudinal locations on the lateral surface of the beam; and the first distal compression strain gauge resistor and the second distal compression strain gauge resistor are positioned at matching longitudinal locations on the lateral surface of the beam.

18. The method of claim 10, wherein:

the force sensor further includes a metal sheet overlaying the beam; and the first half-bridge circuit, the second half-bridge circuit, the third half-bridge circuit, and the fourth half-bridge circuit are coupled to the metal sheet.

* * * * *

UNITED STATES PATENT AND TRADEMARK OFFICE
CERTIFICATE OF CORRECTION

PATENT NO. : 12,379,267 B2  
APPLICATION NO. : 17/776429  
DATED : August 5, 2025  
INVENTOR(S) : Ashwinram Suresh Page 1 of 1

It is certified that error appears in the above-identified patent and that said Letters Patent is hereby corrected as shown below:

In the Claims

Column 61, Line 26 (Claim 15): "circuit includes fourth a second" should be -- circuit includes a second --

Signed and Sealed this  
Ninth Day of September, 2025

Coke Morgan Stewart  
*Acting Director of the United States Patent and Trademark Office*